US011459577B2

(12) United States Patent
Qin et al.

(10) Patent No.: US 11,459,577 B2
(45) Date of Patent: Oct. 4, 2022

(54) TARGETED INSERTION SITES IN THE MAIZE GENOME

(71) Applicant: SYNGENTA PARTICIPATIONS AG, Basel (CH)

(72) Inventors: Yinping Lucy Qin, Research Triangle Park, NC (US); Mark Rose, Research Triangle Park, NC (US); Zhongying Chen, Research Triangle Park, NC (US); Heng Zhong, Research Triangle Park, NC (US); Weining Gu, Research Triangle Park, NC (US); Wenling Wang, Research Triangle Park, NC (US); Qiudeng Que, Research Triangle Park, NC (US); Ailing Zhou, Research Triangle Park, NC (US); Mary-Dell Chilton, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/757,851

(22) PCT Filed: Dec. 12, 2018

(86) PCT No.: PCT/US2018/065114

§ 371 (c)(1),
(2) Date: Apr. 21, 2020

(87) PCT Pub. No.: WO2019/125851

PCT Pub. Date: Jun. 27, 2019

(65) Prior Publication Data

US 2021/0189409 A1 Jun. 24, 2021

Related U.S. Application Data

(60) Provisional application No. 62/599,831, filed on Dec. 18, 2017.

(51) Int. Cl.
*C12N 15/82* (2006.01)
*A01H 6/46* (2018.01)

(52) U.S. Cl.
CPC ....... *C12N 15/8213* (2013.01); *A01H 6/4684* (2018.05)

(58) Field of Classification Search
None
See application file for complete search history.

(56) References Cited

U.S. PATENT DOCUMENTS 9,970,001 B2 * 5/2018 Miller .................... C12N 15/63

FOREIGN PATENT DOCUMENTS

WO 2015/066636 A2 5/2015
WO WO-2016106121 A1 * 6/2016 ......... C12N 15/1058

OTHER PUBLICATIONS

Clark, Pattern of diversity in the genomic region near the maize domestication gene tb1, Proceedings of the National Academy of Sciences, Jan. 20, 2004 (Year: 2004).*
GenBank: AF464738.1, "*Zea mays* cultivar B73 putative gag protein, putative gag-pol precursor, putative transposase, putative copia-type pol polyprotein, putative copia-like retrotransposon Hopscotch polyprotein, putative gag protein, putative prpol, putative prpol", Jan. 19, 2006 (Year: 2006).*
Blast N RID: CS5569DZ01R (Year: 2021).*
Genbank AC208423, *Zea mays* cultivar B73 chromosome 4 clone CH201-244D17, Sequencing in Progress, 2 unordered pieces, NCBI, https://www.ncbi.nlm.nih.gov/nuccore/AC208423.3, Jul. 29, 2008 (Year: 2008).*
GenBank Submission AC155451, *Zea Mays* Strain B73 clone ZMMBBb0369D20 (Jan. 25, 2005).
International Seach Report for International Application No. PCT/US18/65114, dated Apr. 1, 2019.

* cited by examiner

*Primary Examiner* — Amjad Abraham
*Assistant Examiner* — Brian James Sullivan
(74) *Attorney, Agent, or Firm* — Dale Skalla

(57) ABSTRACT

The present invention relates to methods and compositions for targeted insertion of polynucleotide molecules into ideal target sites in the genome of a maize plant. The present invention relates to maize recombinant molecules comprising heterologous sequences and also to methods of integrating a DNA of interest into a target maize genomic locus in a maize genome. The present invention also relates to regenerated maize plants or plant parts comprising the recombinant molecules and/or a DNA of interest.

16 Claims, No Drawings

Specification includes a Sequence Listing.

SEQUENCE LISTING

```
<160> NUMBER OF SEQ ID NOS: 105

<210> SEQ ID NO 1
<211> LENGTH: 1772
<212> TYPE: DNA
<213> ORGANISM: Zea mays

<400> SEQUENCE: 1

gtacgtaacg aatctacgtt aagatcaatc tcttcgtgga gattcggatc cttttacttc     60

tagacgaggg aaggaaagtt tccctgggtc gtgacagtta gttgggccgt gtactgggtg    120

tagaatgtca ggcgcgttcc aagtatcgct aaagcccaag tggcaggctg atcgatgcat    180

cttggcccat tagtcggata ggtggttgct cgtcctagac cacaatggtc cagcagtcca    240

tgaaaccatc aggcccacaa gtttgttccc accgaaaata gtttccgctc cgcctccgag    300

cccgcccggc ccggctgccc gccaccgccg atctccccca ccgcaaccca ccttgagacc    360

tgagcgagcg tcaccccgac gcgcgggtcg accccgaagc cgccggcgag ccacagctag    420

catacgcgga cgatccgggg actctgctcg cctcgtgatt gctgctggct tgccggtggt    480

gtcatcggta cgtgttctgt atgaccgaat tcctcgttgg cggcagcagc agagaatgca    540

gggtggtgcc gcgtatgtag cagcgcttgc tggttgcgcc gccgcacagc agctgagcgc    600

ctgactggga gcctcagatc ctacgcgcat gtatgcatgt gacgcgccat gcattaaccc    660

catcagagct cagggtttca gctttcactt caggagtcag gatcagaatt cagaaagggt    720

ttcagttgag cctacaacct gtcaacctcc tatatacata catagggctt gcttcgttcg    780

ctcgtcgtcg atggacagac agatgcggta tgccgctcat gcatgttagc tgttgttgtg    840

tgccctccat cagttcgatt atggattttt aagtgggcat gcagcatgta cgcgtgtacg    900

tacgcggcgc cgtgacgacg ccgcgccccg accgcgaccg gccagcaggc cgagacgctc    960

gccgcctgat tcgcgcgcgc gccatgccca tgctgtgttg ctagctgctc aaactcacat   1020

gcctccgatc cggagtccgg ctagcaccta gcagcgagct tcgctcacat tccttgcctg   1080

cgtgcggtgc gtgcagtaca gcgactgcag cgagtttcgt tcttcagaat tcgccgacta   1140

ctggatcgat tcatagtttc agacttaaga agaaaggact aaactgaaag ggatgcgatg   1200

tgccctctca aggactgaag cgtccttttt ctctcaaacg acgacaggag gggggccgcg   1260

ccggccgggc cagcgtgcgt gctcatcgcc gccgcagcag ggatcggaga cgggagggac   1320

cgccccacct gcctggcaag ctcacggcga ttacagttgc gttacaggga ggatcgatgg   1380

cagctgcagg gcgctgtgat gcatatgctg atgcctgcac agtggcggag ttatgtgtgc   1440
```

```
gggaacaaac gaacaggacg ccgggaggcc aggccagcgt gctctcgcta acggaggcag   1500

gcgcagcgca aggacctcat ccatccaccc ctccacaccg tgcccaccac caccggttct   1560

ggcagagttt caggcagctg caactgcatg caatgcaatg cagcagcagg gagcgccggc   1620

agtgccttca ttttttttt gtgctccacc cccacagctc cactgcatgg tgcgtggcgc    1680

atgccatgga agcactacga cgcaacactg gtcggcgtaa acacatgcac gaggaagagg   1740

tggaggagag ggcttgcttt ttcacgtgac ac                                 1772
```

<210> SEQ ID NO 2
<211> LENGTH: 1961
<212> TYPE: DNA
<213> ORGANISM: Zea mays

<400> SEQUENCE: 2

```
gcaaatatga cgaagttaaa acgtgaaatc aagccactgg gatacatgga catttgagat     60

cagtccagat ctctctctct ttttttgctg cccagtgctt gctgcagttc caaccattat    120

gctgtcatat gttcatatat tgagttgtga tgttcatgta tcatgaatac acaacagtgc    180

taaaatgttt agaaatcagt ctagctggta ggaagcttaa tggaaattca tcatatcttc    240

cctgcgacct gaatttgggg cttccaaact acctgaagtt ggttacagat tctagattac    300

tgtttggtga tattaggact ggaactctat tctggcttgt agcttctcaa gtcattggaa    360

gtgatttaga caaggcctag atttttgttt gttggaccaa tttttaaatc tgaagctttg    420

tgcaattaaa gcagataatg tacataggca gcaggttagt ttagctacgc aggctgccat    480

tccaaacaca tcgttgcagt gaagcatcaa atctaattaa aacatgtatg ataaacatgt    540

catagcttac ctatgccaat aagcagaata tttctcaact atatctatag gttgctgcaa    600

gcaatattga atttgaagga acttgcccaa gtttcatttt ataacacatt gaggtgtcat    660

gtcgattaaa ttaaatggag ttgccaattc atatcacatt tttttattgt acctccactt    720

agcacttttg caatactttc aagaacgtta ggtcttttgg tgggtggtgg taatatactc    780

gtcttcaggg ggatgccaca tgaagaaaca aatgcagtcc ttttagcttc attgttagag    840

gctttccagt ccttttgaga tgagctcttc aatacactgc ttgtacttta tatcatttga    900

tcttaaatac tttgtgacaa accccctgtt cttccaattt aatctggtta agtgcagtag    960

agcatctctc tgcatgactg ttgcataagt tttgctggtt cttgtgagtt catttcatag   1020

caggataatg caataccaaa gtgatgcttg tatacattat actggcatac tgcatccact   1080

cttcctatat aagcaacata aattaattac cctagggggt tcatctgttg cccattgggc   1140

ttgccttgac tatcggcaat cgttcctcta gcagcagaat ggggaacccc ttaatggcat   1200

tgaaaacggt accctttagt ggatattgag attttacttt taagcttttg ggcattgtat   1260

tcaatcactg atatttccat aaaaaggata accacaggtt gaactttaca atggggtttg   1320

cagttactag cataaatatgg ccctgttaag cggacaagtg ctggtaaatt tttatttcca  1380

tttgccacac ataattctta gttctattta tttactatat tagcttttct tgtgttgctt   1440

atggctggat acaagctcag cgtgatgtta gtaactggcc tggtcattag caatcgtatg   1500

gaaaccaggg acatggaata ggaactctct tttgtgaaca atagctgctg tcagcctgtc   1560

agttttactc tgtgcgcatc taatgcatga tagattgaaa cacatcggat gtgatgttta   1620

aggaatcttt tgtatcggat ctggatcata tggtcacaac cttcccactg taaaacacgt   1680

cttgttagct tttctgcagt cttgtctgat aattccattt gcatgccatg acaaccgaca   1740
```

```
acatgaacac aaacgacata ataataatgg caatagtgca tctataccta gtctcttttg   1800

gcttgccaat gtccatttgt gtttggtcaa tacctcggag ggactcccaa cacgtatatt   1860

ctatgaagtt catcttcaga gttatgttat gcccccctcc cacccccaa tgaaacttga   1920

caactacatt tttttggtgg ctctgtatga tgaagctgtt a                       1961
```

<210> SEQ ID NO 3
<211> LENGTH: 1763
<212> TYPE: DNA
<213> ORGANISM: Zea mays

<400> SEQUENCE: 3

```
tgtagggaat aatatcattg tgtcttccct agttcgtagt cctgaaatgg tcatcagcca     60

ccaaagatta ttcactttga accaactgtt ttttttataa aaaaagagcc acaaatcgag    120

atgccgaatt caccaatgcg ctacgttttc agtgacactg aggaacagtt tatcagggag    180

cgaggggggga aacgccgaaa cggcatcgga atcggaatga gaagcagaat ggggatttga   240

atgctgcggc ctgcgagagg gagcggagtg gaatggaatg tcccccgcag gtgccacccc    300

tacgagccgt ccaaaaccag gtcgaaattt acgccgccaa aagggccacg aaatccagaa    360

aaccccagag gaataaaggg ctctccgctt ggggggccgg gtgatgagag gtggatatat    420

atcttttcat gtcggtttcg gcctctgtgg gtaagagtgg tggggggtga cgctaatctc    480

cacgcgcgcg cggctcgctc gcgtccggtc cggcgctccg ctacgggatg catgtgcgag    540

tgtatgcctg ctgcctgcat gcgagattcc gacggcgacg caagagttat ctggaactcg    600

acggccgcag ctagccggcg gcccaaccag ttctttctcc ggagatgaca gcaaaaagac    660

ctggattcgg atgcttcacg gccgggggct gtcactcccc gctctccccg gccggtgatg    720

cgatcgaaga gagcagagca atccaacggg cctgtccatt tccaaagcat ttccaaagca    780

aattccgaga catacatata tgccggcggg ggccaagttg catgcgctcg cgtggcgtgg    840

cgtggcgctt tcgaatttcg atccggagca ggacgacgac gagccttgct cttgctatcg    900

agcacgacga tatattccat gcagcagcaa aatatgctaa cccacattaa caggctaggc    960

acagcaggtt tagcatggct ctgtatgtaa tacgtaaaat ggacagccat ggttttggtt   1020

tcgctagctt cgaggtcaaa agggtattaa cataattgac cttttaatca cgtacgtacg   1080

tcgaccatgg ccaggctgga ttcgaaaaaa aaagaggcta cttacggtat atatgtgtat   1140

aaactatgcc acaaaaaaaa actttgcttt gcagggggct taatggggga gggaatatat   1200

ctgaaaggga cggagcgaca gacgggagag attgcgtaag ggctaagtga cgcctttcga   1260

cggcgagctt tttttggggg ggctgcagtt gtgttgagag caacgtcaga cagacagaga   1320

gtaacggatg gcgataacga actcctcgga acagtgtagt gtagcggcag ggatggtttt   1380

tggaaagctg ggtttttttt tcttttcttc tggaaacaaa ttaaggccgg catgctatgc   1440

tactgagtgc tggccaggcc atcagtgacg gatgcacagg aggagcacct agtcctacgc   1500

aggaggacag atcgagcccc ggccggctgg ttgcacgtac ttattactac tagtgatata   1560

aaagcgagga gggacaggat ctaacatcta attgcctgta cgtactgaat atatgtcttg   1620

gtcgtcctgg tgtggagttg accagaggcc ggcgacatca tgtgacgcaa ttgtccagcc   1680

tgaaaaggcc aacattatca acactgcata ccttttctgc cgttggtaac aaacaaaaga   1740

ataatactgt agtagttttt tta                                           1763
```

<210> SEQ ID NO 4
<211> LENGTH: 2026

<212> TYPE: DNA
<213> ORGANISM: Zea mays

<400> SEQUENCE: 4

```
acatatcata tcgtcatccc atagtacaat gatttgctca aaaagcctag gctttaagga      60
caagttttga cacataaatt tatcgacgac aaaattttat gcccacaaac atgtgagaga     120
aacaaaggaa catgctaaaa gatagaatac atgttatcaa acatttttca agatttcata     180
atttaggaga tatacatgcg acttatcaaa atctctacct gctactggct tgtgtttttc     240
tataaaaagt attctcgact atttcctttc ctacgactga ctcccacctg gtagataccc     300
tcattcactt tattggacaa ttgagttttt ctttttgtca tgaagaccaa gaccttgtta     360
ccctttaata ttaagtaagg aataaacatc cttcaagaaa ataaaaccac ctataaaaac     420
ttcttcaata ttcgttgaag tatttcttca ttaaagttca ggtattctaa aggtttggag     480
aagttctaca aaaaatgtat ataaaatggt gcaacgtgat tcttgtagaa atctctccat     540
tgtctttctt aattttgaat ggaacaagga ctcaaaattt gagagtaatt aagtatatgg     600
gagaagctta tgtgctagca gattaggagt catttttttg cttagagtat taaaatgtga     660
agtaagtcat ctaactcatg aatcattgta ccatgtgcac atgtagtgcc taacacctat     720
gcgatgtaga catgggatgt taaacctaga gtagtcatag tgtgactttg ttttcgcaaa     780
aaaacaacta acattactag ggccagattg gcggtaagaa agactacacc atcaaaattt     840
agaaaggtca tgcatagatt gtatcacaaa aatactagat gttctatgat taaaaaacgt     900
tccaagaacg tggtgtcttt gttctttgac aagctattgg gcctgtacag gatcagctaa     960
ccccacatgc gctacaagat ctcacttgcc ctatccatct acatccaccc ctttcctctt    1020
tctttctcca tcgcaccata ttttttcctt cacccacatg gaagcacatg tctttttacc    1080
tttagctatc acattaggaa ggtgagtgtt gtctctcctc tacaaactat ggcgacaaga    1140
accacattag gaaggtgggt aacgatataa atgagccttt gaggggcagg atccaaggat    1200
taagtgctac ccacatgggc actctgattc cattgcctac cactagtaca ctgggaggag    1260
gtgaagtatg gggttcatcg aatgtggtgg gagagcgcta gggattgcat agttgaataa    1320
gggaaggatt ttttttcatg atacttagca ttagggctat aaggactaag atttcattct    1380
taggttcgat gatgaaggaa gctttgcggg ttgacatgtg gttggtaaga cgatgacaaa    1440
tttatgcttt ttaagactaa gacctaggaa tatgttccat caagggaatc ttacatctag    1500
actaggttac aagtcatcct ccatttggat atgattatgt ctaaaattgg ttgttagttt    1560
gtttttagtt gtttatccat acctcatgtg catgaacatg tatttggatg acaagtttat    1620
gtccctagga acacgaatga tcaaacacta gcaaccaaca atgatgtgtc aattttagat    1680
gtggagaagg atgatgaggg cctaaatgaa catgcaaagt accctagttc agagctagag    1740
tgtgatacaa gttgaaagct ttggtaatat gcatgctatg ttccttgttc ctttatatgc    1800
aaagataata aagataataa acttcaggag tatttatttt tcatagagaa tgtataagcc    1860
tagttcacca acatgcattt catgtatata aaaatattac atgttcaaat aagtaacttg    1920
tttatattac aattatttga aaaggatatt atgtttttca tgagctttag ttgtccaagt    1980
actcaatcac acactcatac aaattggcag tgataactaa tatatt                   2026
```

<210> SEQ ID NO 5
<211> LENGTH: 2819
<212> TYPE: DNA
<213> ORGANISM: Zea mays

<400> SEQUENCE: 5

```
cctctacatc tcccctccaa ttcccaaaga gtcaaagaca acggacgcag ctagctgtag      60
ctctctccct cctccggcgc aggtggcgcg ccgtacgtgg aaagatcggg ccgcttcgac     120
acgggcgcgc ggagcaagcg gactgaaggg cggtcacttg gcagcaaagc cagcaactac     180
cacgccacca ttacgacgac gacgaccggc ctggaggacg agatcctgcc tgcgacgtcg     240
tcgcgaggtt gttgacgaag ggcgtgcgcg tgcgcgagct gtacgtgtat atatgcaacc     300
acagcaagga tcgtaccgga agcgttggac gtcggtcgca gcgtggccgt gggttaccgg     360
ccaaagcgta tgtgacgcag gcacgcagcg aacgaaagcg gccggccggc cagattcaac     420
gccgcgcgtg ctcgcccggc cggccgtctg gtccaccggg taaccacact gccgcgctgc     480
ctgctcgtgg agatgcattg ctcacagtag taactctgtc gcctctgatc gagaggtgag     540
gccgtgatgc atgctcggac ttcttctctg gctcagtgac gctcgcatta gtggtggcct     600
acttggctcg ctctcagcca gcacagcagt gacagagcaa cggatcaacc gtctctgcac     660
gccgcacgcg ctactagaag accagtcgac cacaggaccc ggccgtctca tttccacgca     720
tcagtaaatc acttccagat gcacgtcgcc ctccgggcgc cttcgcacac cgtagcccac     780
ggctttctgt cgatcgggcc gggcgggtcc ctcggctcct ttgttctttc ccggcgagcg     840
gcgaccgcgc cacgcgacgc gacggcgccg tgcggcgcgc gcagcgccac acgatcgaat     900
ccagtcggcc gggcacgcac gcacgatcat cacgtgctcc tttaatttcc cggagcgcga     960
ctacgcccct gcctccatca gtccatctgc tccctgcggt gaggtcagcc atgcatgcag    1020
ctagcgtagc taggtgccgt tggatcggcc gcgaccgtac gtagcactat atagcagcag    1080
gcgacggatc agaacccccct ctgtgttcgg atctgtgtcg gaccagggag ggagggagag   1140
agagatagca gtgcaggccc cgccaagcgc ccggccgcca gtggccacga ggatatctgg    1200
atcgggcgat caatgatccg gtgccgtggc catcgaccag agcatcacac gacgcgttcg    1260
gcgcgggggga ggcttgtcag caggcagttc gaccgcgcga gagccccgga cggacgcccc   1320
gcgatacgga cggagggaat cccatggcgg gcgtacggcc gcggcgcggc gcaagggatc    1380
gatgcacggg attggaccgc agactgacag cgagatcgcg gcggacggcg ggcctgccgg    1440
ccgacatgca ccggccaggg tagtacgtac gcgtactact agagacgtaa cggacgatct    1500
tgcatgcatg cacatgcaat tatgcatgca cggccctaaa aacagacact cccgatacta    1560
tgtatacatg ctgcatgcgg ccaagcaacg acggtggcgt atgcatcgag ggcgtacgtc    1620
ccccggccca gcccggctgg gtccagggtc caggcggggg cagcgtgcac gtcgcggtcg    1680
cgaccatgat gccttgcctt gcctgccctc tgcatgcagc agatggtgta catgtcggcg    1740
acgggcccac ggaaaaagca gcagaaaaag cgcacgcggc gaatgaagaa gggaaaagga    1800
aacgcaggtg cgagagggag cggatgcatg gatcgaccga gccggccggg cgtgagatgc    1860
aatgagtata acgatgaagt gatgaacaca acacaccccc acccggccgc agtgatggac    1920
gacctgtacg acgcaattca gctgttcggt gcggcgtcgc cttcgggccg attcgccgga    1980
cggacacagc gcgctgcatg tacccaccca aatctagcta acgaccctcc gatccctcta    2040
gcatgcagat gcagtgcaaa gtaataagac aaaccccggg tcggtgagac gatgccacag    2100
ctagctacta gttccaatca atcagctggg agagggccgg ttctggcccg gcctcccgtg    2160
ctttgctagc tttagttttg gcatcaacga atcgtcgcca acagtcaccg acgacgacga    2220
ggaaggagga ggaggaggag aagattagaa gggtgtcatg gtatggtcca caaaggcatt    2280
atattgatgc ccatgcgtgc atgtaaactg taaagtcttc ttaaatctta acggtgtggg    2340
```

```
caatgaaagc tagctagcta gcctgctatc tactggagca gcaggcccgt gtggacggtg   2400
ggccacggac ccgacggacc aggcgcggtg caatattgcc caacgccggg cgccatggac   2460
cgacctacca acgtcgctag ctagctagct agctgctacc tatccatggg cggggtttgg   2520
cccggccgga cagggaacac gatgagatgc atgtgtgtgt gctacgcgga aacgaagaga   2580
tcgaattaag cgagatctct gtatggtgcg tgcccttggt tccgcggccc tgccgttgtt   2640
catgtacgtc atgttcacga ggatctcgca tcaggcctcc tttgctagct gtccttggtt   2700
caatggttct ggattcgtgt ggccggtctg taattcactg cactggcgag attattattg   2760
ctactggata caggcaatat gtcgagcagg ccatccagtc tgggttcatt cttggtccc    2819
```

<210> SEQ ID NO 6
<211> LENGTH: 2116
<212> TYPE: DNA
<213> ORGANISM: Zea mays

<400> SEQUENCE: 6

```
acacgaccca caaaggaaag gaatctaccc ccaggcaaag aaggcttacg gtacgggcct     60
gttagaccaa aacccctgca gcccacttgc aaaatagcac cgaagcaccg gcccatctaa    120
cgaaaccctg aggccccatc caacgaaagt agatgatgca agttcgggta cgattcggcc    180
ggcgctcctc cccttgttgg gcctgtgtct cccatcgcat cattcattca ccacatgcgg    240
cattttgatt tcagcgcagc attattttta tacatacgtt ggggggaaaaa aagtgccaaa    300
ggccgaagca gtgaaacttg aaagaaatga agagacagaa cagttggtca agtcggcaga    360
gtggcacggc acagtgttgc ggaatgaaat gaagtcggag atcctatatg ggcgggcggc    420
ggcgaggtgc ccggtcgtcg tcggccgcgc gagcagtgtc acatggcatg tttgtgttgt    480
gccggggcac atcagcaggc gaatcaatca atcaatcaat caatcagtgc gtgctctcga    540
tgacgatgga tcggcccgga cctctcacgc aatgcgaggt cccgtcctga tcacatgcgc    600
tcctagctac acagggccct gccgggttca atccacctct agctgggact gggacgggag    660
ggattaggat taggattggg attaggacta ggcaacctag ctaactgtgg taggatcgca    720
gcaactaacc ctccttcact agcgctggtc ggtgtcgttc ctgcgaagaa acgaaaccga    780
cgacagctag ctactgatga tcagagtact accacaaggg aataataatg tcgattcata    840
tatatagtac gacgcgtcgg caatctaatc atcgacgccg accggccggt ttagcacgag    900
gtatagtata tagcctctgg ctttgtctct cacacgctgc tgaggtgacg ccacatggca    960
tggagatata tatataggga acatagcaaa acagtaggca tgcatatgcc aagcgcatta   1020
tatttcgcta ccaagtgtag ttaacttgac gtgatgatct catggccggt ttagctgtta   1080
cctctctctt attatattgt acgtactccg ccatattgtt catggccgcc ggccaccagg   1140
agaatgttgt gatcatcatg catactagag cgatgataca tctgccgcta gctccttatt   1200
tctttcttca tcgacaactt ttttgttgga accgaacgcg tgttggagtt ggaccacgca   1260
gcacagcagg ggacgtttat acttgttggt aagctgttgt tagcgctaat gatgacaaac   1320
agacgagggg aagttttcgc ctgaaaacaa gctaaaacct aggagctagc tacaggtgaa   1380
tcgaactaga gtaggtaact taacttgagc cagtcagtca tgcgcgctgg gctgtgcaat   1440
gcatatgcac cgctgacaat tgtaggccca gctgacagaa aatatataga cacatttatg   1500
tgcgagtcac gtcgctagct ctggatcttg agtcgctttg aaggaggcaa ctgatcgatg   1560
tctgactctg atgctaacca tacccttgca gtgagtgtga gtacaacgta acctactaga   1620
```

```
atcacgcatc aaattaacac tcgtcgtcgt tgcctctgta ccgagtaatt gttgctgctg   1680

gcgggcttcc agttttttc attttctttt tcagatggcg gagctcacgt ccgcttccca   1740

ggtccacgca cagctcacgt ccggctcccc aatcaaccga aagctgccgc tgagctgaga   1800

ctgagacgga ggggctgacc ggtgggggcg tgcgtgatgc cctcctcctc ctcggaaaag   1860

gtgagtgggt gggtggccga gggccgaggg ccgtgcacag gctgacacag gccagttgct   1920

tttctgagct ctgcctgtct cttctgccca gatatgggac aatcctgcct ggtctcaatc   1980

ggggttgaga acatctcttt gtcgtcacca cggttactta cacttacctc ccgtggtaat   2040

taaccaggca aaagcaatta actgaaccca acgacgtgta cgtaccgtag gacagacatg   2100

tcgggagccc ggacac                                                    2116
```

<210> SEQ ID NO 7
<211> LENGTH: 1634
<212> TYPE: DNA
<213> ORGANISM: Zea mays

<400> SEQUENCE: 7

```
gacaaagtac acaatcaacc cctttgcaaa attgtgagcc attcatgcat aaaagaggaa     60

atattgctct catatctggt atctatcttt tccctccaat tacagttaaa aaggaaaaag    120

gaaacgaaac gaagaggaaa gtaatattga ctgttacaga tcttattctc cccaatgcaa    180

gtggaactac tttgtttttt cgggtcttcg tccatgcttt tttttccctc caaccatctg    240

attgttagat actgtcattt cgccattcaa tcggaatcaa tcttcaagtt gccggagcaa    300

acggcccatt ggaatcgaac gagaaccttc ggggagagag aggagctggg gaaaatgttc    360

tagctagcta gggttttgtg tgggcggacg gtgactcgcg cttgcatgca ttgcacactc    420

tccggccggc cccgaccctc tccgtggagc cctagctaga tcaagctatc gcactccggc    480

cgtcccgtga aaaagaaaaa acggtgtttg gagaacacgc agcacgtacg catcgagagt    540

cccaacacag tgacaggacc acacccccag atcatgtctc aactctcaag tagatggcca    600

caggcatgtg atgagtctgt tgcagttgaa cgatcatgtc gtagtcgtcg accgcaccgg    660

ttttaatttc ctgatgacga gctagctagc tctctgtttt cagaatcaat tatttagaca    720

tgcgtgtgct cgatctacat atatagctag ctggccgaaa aggatgaagg tttttcagcc    780

atgcatatat atgcatcagt gcctgtcgtc tccttcgcca tgcatgcatg cacaccaatg    840

aaacgcgaac aatcatttag gacgacgacg acgaggagga ggactgcatg ctgctagctg    900

cctgcctccc tgccccgaaa acgggtgcat gcctgcatgc atttgcaccc acacccactg    960

cgcaggccgc agggtcgggc acaaggtcac cagcgccgga gatggtccaa gcatgcacag   1020

cacggctatg tatcgagctg catgcatgcc agcagctgtt ggttggccac cgggatttgg   1080

tctcctcccg cgtggccatg gcatgtggtg gtctgatgtg aacagctgct gctgctggct   1140

tgttcgtagc ctattccggc tgcatccact acggaccgac gatacgcggt ccatccggcc   1200

agctacatgc agagacgaca gatcatacta gctagctagc taggggcgcc gtcgagacca   1260

taccggcctg tgtcgtgtgg cctgtgtggg gaagctgaag gatgcttcgc agccacatgc   1320

cgccattgct tggccgcgat aagcaagcca tccattcgcg gccctgtgtg ttctgcgtgt   1380

agctctcagc tccgccgcac aagcggagaa aaacaaaaga tgtggccacg attttggggg   1440

atcattttcg tggccaggca cgcctccgct gatgtggata ggtatccaag caagtgaaca   1500

aagtagtggt gggcactgca ccaggaccag gggggaagga aggaagaagg atgcatgctt   1560

ctattcaatc tttcacccat ttgccaatgc gcacgtataa ctcgcccccg cgttgcctag   1620
```

ctccctcgac gacg 1634

<210> SEQ ID NO 8
<211> LENGTH: 4840
<212> TYPE: DNA
<213> ORGANISM: Zea mays

<400> SEQUENCE: 8

```
cggttgtact tgtaaatcta gctgcttgta cgatagttat atgatgtgtt tttttatcca     60
tagcgaccac cacgacaatc tagacctagc tagtgcgact gatttttaca tcaatacatc    120
gcaaaagcta cgcacttaga gagaaaaata aacattggaa tttagagggt acagtattta    180
gcacttcgtt acagatgtgt gaaaatccgg agccgatttt gcaatagccg tggatcgctg    240
aaatcagacc ttccttgtgc tgtctaaaat aaataaatgt tttgtgttct tcgtcggaac    300
aagaacaagc accggttgct cggaccgtgg agaaaactgg ttgggctgtg ccgagaaaca    360
atgagcgggc tgggctgcgt cttgacggcg ggccaccaaa ctgtcccgcc gtgcgcgcag    420
ggcaacaacc acaacgtcat gtgcggcttg cttaactggg cccgttagac gcgggcttcg    480
tgtggccttg gaacacggcc gttcgacctg gcttcacgtg acgtgaacca gagcggagcg    540
gggccatcga tttcggccgc gcgaaacgcg tgcgcgaggc ctgcgaaagg ccgctggatg    600
aagctccctt tgattgaagc ccgtgtgggc cgcaccgcat ggtccggccg gcgatcgtga    660
ccgttggagt acgatttatt cgatgcgtat gtactcagct cgatccatat acgatatgat    720
agtacgtaga catcttagac gtaagttgtt taaggaactc tctctctctc tctctctctc    780
tctcgggttt ctgtgttcat ctcaaagttt tttcagttca aaaaccaatt cgaaaacaaa    840
tcggcttaaa attcaggtaa tcaggtcaag cgactttact ctggtctgaa taacttgaga    900
catccgggtt gccatggccg actctagaca gcggccataa acacggtggt ttctttttct    960
tattgggata gtaggtcact ccaaataaag gctattgcca tatgctaagg agacggaatt   1020
tgtgacgcca tcgccaccgg gttaacgtta atattctact actagagaat ctagcttacg   1080
tttcggttcc ggccggccag tagaaaactc tctctgaacc gaccggtcag aatcccctgc   1140
tcggtgctcg gttgcttgga ccgcacgcac gcacccctat atcgtcagtg cctgtaacag   1200
ttcttattcg gtgattatta ttataatatt attccacgtt tgcacacacc gcacatccgc   1260
ccgtttgtaa aactgtgagt tgatcgtcga gacgaaaggt ggagctggag tatatggctg   1320
ggcttcgatt gccgctcgca ggtcggtgtc ggtcccgaac ttttttactc gcgctccatc   1380
accacatagc ctggcgatcc tatcgtctgc ctacggggcc gcagcggcgc tcctccatct   1440
cctgggtctc gttgtagcca catatagagt agtagattgt tcgtcctcgc aatgatccgt   1500
agtgcacaat gcccagtcga atagtcgatg aatagcacat acacatatat gcgtgtgtgt   1560
ggtcttgtca aggttaactg ctgcagagat gagatgccaa agaaaaaaca catattctaa   1620
ttaataaagc tttgtgtgcc gcgacaagct agctaggcta ctgtctcgta cgttcacgcg   1680
gtctaaatca cgggcgcagc acaaattcga tggcagcctg gactaaacga ggccgtggcc   1740
gtcgtcacca ttcaccgatc cacaggattc acccgggggc aaaaccagcg cacattacct   1800
ttgcaggaca ggagttagag gcgccttttt cctggtccct ctctctgctg agcacatgca   1860
gcagctagct agctcacgct actagtcact cgcgaagaac gaatccccgg ccggcgccac   1920
tagttgtggc tagctctcgc gtctttacat tcgcagctgc agcgtccatt tcacaggcag   1980
tatacatgca tgtgatcgag tggaaggagg agaggccacc gctggccgct gcccgctgct   2040
```

-continued

```
tttcacgtac aggcgccggc agtgcaattt ggcgacgatg cgaggtgttc gccagtatgt   2100
ctcgctgaaa gggtgaagcc ggagaaaggg ggaagaatgt ttgctgcggc ggatggagat   2160
aagatcgcat ctcgatggga attagaacgg ccgccggccg agtgtgtgtg tgtggactgt   2220
ggatcgaaca ttccgccgcg cgcctgaaag gactgtcgaa gcattgtgac atctgtcagt   2280
cgatcgatcg tgtggttaac ttaacggatg ctaaccctag cttctttttt ctcttcagtc   2340
tagctagctt tctatcttgg gagacaggga cagcattttt ctttttgttt ttttagtggt   2400
acctttaatt ttgctggtgt cggttgtact tgtaaatcta gctgcttgta cgatagttat   2460
atgatgtgtt tttttatcca tagcgaccac cacgacaatc tagacctagc tagtgcgact   2520
gatttttaca tcaatacatc gcaaaagcta cgcacttaga gagaaaaata aacattggaa   2580
tttagagggt acagtattta gcacttcgtt acagatgtgt gaaaatccgg agccgatttt   2640
gcaatagccg tggatcgctg aaatcagacc ttccttgtgc tgtctaaaat aaataaatgt   2700
tttgtgttct tcgtcggaac aagaacaagc accggttgct cggaccgtgg agaaaactgg   2760
ttgggctgtg ccgagaaaca atgagcgggc tgggctgcgt cttgacggcg ggccaccaaa   2820
ctgtcccgcc gtgcgcgcag ggcaacaacc acaacgtcat gtgcggcttg cttaactggg   2880
cccgttagac gcgggcttcg tgtggccttg gaacacggcc gttcgacctg gcttcacgtg   2940
acgtgaacca gagcggagcg gggccatcga tttcggccgc gcgaaacgcg tgcgcgaggc   3000
ctgcgaaagg ccgctggatg aagctccctt tgattgaagc ccgtgtgggc cgcaccgcat   3060
ggtccggccg gcgatcgtga ccgttggagt acgatttatt cgatgcgtat gtactcagct   3120
cgatccatat acgatatgat agtacgtaga catcttagac gtaagttgtt taaggaactc   3180
tctctctctc tctctctctc tctcgggttt ctgtgttcat ctcaaagttt tttcagttca   3240
aaaaccaatt cgaaaacaaa tcggcttaaa attcaggtaa tcaggtcaag cgactttact   3300
ctggtctgaa taacttgaga catccgggtt gccatggccg actctagaca gcggccataa   3360
acacggtggt ttctttttct tattgggata gtaggtcact ccaaataaag gctattgcca   3420
tatgctaagg agacggaatt tgtgacgcca tcgccaccgg gttaacgtta atattctact   3480
actagagaat ctagcttacg tttcggttcc ggccggccag tagaaaactc tctctgaacc   3540
gaccggtcag aatcccctgc tcggtgctcg gttgcttgga ccgcacgcac gcacccctat   3600
atcgtcagtg cctgtaacag ttcttattcg gtgattatta ttataatatt attccacgtt   3660
tgcacacacc gcacatccgc ccgtttgtaa aactgtgagt tgatcgtcga gacgaaaggt   3720
ggagctggag tatatggctg ggcttcgatt gccgctcgca ggtcggtgtc ggtcccgaac   3780
tttttactc gcgctccatc accacatagc ctggcgatcc tatcgtctgc ctacggggcc   3840
gcagcggcgc tcctccatct cctgggtctc gttgtagcca catatagagt agtagattgt   3900
tcgtcctcgc aatgatccgt agtgcacaat gcccagtcga atagtcgatg aatagcacat   3960
acacatatat gcgtgtgtgt ggtcttgtca aggttaactg ctgcagagat gagatgccaa   4020
agaaaaaaca catattctaa ttaataaagc tttgtgtgcc gcgacaagct agctaggcta   4080
ctgtctcgta cgttcacgcg gtctaaatca cgggcgcagc acaaattcga tggcagcctg   4140
gactaaacga ggccgtggcc gtcgtcacca ttcaccgatc cacaggattc acccgggggc   4200
aaaaccagcg cacattacct ttgcaggaca ggagttagag gcgccttttt cctggtccct   4260
ctctctgctg agcacatgca gcagctagct agctcacgct actagtcact cgcgaagaac   4320
gaatccccgg ccggcgccac tagttgtggc tagctctcgc gtctttacat tcgcagctgc   4380
agcgtccatt tcacaggcag tatacatgca tgtgatcgag tggaaggagg agaggccacc   4440
```

```
gctggccgct gcccgctgct tttcacgtac aggcgccggc agtgcaattt ggcgacgatg   4500

cgaggtgttc gccagtatgt ctcgctgaaa gggtgaagcc ggagaaaggg ggaagaatgt   4560

ttgctgcggc ggatggagat aagatcgcat ctcgatggga attagaacgg ccgccggccg   4620

agtgtgtgtg tgtggactgt ggatcgaaca ttccgccgcg cgcctgaaag gactgtcgaa   4680

gcattgtgac atctgtcagt cgatcgatcg tgtggttaac ttaacggatg ctaaccctag   4740

cttctttttt ctcttcagtc tagctagctt tctatcttgg gagacaggga cagcattttt   4800

ctttttgttt ttttagtggt acctttaatt ttgctggtgt                         4840


<210> SEQ ID NO 9
<211> LENGTH: 1726
<212> TYPE: DNA
<213> ORGANISM: Zea mays

<400> SEQUENCE: 9

gcggctagtg gatcgatcac acatgtttcg aactatcttc ttttccctgt atgaggtaca     60

gtagtagctt acggacgaag ggatagatag atatatacat accatgtgct atgcgcgtct    120

cacttgtgta cctacagcta cagatgtgca tctctatcct atctcttcac tctggccacc    180

ttttcttcta gctcggaagg aaaaaaaaag catgtattat tgcatcactt ttttttgca     240

agggatacgg tgcagcagta ctactactgc gacgcgaatg ttcattcacg ccgcgtacgc    300

gataggcacc gctgcatgta cccaccggca cagtactaac ggtttagatg tctactactt    360

attaattcaa tcacgcgtct gcgagaaagc aagccgacgg gcatcttctg cccgagtctc    420

tccgcgtttc tgtaactaga attgtcatag tcagggttgc caaacatcag catcccgagg    480

cagtttcttt aattctgctt ttttttatat atgtaagttt gcttaccgaa tgagctagtt    540

ctaaacaaac tcaaaaacaa aacagggcaa ctgggggtcc cttgacattg cacagatgga    600

cctgaccact ttgagattcc cccggcttct atctcctttt ccctcccctt ggatcaaatg    660

aacaaaggag cgcattctct ctctctctct ctctctaaaa gattaaaaaa aagcctgcat    720

gtagtgttct ttgacaagga caaggaagcc cttttacatc aatacatcat tcgtatgttg    780

ttgttttctg tgttctttgc gttccttttt ttcccctccc tccgcctttt ttctacttga    840

ttgttgccaa gatctggagc acctgctctg atctgattgt gtgcgctggt ttactgaacc    900

tttcggaggg ctatacgctt cgtacgggga cataccaatt tcaaagaatt cagtcatcag    960

gtaggtggtt caatcatacc gatggtttcc tcactgcatc actcaccttc tcatttttac   1020

gcatcataat tttttgttcc cttctcctta attcccatgc ggtgaaggag agatgtgaac   1080

taacagtttg gcgctgcact gttcgaccgg ctaaacacgg ggccaatgct ctctgtacgt   1140

gcagatggat aggatagtct ttgattcttg tttcaagatg acgtggatag tctataatag   1200

ctaaatgttt gcctcgacta ctaacttgcc gatatgggcg agggtaactt taaattaaat   1260

ttttaaagca tttgacttgt taaaaaaaat aaaagcctat attctttgtt gatggaggga   1320

gcaagtggct gaaaagccgt tgccatttct gggcgctccc taaactacgc ggcaagcagg   1380

ctattgggag cccttgtcgc tgtcgacgcg atgtgcggcc tctttcttcg tcctcttggt   1440

taggtcttat ctacatggtc acgcatccag tttattcatt aggtacgcta actgtgtgat   1500

cgtatgttca gtttaattta tatgtgttag agtataaaaa aatttatgta aattttacat   1560

tagcttgagt cagtcagtca gagcaaatta atttagcggc tagaccgcta gaggctagtc   1620

gcgtgcgtgc gtcgctgata ctcaccgtca gtccgtcacc gacacttggc ctgggcggcg   1680
```

```
tgtagcagca gcacggatac gggcaatacg gccgggtgca tggtct                1726


<210> SEQ ID NO 10
<211> LENGTH: 1923
<212> TYPE: DNA
<213> ORGANISM: Zea mays

<400> SEQUENCE: 10

cggggccata ggaggttact aggtttcatg gccacgggag ctatggttcc gccatcacag      60

gccccaagac aagtattcca gatcaaaaca tataaatatg ttttgatttg acggcagcca     120

aaagtactgc gacgacgtac gtacgtacac taaaccgatg taaaaccgta ctacgcgctc     180

atgttcggcg gccggatcca cgcagaagtt tgacgagcga attaacagag gcagagctcc     240

ggatgatcag tctcacttac ctcccagttc tcaacagcct cgtctgtagc caagtcagaa     300

tatatatgag tgtgtgccac tgccgacaca tgcatatgag ctattgagct cgacagggga     360

aattaaagag agagaaaatg ctacagtagt ggaaactgct cctgatgaga ccggccggcc     420

ggaccagatc gaccttgcaa gagcggagag gacggccggc cggtcgcagc tagcgctgga     480

tctcgggagg acaacgggca ctgtggcgtg cacatgcatg tgcgatcgaa agaagcttgc     540

gatggtgtaa atagtgaggt cccagctgtt cacagtgcat taatttgtgc ggccggcgag     600

cgacgacgag cggtggcggt gcagagaacc gacgacgagc ggaacagttt ggtcagccaa     660

ctctttggac ctgcatgcta tgctaatgta atgaatcgaa ctgatgagtg cgcggcggca     720

cctgtgcaga cgagtactac tactctacag tggttcatgg tcaccgtgct gctgtgtgcc     780

tgtgcaccgc gaccgacgac gacgccgcga ttcgctcgtg cacgcgagag ccagtcagcc     840

actgccgccc ttgcgcatga tgcggtcggt gaacctagct agctagctag tcggcgcctg     900

ccctatgcat gcggatgcag gacacccaca catgtgacag cggcatccgg cagcgctgct     960

ccatccacaa cctgcagctg ccgatctggc atcattacca agagagagag agagctgggg    1020

atggattatg gatatgccaa agcttctagc gcaacgaacc gacacagaca cagtgctctc    1080

gtacggttgg tgagacggct ggctggcatg gcatggcatg gcacacccca tgcatgtgga    1140

cagtggactg gggggagagg agaggaggtt accgatggat gtcggttttg cagaatcatc    1200

ctctactaat atagtaacta gggatccgca cccgcgccct ctattacctg aggcacgacg    1260

ctgcgtggat ccgatcatgt gggccgcagc cagctctggc atttggatcg cagcacgatc    1320

tttaccgagc aaaaacaaaa ttattacagc cgcgactgcg atgtactact agtactcaac    1380

ggcaccacgg ccgttctcgc tcactcgtcg cccacgccga ggccaccacc gtgtagcata    1440

gcaatcagtg acgagctgac aattggggcc gtgctgtcac gtgggccact tctctccgat    1500

tctctaccac tcttttgttt ccgcatggtc taagtggacc ccatcgcctg gcgattcttt    1560

ttttccttct ttactttata ataattccct cgtcccgtgg tcgcgaggat agacagacgg    1620

atggaggaag acggcgacgg gagatgcaga tgcgtcacgc gtgtgctgtg ccgtgcggtg    1680

cctttcgggg aatttgtgcc gcgccaaagg ggagcctcgt ggggccccga ggcctgccgc    1740

ggacccaccg gggctcacca aaagctggct ggatattgct tggcaaaaag gacaccaaaa    1800

gaaaacggga aagggttggc cgtaaataat tggcacacgc agcatatgca cacagcttct    1860

tcaaaagaac aatataagta ggcgttagag atccatacga ctatacctat tgctgtccat    1920

att                                                                  1923


<210> SEQ ID NO 11
<211> LENGTH: 1660
```

<212> TYPE: DNA
<213> ORGANISM: Zea mays

<400> SEQUENCE: 11

```
ttagaatttg ctatgcaata aatatttaaa aaggtgcata taagagagaa aaacatggat      60
atagtgacga gattactctt gttaggtgtt ccttgaacat ctaccctagt caaagtaaaa     120
tcccttacca cccttcttat gggatcacac aaatgatggg aatttatacc caaaaattcc     180
atgaaatatg caatagaata aaagaacgtg gcacaaattt gacatgtttg agatataaag     240
ttatcatcaa tctatagtag ccaaaacaag gacaaacaaa aaagtttaag gaattaatta     300
ggactcaaac atataggaat tgaaacacag acatgacaat agcaaataga aatcaacaat     360
tatgtaagtt tttaacacat aaaaatcaaa caatggttat agacttgtag ttctccaatc     420
tctagttttt cattgattag caatgcaaag gttgtatggg acaaaaactc aacataatcc     480
ataggcatca agtttactat ggtatataag accagcaaaa ctaagataat attatggtcg     540
catatcactc attataaaca agggtacata aaagagtaca ttctaaacgt ttttacaata     600
ttgcatgcat ttgcttattg cactagtagg gacaaaaaag acttctagtc agagaggagc     660
caacaacaat gccctttgag gtggttaaaa cctagagggt gaagaagggc ttctttggcc     720
atcaatgaag cattataaaa tcatggaacc acttgttact caatctctca ctatttgtct     780
attcgatgtg tgatgaagtg ttgatgatac attgtgtgtt ggcacatggg cttgtgttct     840
actcattacg taggccatgt gataggatga gtagtggcta actcgacaag tggtgaccaa     900
gtgaggtagg gttacatagt ttttatatat atgatattat ttgggcatac attataccta     960
tattattggg attattttgg tcagaatttg aaatgcattc tataatgttc gaaggcccta    1020
acgggtaacc aagaagggta cataggaaac atgttgattg taatgtattc gatatccttc    1080
taaaatttgg ccataaagcc ctttataggg agtgaaaaca acacatcaat gtctcgtaac    1140
ggagaaatcc ctattattta taagggattg ggccccattt ccatgcctac ggaatgctta    1200
tattacaagt gcactctaga aacgtaactt gcacatggat gacatgatca agactcgtcg    1260
catgtgatac aattaccttt tctactccac attcttattt gacttttgtc tctagtattt    1320
tttgtttgtc ctagacaccc catcagtaga gtccacctcc ttgtcaatga accttaacta    1380
cccaccacca aaaaatccct ctttctactt tcattatatt ggtataattg ctatagctat    1440
cttgttagtt gcaaaaagac tagtcccatt gccttactag tgaccctaat ggagggctac    1500
atatccttgg tagatgtgga ggtaccaatg gttccatcac atccattaga ttaggaggac    1560
accatgatag gcactagtct caacattaac catagttctt gttttttctt ttaaaatcga    1620
aagcattatt ttgttttaaa ttcttttagt cgaaataaac                          1660
```

<210> SEQ ID NO 12
<211> LENGTH: 1552
<212> TYPE: DNA
<213> ORGANISM: Zea mays

<400> SEQUENCE: 12

```
atatatatat aggacagcgg aagtagtgcc gtacgtgtgc aaaaagactc cctacgctag      60
ctagctagct agctagctat atatatgcgt gcattttgta gggatcggag agcttgtcat     120
tgcgtggtat atgttcgttc acgcagtggc cctggccgtg tatatatagc tagagctagt     180
gacctttcag tgtttcatct agtcacccct atcgtctatc ctcattggag cctagcgcgc     240
gcgggcgcgg tgacaggagg ccgatccggc ggtcgacgac gggcgagagg gacgagatcg     300
```

```
gatccaagac acacaaaaaa aaggtaggca gcgaccgacc ctagctatgt atcctacgac    360
gtgcgtgcat gcaatggtga tccatcctgc agtacgcttg cgtgcagtgt gtcgcctcgc    420
ctgatctata gccaccacac gcacacacac atcgatctct acgaccgagc tgacgctgtc    480
gtcgtcgctt actaccactt gacttactac actgccgtag gaaaggcctg cgccgtacgt    540
acatgctcac gctgccctgc tggtgcctgg tggtggtggt ggtgtggtgt gtgtcgatcg    600
tgtgtgcatg catgctggca tgctgccgtc ccagcgcccg gccggtcacg cgcgccaaca    660
gccaacgcta agtatgtagt ggccgtggtc gatgctgtgg taaacaagcc atgcactacc    720
accaccagct agcgtcatgt atctcatata tatctcaact gagcatgatg cgtgtataca    780
gtatataagc aggctagctg cacctgcact cggaagaaca actgcatgtg cgtacgtact    840
agcagataga atagctagca gctagctaga accgtgtgac gtgttgtgat ttgaccgatg    900
gcaaattaaa aggtgctcta atccgttatc tgtccatatg tatatgtgga atccgacgac    960
acacacggcg atcgagagtg atccatgagt ggccgacgtg tattacacac atcttatata   1020
ttagcttatt aactgtgtcg tcttgtgatg tcagctacta ggtgccgccg tgccgcagta   1080
tgtagctagc tcgtcaccaa ccctcacccc ggcccctata tatatctttg aattatatat   1140
gtatgtatgt atagtatgtt ttctcaagct caaaatatat atagttgatg ttatacgatt   1200
caaatattgt ctcaaagcag ttattacttt ggctcaaata tttttctcta cctctctttt   1260
tctcgttgtt ttacgttgca catgtttttt agaataaaag aagtatatat agctttacaa   1320
gtaagtatgt ttaaccaaaa gaagaaaaag ctaagcgcat atgtcgtcgt tgaccgcaat   1380
aaccagcacg gaaaattcta acaaaccgcc cgacagggtc aggacgtcag gtcacatcga   1440
cgatctgctg gttggaagaa acatatggac atggagcccg tacgggccgg ggggagaaat   1500
cagatacgcc acgcagacgc accaccattc atgcgtttgt atatgctagc ta           1552
```

```
<210> SEQ ID NO 13
<211> LENGTH: 1636
<212> TYPE: DNA
<213> ORGANISM: Zea mays

<400> SEQUENCE: 13

gcggtagtag tagccggtgt ttggttgcta gccacacact tttgtgtaaa gtaagtcgat     60
caagttggtg agtacttggt tggttggata ttaaacttgg gtaatagtct ttatagctcg    120
ctagctagct ccaagtatat catagagtaa aaagcgtgac aaaattgagt gattcatccc    180
ttgagcttgc attgcttgct caattgacta ctcaccagag ctctcaggca tctctctagg    240
gatgatgttg cgcatcccct ccgtaaatga cggcgccccc tcccgagcag gcctgccttc    300
agtggcggct accttcttgt tggaggtctc gtctctctct ctcgagcggt atgcagtatg    360
ctccccgtcg actctgctgt ctgctcgcag tccattcgtg caggcagaac cctaccgcta    420
tactagaagt aggtagtagc cccgcctccg acatggaccg gaagacccgc tcccatgcac    480
tcctcaccgt gtcccgtacc tagaagacgg gatggaggag aaagacgtga aggagagacg    540
agtgtgtaac acttttttttt tggggggtgg gcacattaat gtgtgtacat gagcgaccga    600
gaccagtact acaagtctct cgttcgtctt ctctccatcg atcgaaacat gccgcaccgt    660
cttcagtagt tctctctgct ggcgaaaggg catgcatgca tgtgcggaaa ctatactaga    720
acattaacaa actaacaaat ataatcggtg gtctgtgtat aatctaaccg tagctatata    780
gcaagcagtg tgggtgtggg cagctgctgg tgtgcggcgt gagaaatata ggagggggac    840
ggatcggacc agaacacaac agtcgaagaa cacggggaac agtgcgcgcg gtgggtggcg    900
```

```
cggcaacagt agtgctagtg ccggccccgg tccccatccg atgtgaccga ccgctactac    960

taccagcttg cattgcgtcg acgacgcatt gcttgggccg cgcgcgcgtg tatgtgtgtc   1020

cctgtcacct gtcgccacca gatcggctcg ccggccgccc gctaccgaga tgaaagtaca   1080

gtacgttgga cgagcgcgca cgctggcttt gcccacgacc acgagcagtg cagtgtgcaa   1140

acctatctat ccaagcacag tatagctact acatatacga tcgatctagc tagctagggc   1200

gactgtagcc ccaatgtacg tacaatatac gtacgtacgt gcacgctgct tcgtgtcaaa   1260

aaaaaggcca ctgtacctac ctcacgaagt actataagga cctgtcatgt ccttatatga   1320

gacatcatag taccgtacca aagtatgtac acgcggtgca ccggatcgtc tcaggtctct   1380

atcaagcgaa ggccgagatt ggtgtggata ccaaatcgaa aacatgcagt acatttgtcg   1440

tcagcaggct atgcccagca gcacactcat cctacgcatc gatctgcgtc taactattca   1500

ccttccagcc ccaccgtgga tgacattgtg caaaatgagc gctcgacgta cgtaccccat   1560

ttctttggct ttctctctgt ctcctacgac tgtgtatgcg tatctgctga gatagagcgg   1620

tcactttcct cgggct                                                   1636
```

<210> SEQ ID NO 14
<211> LENGTH: 1584
<212> TYPE: DNA
<213> ORGANISM: Zea mays

<400> SEQUENCE: 14

```
ggtactgatt acctaggaaa ataatcttgt tgagggtcta gctggtaacc tggttgataa     60

gggggtggct attctactct attctgatga caaatttgtg aattaaagat gacttataca    120

ttgctagaaa catgaatctt gttgtatatt taaataatgc tatttggacc aaagattaac    180

ttcactaata ttgaggaccc gatgattaat gataataatg aaaatttaaa cacatgctga    240

tgtttaattg tcaagtgagt atgttcccca caaagtatct tggggtcccc aacagactct    300

acatcattga ctggctacac gtctatgaga aatctaccaa aaaattagat gcattggcat    360

gctagttccc taacaatggt ggaagaggtg ttttgattaa atccaatttg aataatcctg    420

ttatatatca aatgtctata tttatcttac tccaaaccat cattgataag attgataaat    480

agagaagatc attgctttag taatgaggga ggtttactag cttataatag aaaatgttat    540

ctattcaaat ggactaagta gggaaaagtg ccaagaaagg aggtttaaga attataaatt    600

tcaagcaaat agatattttc ttagtaaata attggtggta taaattagta aatatgtagg    660

ggcattaaac aggaaagtac tcatcctaag tatattagaa ctttgtgaat ttggaaaatc    720

aagcatatac atgatgattc tcgaatatgg acagatttac taattttaaa ttaggcatgg    780

aaaattcaag tcaataatgg aaagggacca tattttagct tgatgcttag caaggaaaat    840

ttcccctcca tcgtcaacac cctgttctat ttgtactttg taatgaaaaa accagtgttt    900

aggtttaaac atgtaaatgg tactcaagga aaaaggtagt gacatccaag ctgggctccc    960

atccccttgc tatgtgattt ttttgagtta ataacttata tgcatgcaag gattgcaatc   1020

atatatttca ttctccatat tagttgcata tttctagtca tagcaattgt gaaggtttct   1080

taatgtactt tgactatgtg ctcatgtaaa tttactccct acttcattca cccttgggca   1140

ctgatgtacc ctaaacttga tatgatggtc caaacttctc tttgggagaa atggaatgaa   1200

gttcaatatc attccctata gagcattgcc ttcgccatgc ttaggccatg gatcctcctc   1260

tagtggccct ctaggatgaa attcatgttc aataataggt cttactatgg tctataattg   1320
```

```
atggcatagt cgccttcgac tccaagctcc actatgtgcc aacatcaccc ttcctacaca   1380

agcagatgtt catcatctat gatgatatac attagggcat acaatgcatg ctttacaggc   1440

ttcgctaaga cttccacatg cctaaccttc ataatgtggt ccatgagttt atttgcaatt   1500

gctccatgtt aaatcaatac aataccaaac acattcgcgt acatggggat cttaatgtca   1560

ttgcgtattt cgatggtggt ttga                                          1584
```

<210> SEQ ID NO 15
<211> LENGTH: 1776
<212> TYPE: DNA
<213> ORGANISM: Zea mays

<400> SEQUENCE: 15

```
tgcggctgat ggtgtaaggt gctaaacagt aaacactgta gctgcaacgc tgctagaaca     60

ggcagtggag cttggatcac cttgctgtca ttttggttac gacttaagcg attgtctatt    120

ttgtcaacat gctttaatct tatatgctct tttccttgga aatttgcagc ttgtatctga    180

cattcatgta gccccagttg gcactgttct cgctcagggc atgaactcaa agaagaagca    240

cgaagtaggt aattcggctt catactgatt gttgaacttt ctatgtcctc tttttttcc     300

tgcaaatatg ttgttatttg aactctcatg tttgaagaaa ttgctttatt cagattgaaa    360

atctagctgc tgtggttcat gcaattgcaa agaggtgtgg agccaagaca gtggttgatg    420

taggttctgg ccaggtatgt catatgcatg ctagcatctg tgcaattgta accagattcc    480

tagtagtcat aattttcttt ctaatacttg gacagttggc atccctcttt attccttttg    540

gttgtgatta tgccatctta aatgttaggt ttatgcattc atcaccaatc ccgagcaaga    600

atgccccaat cgatccagct aaatatactg cccccgagga aaagcaatat actgtgcttt    660

atacatgtcc atatttcata aactatgcct ttatcgcatg atactcttga agtctggatg    720

ctaagagtcc aaattatgga ctgttttact catctttaaa tagtcagaac ctacaaagaa    780

catgttctac atggtctggt ctgttatttt gttgacttaa ttgcaagctg caaacaaatg    840

aacaagtcaa gctatctggt ttttgttgta gacattgcat ggcaatgcct tatttttat     900

gttgctgtta aatgaaagaa atgattgaat ttaacctagt atcagcagta acgtgttgtg    960

tcatgcattt atcttatttc ccatcttatt tgattatcag ggttatctcg cacaggcctt   1020

atcttttgag taccaactcc gtgttgtagc aatagatgct tcatcacacc atgcatcagt   1080

tacaattgct cgtgcagaaa gaataaagaa gcactatgct gctaaatggt gcaaccttca   1140

tcaagtttaa tttgagttct actacctttg gattcctatc taatggtata aattgtgcct   1200

attattttg ttagtgtgga gaagcaactg ctcatggtac ctagggcagt cacctgtcat    1260

gttctttcta gtgacacatt ggcagcagtc acattagatg catgtaagga tgacaatgga   1320

gaacatgtga gagatactaa aacatctact aagaaaatca ctcaaatcca ggaatcaact   1380

cagggcaccc ctccattaat cctggctggt cttcatgcat gtggtgatct ttcagttaac   1440

atgctaaggt tggtatttgc gaagttgaga acatggccat ggagcatggt cctttctcca   1500

agctcgctaa atgttgcata ttgaatataa gtattttcca ccttggtgaa agtccttcaa   1560

atattacatt ctttttaca gagtttttgt gtcctgtgaa caagtaaaag cattggtaag    1620

cattggctgc tgttacaact tgctttctga ggatacttat gaggacacag atacctgccc   1680

tggttttcct atgagcaagg ctgccaaaca ttctgaattg gtacttggga aaagcatccg   1740

tgaccttgca tgtcaggtat gatagcagtt catgat                             1776
```

```
<210> SEQ ID NO 16
<211> LENGTH: 2025
<212> TYPE: DNA
<213> ORGANISM: Zea mays

<400> SEQUENCE: 16

ccatggcatt gtcatcacga tttgattaac ttattcctac tctactaaga caaaatctct      60

tgaaattctt taatcctacc cctcaatgct cacctgcagt gaccccacct cccacgcccg     120

tggtcatttc cacacgtgac tcccctccct tacctctcga cctccaccct tgttctccct     180

tcacagactc cattgtcgcc accggccttc accacctaga agtggcaatg caaagtgcgg     240

cctcacctac ggttgtcgag gttcgggtga atgagcacct tccacaacgt agatggtgca     300

aggaaggcgt gttgttgggc atgcaagcgg tggtggcatg tggcctctca acgctacgac     360

acaggaggtg agaacgtcgg aatcaccggc ctcaaccctt aaaggcatgt gtctaagatg     420

aagcacatgg atgagcttag catggcccac taggctagct atgttgtgtc ggtccgatac     480

gtaacggatt gtgccttagt gggcctaggc ccgtgctagg cttggcgccg tttggtcatc     540

catatatagt cacaaccaaa ggaacatacg aaagatacct attttttttt cttttgtttt     600

ataatcacta aatgtgtaac aaagatagag gtggcattat gtgaacttgt gagatgaaaa     660

ctactgccac tttctactag catggaaatg catccaaatg ctctccatgc atgtgagatg     720

ccaaattggc aatgcagttg aacctatcat tgttagaatt agattctcct tgagtgagga     780

taggggggaa aaagggcgtc ctaatcgctt gtgattccga tgaatatata aagtcgctcg     840

gtcgtcatgc aaagtgcgca aggaatgctc tttaaggtac attactctac cctcctttat     900

cttttttttt cctatcagct gaatgtcctc tggatcggca agaatgttcg gtcttgatgc     960

tagactagaa ggctggctgg atcgccctgc aatctttctc tctcgaggat tgcatgatcc    1020

gagcttctct ggcgctcctt tttataattc gacacgaatt tggcttgcaa tcatttctgc    1080

gttattcttg ctttcggtta ttttttttgt ttctcctcat ctgatacttt gcatatccac    1140

atcactttat tctgcggttt gctttattct tataggctaa aatctcattt cagtggcctt    1200

ttggtgccat cctttttggt cccttgctga ttcgtttctt agtgtcttgg aattgtagct    1260

gatcgatgct ggtatcctga tgaccaagaa tatatatatg acactgataa atgattggga    1320

aaaaaaaggg gtccatggag gaggtcagta tgataaaaaa aatagtgctc agaagaatat    1380

atatatgtta gaagaaaagt tgccatcgtt cccaaagttc attaattttt ttgttaccgt    1440

caataatctt attattaaga gtaagaagta tattattggc tgtatgaaag ttatactgct    1500

agattttgtt tttgcctaga aatgctttaa cagaagtaac ttttttttca ccaaattaca    1560

tctgcaacga catcgttaaa aaatgagaag aattaagaat agaaagatgt ttgaaaatca    1620

ctccaggtca cctcggacaa aaaacctgcg cctttggatg catagacggc tctggtcccg    1680

ctggaccacc tgatcaggag gtgtgccccg cttgagagag atcagagatg cggcaaagag    1740

tgcatgcatg cacgcaccat ttgactctct ctcccctctc tctctctttt cattgtaatt    1800

ccaatactac tatggagtac tatttattat tatgtgtcta tgttactgcc tgactgaatt    1860

ttcacactgt agcagttcca agattggagc ctcaaaagat gagcttcttc ctccaacatt    1920

atcgccaacg ccaatcatgt gtgcgtccta catatgtcga gtgttttgcc cagcgcgacc    1980

aggatttctg tagccatgca gggattgacc tagggaagaa agtga                    2025


<210> SEQ ID NO 17
<211> LENGTH: 2103
<212> TYPE: DNA
```

<213> ORGANISM: Zea mays

<400> SEQUENCE: 17

```
agaatgagag tacactcatc atgcatgcgc tttcatacgt aacagtacat tggatgctca     60
aacgctctac acgtgtgggc cggtgcaccg ggtacgtact cggtgcagtg cacatatata    120
tacgtgtgtg tcggggccag ggccgggccc ggggccttgg ttgctgtctg tagtagttca    180
tgtaggtgtg tgtgttcttg tgtggggctg gcatgcaaat ggtttggtgc ccgacggtcg    240
aggcgatcca tgtccatatg gccatgatat acagtacagt atggctgtaa agccgaagac    300
aaaagcctcg catcgggcag aggacgacaa agagctggcc tgtacctgta ctgtacgtac    360
ttgctggccg gccgggccga aaccacgtcc atccaccatc tccattcccc ccgtcgctcc    420
tgcggcctgc cgcctgcctg ccacgctgcc aggtccagct gccagcgcca gcggccagct    480
caccaccttc ttgcccctca cttttcagtt ttcaccattc accggcggac tcccttggcc    540
ctcgggctgc ctgcctgtct agtgtctact acaggagtga ctagcagtgc gagaggccga    600
gagcagtgct cgtgctctga gcaccacgta cacgtacagt agtggcacgt gccaatgcca    660
gctgccatcg atcttgagcc gtgtgttttc cagcaaggat tccggcaggc tccaggcgag    720
accagagtac cagaccacca catgcgatgc aagccggctt gggagtgcgc gcccgcgtag    780
acacggaagg ggggaacggg gatcccagtt cgaggttcct gtctccccgg ccccgcaagc    840
ccaacaaatg gccgaataca taccatgcgc cacgtggagc ggtggtgcgg cacagctgga    900
tccctggcga cgagacgaag acgagaccgt ccgtcttgac cgcctactgt actgtacttg    960
ggctgcgtgc gagcttgcag gctgcacgca gctgccgcct gcctgcctgt ctttctttct   1020
gtactctgca gctctgcctc aaccgctcga ccgaacgcca cagtgacact ggcagcacgg   1080
acgcgccagg acgaacggac ccaacacagt gtgccagtgt ggtctggccg tacgtttgtt   1140
tgttactgtt gcgatcccga tcgtccacgg caacgacgac acgccgacga ctttcggcca   1200
tccatccgat ccgacccctg cctctgcgag ctgtaattaa actcctcggc ggtagtacgg   1260
tgcaccgccc gccgccccga ccccaattcc cgcacgcggc cgacggtttc cgggcagggc   1320
agaacaggag ccgccgcatg caccatccat cctagccgta gcccgccgct ctcggctccc   1380
cctcccaacg acctgccgct gttcctcctc tggctgcctg gtgcctgccc gccagcgcca   1440
ggagacgaga ccacgctcct ccaccacccc ttccacgtgc tccctccttt ccttgccttt   1500
cctctcctct cctctgcgtg gactggacac tgggctgccc tgcgcaactc cctcctggac   1560
gtaccttaaa accctaccct tttcccctgc tgctcgtgtt gaccactacc gcctgttccc   1620
agcaggtcac tccctcagac cctcactcag acactcatct ttctttgcct gatccggccg   1680
ttacctcttg ctacttcctt tccctttttt tcggccccaa tgcgaacgaa cggctcccat   1740
tcccttcttc tttttgtaga cagacagaca gagagagaga gagttttcgc gccgttgcgt   1800
gacggctgac ggggtgtgag gcgccgattg ttctttcgcg cggtaggatt acacgcgcca   1860
atcaatcatc cgcgtgtgca atactatact gctactacca gtaataaaca ggcaggaaaa   1920
gccaacgcac ctgcctgcct ggcctgctgg ctgctgctca aatttctgcc ggcgccgctt   1980
cggcgtggat gaggatgagg aggagggagg aaggactact ggagtaggta gtgggaagct   2040
gacgtggcgg ggtggtgcag cgccggaagc ggcatctcga ggggcgcgtc ttcgatcgct   2100
agt                                                                2103
```

<210> SEQ ID NO 18
<211> LENGTH: 1535

```
<212> TYPE: DNA
<213> ORGANISM: Zea mays

<400> SEQUENCE: 18

gtgggtgtgg gtgctttgac tcgcggtcct cgtcgtggtg cccggtctac tactaggctt      60

gggccaccac gccagtgctg gattctctgc ctcgcccact cctttttttgc ctgcgatttt    120

cacagctgac agctctagac actagtgcta gtttagggtt tcatttgttc gtgtcccgct    180

cgcctcctac tgtcaaccaa cctcttttgc tcttcgccta gctagtcgtc ctcctgtgag    240

gtcaacttcg gggaattttc cacggtcgcg tcgcgctctc gccctttctg ttcgcttgct    300

gcacaacttc ggggtacttc ttggctggcc agttaataca ctttcaccca ttagaggcca    360

ttaccagaga taagtattcc ttgcttggcg ccttctccgt cggagatgcc ttaagactag    420

gctgctggga ctctttcggc tgttcaggaa accgtgggag agatcgctct tgcacttgcg    480

ccccaggcgt agaatgtgtt catagcgagc tcccatgatg gatcctcctc cccatcccag    540

ctaagctact agttcgttcg ttgcttcctt cttcctcaca gcagatcgag gaaggagacg    600

gacaagaaca acctaatctg gcctagccgt ggatatgatg cagcgtgcaa cgaaatggtc    660

aaacggaaca ctagcgcacg gcggggaaac gagacaacgt agcacggcaa gctagcagcg    720

cgacgacaaa gccatcgccg tcggcgttcc cgtacgttcc cgtgctgcaa attgcccacc    780

gtagcggccg gaggtgtgcg agttatccaa gcacaagcag cgtggtcaag gaggctgcct    840

acttggctcg agtggagtgg aagtcttgca cgggccagcc aggtcaccgg agactggcta    900

cacgccgcct gcccgctgag ctcgacggac ggcgcctcaa ttgcctcttg cacttgcact    960

cccgctctag gtggcgaaac ccatgacagc ggatgctaat actacgccgc ggaagacggc   1020

aggtggccat aggagagcgc cgcagacacc aggacagccg gcgaggcgca gcgggcacag   1080

cccagcaact accccgcaag gctcgtcgac cgctgcatct gcatcgccaa gaaagtaaac   1140

ataaatgtga taactatatt ttttttaata tttatatata tattttttat tttgtttatg   1200

taaataaaaa aacgaaaaca taatatagta tgggcccagc ccaccgtgcc tatttcccct   1260

tcatggacat actttcatgg acataggagc gtggattcgg tccacgggat cttggatttg   1320

gtccgaaagg tcaccgtata aaaaaataac tttttaccgt acttaacttt tgtatattga   1380

tttaattgat aattgaatat attatatatg tacctattat ttaatacatt gcatgtattg   1440

aatattgctc ctagtgtttg cttatatgca tggagcgact ctaggcgaga aagttctcca   1500

gaataataca ttgacgtcaa gatcaaggat ttgtg                              1535


<210> SEQ ID NO 19
<211> LENGTH: 1943
<212> TYPE: DNA
<213> ORGANISM: Zea mays

<400> SEQUENCE: 19

agagaggaca gctgggttgt actcgatctc gatgactcct gctccccgta tgcgagcacg      60

tcaacgctag atgtaccgcc gtcgtcgcgc ggggcagctg tcgccccgcc cgaatcaccg    120

tcacagccgc cacgcaaggt aatcctcctt tccagcatcc ctatgtctcc gtctccatcc    180

ctctgtcgtc tgatccgatt caccatccaa ttttgactgc tttcgtttca gttgtgtatc    240

ggtatataca gacgctggta tcaaggcaac acacagcaat tattactacc gccatcaata    300

taggcgttct cagctcgcca cggccagctt tgtactcctt ccttggtttt tggcgcacaa    360

agaccctaga ttactctagg tagaagagac ataaataaaa agctactgct agtactgcta    420
```

```
cagtactagg agtatgtaat accataggat caacggcccc ctctgcagct taagatccta    480

aaagtaaaaa gtatagtaac tgcgcgccta tactgtgcag aaacttatcc tctcactgca    540

cgccaattaa cgcggagttt tacctcacca ttactacttg ggtttggggg aagaaaaagg    600

cgctgaaaag gcaccacatg cgcaaccaga agggaaggct acgtatgctg ctgctgcgta    660

ctccgtgtgc atggactccg atccctccca gattttaagc gaggtgctag ctacaagtgc    720

agattgattg gcgctgacca tgcacggcgg tttcaaaatt ctccagaccg agcagttttt    780

ttgcaagcgt tttcgaaatt ggctagctca gctgataaat atagatacta taatgatgga    840

ttggttagct tagctaggac tataggagcc cggaggcagc gagatgttat tattggtccc    900

tcgaccgaac aggacaggat ccacgacgac agatcaggtc agggtcaaca cacgagagaa    960

attaaaaagc agtgtgagtg gaacaatcat gcatgcatgg atgcctagct ttggcgtggc   1020

ctcatctgct gctgctgctg ctagattcag atgcatcccg ctcccattat cctgtccagg   1080

ccaggggtgc cgtgacagtg acaggaagag gttgttgctt tgctttgctt tcctttcctc   1140

ctcgtttaac ttcccctttt gcccggacca aacggcacta taggctagct agcgcccacc   1200

tgaccccgcc gctgcataat ttgcacaccc ccgcgctccg gccccttcat cagccctctt   1260

ttttccccct ctcttatgca cgctaggttc cgaaatttta tctatttatt tatctattta   1320

tatataattt gttttatcca cagaaaaatc ggtagcacat catcaacagc gttctggggg   1380

gtggtcggcg cacgtgacgc cccccgtccg gctgggatga caccacacca cacgccatcg   1440

ctatgcatgc tgttgctgcg gccgcgtgag cgtgacacac cgtgcagcgg tcgttttctc   1500

ttttcggccg tccctccctc ttcttttcgg ccgcccctcc ctctgtgtgt gcgcgcactg   1560

tgcagcatgc accagtcacc agcagccgcc gctgtttttt tttttgcctg agaaagtgcg   1620

tggctgccgc gcccggccca tggccgggga aatgtccttt ccttcttcgg cctccgtccg   1680

gcggcgcacg tcctcgtggt gacgtgacgt ggtgcgtcat ccatgcacgg cacgtacggg   1740

gggagggggg ggtgcttgag cgcgtgttcg gtgtccccgc cgccggcaga cggacgagat   1800

ggttgtggtg cgtgcggcgc cgtcgatcgg gacctggatg gctagctctc tgcctctctc   1860

gtgctttgtg cagaggcatg cttttacgcc ggcgagcggc ggtgctgcaa cagtgcaagt   1920

agctagtagg taggtcggtg ata                                           1943
```

<210> SEQ ID NO 20
<211> LENGTH: 1569
<212> TYPE: DNA
<213> ORGANISM: Zea mays

<400> SEQUENCE: 20

```
gaggacgttg ctggagactg acttagtagc gagtccggcc actacacgca cgcacgatgg     60

ggtgtgccgg ctattgcgaa ccgatgcacg cagctatcgt ctcttcggct gttcggcacc    120

atgtgagagc tgagctatcc ctgagcagct gcagtgcaca cggcacctgc gagcgtttct    180

tcgaccctgt gttctgtgat caggtcgcaa atgcgttgtg ggcagaaaga aggcacaggc    240

acggccggta cgcgagcctc cggtcggcgg tggtagcgcg aagaaggcgc atggagcgta    300

cgggtgacgg cgtgggggca gcgaggccga gattgccgtg tgagcgaatc tgaagcagta    360

caccgtgatc cgtaaacgat ggcccacttc actttgttgt gtgcatgaac gcacgccgac    420

acggccacgt gccacggcgc ggtggttcga tcgttcactg gtttggtact tcggttcggt    480

ccggttcgct tccggccgcc taacctgcca cctgccaggc agcgggcagc gggcagctcg    540

gacgacaggg ctcgtgagcg cacacgctgg ccatctatct atcttctcca gcaactcctg    600
```

```
atctggaggc atgagcgcgg ccggctctgt tcggccggcc gtgcgctgga aaaggggtct    660
gcagatcggc tacataccct aacagcaaac cgatgtgatg tacctgtagc atgtcattgg    720
cagcctgcat gcgcgccatc gatccccatg cattgacatt gtgattgtga tgttgattgt    780
tgagactagt cagtgacatc gctttcaaga tgtaatttcg aaacctattt tgctgtgatc    840
tggtcaccag ccggaggaat aaaaaagggg tttttatagg cgtgcgcctg tggtctggct    900
ggtcacagga aactcagcga ctctttctgg ctggtctctc actgactacc ataccaagca    960
ctagaactac tctgtctgtg ctgaacaatt ctttttctca cctcctcaac ggtcaacaca   1020
cagtacaggc tgagacttgt tcattcttcg ccggcctgga agctactact acgtactata   1080
aaacaaagca cgtacgcatt gggcgatcgg cggcgtcgga aatggtgcta gtagtagtat   1140
tcaggagcta gcgttgaatc cgccgtcact ctcgccacca aatgcgctga acagttccga   1200
ttccgctttg aagctctcaa acttcacacg tcgccatcgc cgccatcact gcgcccggtc   1260
acaatcccta gaagccttct gcacaacggg gcagcctccc tctgcctcct gccgatccct   1320
gcgttcatcc aaagatctca gctagctagc cctacattcc cctccgctgc acattgttgg   1380
gcgtgcagcc ctgcctgcaa accgagaaat ttgctcctgt ggctctcatg cccacatgca   1440
caaccacgtg gccatgacct gaagccccca acaccccacc ccacctagag atctaacgct   1500
gctgccgata tctcatgcct agaccttttt ctatgggatt tggtcttttg ccttctagcc   1560
atattctca                                                           1569
```

<210> SEQ ID NO 21
<211> LENGTH: 1750
<212> TYPE: DNA
<213> ORGANISM: Zea mays

<400> SEQUENCE: 21

```
gctggacttc agcgccatag gtattttcgt caagctcgtt accaaggttt atgacattga     60
ggtcagcgcc ataggtcatg gtgttaccat atcgttacgt cacttctacg ctaacatctt    120
gtcgatggtg tcaaactatg taacctcgac gctatagaac atgaaataga cctagagtct    180
cgaatcgatt gtagttttgt ctcaagtcta aacatgtgtt gttgccctct tgttttgtat    240
tttgttcttt tttttgttac gagagaagag atttaaaaaa aaacacaaga attgacgtat    300
ctgtaacgag cagagtacac acgtgggcta gctctccgct gaaaagaata cgatttacat    360
acgtgtaaag gttgtgccca ctcggcagaa atttggtgat gcggggccag gtcgttagcc    420
tcggatgcag cctgcaggca gcctgtggtg tggtgtggtc caaaaagggc gggaacagaa    480
acgaggggct ggacgcctgg acccatggat caggtggtgg tggtccgtgt gggcgcaagc    540
accagtacag tacagtacag tacttccccc cccgctcctg catgcatcgt cctctgtaaa    600
cacaaggctt tacccgaaag cacaagctca cctaattaag ctcatgtacg cttctggcgc    660
gcacaataga cacgcccgta cgcaggagca catggcacca accgaatgat ttgagcaacc    720
gtctccgcat ctggaatcca ttccactcac ccaaacagag ctccagctcc ccctctatcc    780
agcgagctgg acgggacggg acggagcgta gactagcaga acagaagcca ggcaggtcgt    840
ccggtcgggg tcctttccct ctttctctcc gttttctccg ctggggaaaa agaaaatcgg    900
aaaatgacgc tccacggaag aagcgcgcga gccgatggca atggttcccg tcagcgtcga    960
gcggcgatgg tccccgagac tttttccccc cctcctcccc tgcgtgccgc acacggccgg   1020
aacggtcctt gctgttgcgg ctttctatct tggaacagcg ccggccggtt gaatccgccg   1080
```

```
tgttcctagt gcaagttgca gagcggagca aagcaaggga ccttgccgca aaaaccgtgg   1140
cggggtgtcg tctaactttg tccgtcaagg gtcgccgtcg gccttgacaa aacggacagc   1200
tgctgaccgt gacgagttag aagagagaga gagagggaga tagaagaaaa atcacccacc   1260
tccggacctc cccacacgaa acgaaaagct acgacctacc tctcttccag acgtaacgta   1320
agcatgaaac agaaagcact gcctgccgga aaaacaaaaa caaaaacaaa aaaaacccga   1380
aagactaata aataattcac cgctcctctt tcgcatttct ccggatcttg tatgcatgat   1440
gtgtgtgtgt gtgcctgtgg ataattggac gcactccacc ctacagtctc ctctctcagc   1500
ttcgttcctg cgcccccgta tcgtatccta atcctaatgc atgctcacgg ctgggtcccg   1560
tgggccacca ggtttttaat gtgcccttct gtagccacac gcggaggggga aaaggaaccc   1620
gcaagaaatg agagtggaac agaaggcgtc tatttttgca cgatggtata ggaagcctgc   1680
tggcgggctc gacggtgcct cgatcagagc gtacaaaatg aagcgtgtga agctgttgga   1740
gttgacctac                                                          1750
```

<210> SEQ ID NO 22
<211> LENGTH: 1942
<212> TYPE: DNA
<213> ORGANISM: Zea mays

<400> SEQUENCE: 22

```
gctcgtaaac ctcttcgttc ttttccatgt tggcggcatt ccctttgtcg tcctttgaac     60
tagaccctta tgaaaaataa gtcgcttctg ttatagtaga tgggtatcta gatagatcag    120
aacagggatg cccactttg ctttcacatt tttttgtcca ccacaataat aagcaacatt    180
gtgcctaaaa atatgttctc cgaggcaaaa agaagtttta gcctagctag ccatgggttg    240
catgagctct gacaaggcct tttatggcct agtcactttg gttcgcacga aaacaaaagg    300
ataatcttct atagttttta aatccaatta atcaaaaaaa tcagccgatg caaaacttgt    360
agctatattg caatttgcaa agctaataat tagtgtaaaa actacgtacc ttgtgaggct    420
tacctgtgca tagggtgggc tataggaaga agatgcgtca ttatctaaaa ttaagcctta    480
atttggatgg agggaaaggt atttgtggaa tgtattgtta acggtgtagt actccaatcc    540
atgctactta aataaatatac aaacggacag gataataaga tatcaatcat atatactcca    600
aattaatgat tggcatgaaa caagttaatc aaactaatgt ctgctagaca agataaaatg    660
ttatcaaatg caaacacgtg tgcgattgtc gtcctcacgc gcatatcgtc ggccttcagt    720
gtttttttct ttctttacat aaaatattaa aaaaagatca gaggggaatt cagggagaaa    780
tggccgggaa caagactagc cagaggaata atattgagtc acaaatcaca cacagaatgc    840
acatcgatgc ataatatatg cgtccgcctg tcggtctcat cgtcagagtc aatcatcacc    900
tactgacgaa ttaatggaca aaaatcacat cttgctatgc acaaaccggg acttgctacc    960
aactctatct tctctctacg cataaacaac atgtaaccca caaattaaat gacgatataa   1020
tcgcccagtt catgcatgag ctaatattgt ttttgggggg tacatggaaa atcccagtac   1080
gtgtatcttt ttcggtccag ctgattattg ctgatgaggg gccggggcca tcggatcaac   1140
agtcgcgtct ctgaaacctt cactgggatg tctgatgtct ctctcccccc tctcattctc   1200
atgagtaaac agttcaactg catacatgga cgcgagacct tcttcttttc tcgcagaaga   1260
ttgctccttt ccttgacgca gagattaaat aaagcctgaa agcgatgcgg tttagatgga   1320
gttaattaga gctagaacat gagttttgga aagtgtttgt gtagtaggcc ggccagcagc   1380
aggggtagaa tggataggcg cacgcaacgc aaccgacaag cggcacacgc tggtactgca   1440
```

```
gcctgaaagc tggctgacaa tggtggatcg agctactagg tagttagcta gggcctgcag   1500

ctgcaactag gccggtgccg gtgcttgctc gttggacatt atatataatc ctgcaaactg   1560

cgatgtgccg tattgaaata actagaaaac aatcgctgct gtttgcgaag gttgttatag   1620

attggatgaa caaaagtgta tatatatcgt ttctttttaa tttgtcatat ttgtagcacg   1680

ttcgaagctt tagttataaa aaaactaaat ggtaaaatct tgaagtatgt attatattaa   1740

taaggcataa cacaaaggaa atgcatcctt catttattgg cgcaatgata ttgcactggt   1800

agattaatcg ttctaaatgg aagaccctaa acacacatag ctagcagcgt gaccttgaag   1860

ggaaaggagt acgaaaaaaa atgttgtcaa gatgacagga atggtagctg gctagtggag   1920

cttctcggtc tcggaattca tc                                            1942
```

```
<210> SEQ ID NO 23
<211> LENGTH: 1574
<212> TYPE: DNA
<213> ORGANISM: Zea mays

<400> SEQUENCE: 23

ttcgtaataa taatgcaata ctgatggaga cgtcgacgac tggacacaga ttcatatata     60

ataatgcaat actaatgggg cgccctcagt ttcagtcttt gcgctggaaa tggccgatca    120

ttaaaaaaat ttcttttgtc gaaattcata gacttgcgaa acgatcttga aatatactta    180

cttcaccatg ttcctgcacc caaaaaaaaa agttctccca ttcccatcct cttccaggaa    240

caaaagcaca gctaccctac ccaggtgagg gctgagggat gtgtagtagt actgtccatc    300

cctgcatggc ggaatgggcg ccggagtcgg cggcgcttcg agaatcatgc gtggcaggca    360

gcgagaactc caatgcaagg cagcttgctg ccatcgattg ccatgactga aacacgcatg    420

catgcatgca tgcagagttc tagtgtctgc aatggacaat gatgaatcct cctctcccct    480

gcattgcaat tgcaaagcag catgcaatgc aatgctctag atcttccggc gactgggcgc    540

cggcgaccac gcccgcccgc ccaccaccaa ccatacgcat gaattttaag ctgcccctca    600

tcaaccagtc atgagtcatc attgccatgc accccccccc cgccgcgtcg tccgccgtgc    660

ctgccatgcc atcgccggac cagacacaat gattcgccca tgatcatcgc cggaccggct    720

agtcgatgtg gatcgaagca acgtacgtac tgtacgctgt gctgcagtgg caccaccact    780

gtatgtatcc actgcaccgc ttgttgcgcc cacaccaagc acttggtagt ttgcatgccc    840

cgcagaggtg tgcaggccgg ccatgcctgc aggctggctg cagccggctg catgcatcgg    900

ccaagcttgg ctgcagagct agcgatgcat actgggctac tggcgtcgca ggcggcggtg    960

atgcgtagtg cggcagtggt cgcggtcgca gccggccagc aggaagcgcc actggggttt   1020

tggagagacg tgcatggcgc tttctccggg cgctagctag cttagctcga gattgactgg   1080

caggctgcat gggcaggcag tgcgcctggc cgcgcctgac gacggctgtg cctcggctag   1140

ctcttgctgc cagtgccagt gccaggcaag ctgacgcccg gtttcctcca ccaccggcca   1200

ccgccatcca ggatcaggtt cagaagagga gagaaaaagt gtgcatgatg gagaaatact   1260

gtgagcttca gtttgcccga tgtcacagca gcgcgcgcgg tgggcgaggg aacaggagga   1320

catgtatgtg ctcagctcca tgacccggcc ctccaactgt ttacggtctt cgtggccctc   1380

taacggttac agtgtgagga tagcgcgcgc tccgtcaggc caagtcaacc ggatgagtgg   1440

acgcagcaaa acagtgttgc atgtcacaca agaatataaa aaaaaatttc ccttcgcgga   1500

ccccttttta ttcaccggtg gtgccagtaa ctctttcctc cctatgctta cgtatcaatg   1560
```

tgcagatagc taga 1574

<210> SEQ ID NO 24
<211> LENGTH: 1601
<212> TYPE: DNA
<213> ORGANISM: Zea mays

<400> SEQUENCE: 24
taactaatat gcctcactaa tcattatata cataaacaac tgattatttg cctcccagcc 60
aatgatataa gaagtgacaa aaaacatgta aaatcaccac caggaagaaa aaaaaacttt 120
ttcaatgttc cagtatataa catatatact gacaaaagac cgtatgagaa tttggcccaa 180
tagtccctcc aatttgacgt gatcaatcta aaccacttgc tagtttcact cgataaagaa 240
gttacccaat ttccaatgcc acatataaca tatatggtac agcacccaaa ttatttgaat 300
ttggacataa ggaaacgtta catgcacctc aagaactaac tgatcagttt ctggcctgaa 360
aacaccagat tacccagcaa gtattggaac agtcctgttc cagttttagg ggagttgcca 420
atagctacca ataaatgaaa ttgactgtcc aagcattatc tgaataacag gctcagctgt 480
tgaatttctg acaaggtgaa aacaataatc ttactcagta tatgtcttgt tgaacagctc 540
gcacgaacca acaataccag gccctccaac tttcgggtac tgaaatagta gaatgaagat 600
gatgtggaaa atgcagtcaa aagtcttgta aattataaat ttttagtagt ctggaaaatc 660
ttgcgtccat cttttgaata ataatgtgaa gaccagagcc atgatgtgca agattacaag 720
atttgatatc tgaactttga agtgacatat tatcaatata cactaccaaa tcaagttcat 780
ttgcatctca acctcatcgc acagttcgaa aaacctaagc aggtatatat aacatggcat 840
tctatagtgt atggctttat gaactacttt cttattttgc aacctacttc ctgatgtagt 900
ttaagataat attggtaaaa aaatgaacaa tgtacaaatt aatccactga tccattatca 960
agcaaaaaaa tgttgcaaat gatggaactt gcctgtgata ctagtgaaag aaatttgtag 1020
gtatccaatg catatctcac caaagcctca ttctcccctg gatttatagt acacctgcaa 1080
tgcagaaaag aaagacacga gcactaataa acattattca ctaagctctg ctttataata 1140
catcggcaat gcagagaaga aaggattgag cactaacaaa ctattcactg agttttgttg 1200
tttgtccttt gaattggtaa tcacacttac cactatacca gttcgtattg tatgatatgc 1260
agatactaga taggataaca ttgtaaatta accacatgta cataaactag gattacaaat 1320
caagttcttc aatcgaatag caatcaagga tagtcctgca atatatgaat tagttgattt 1380
cttgactaat gttaaatttc ttgactacat agttatgact ggtatttatg cagcaactac 1440
aatgaatttc tgatgataaa tcactagctc caatgttgta cctggtcctg tcctttatgt 1500
tcaatctctg gagcctggat aggacaaatt aggtggcttt aggagctcct aggcacgtcc 1560
agtaagtgtt tataggcacg tgagttgtat tttctggtag g 1601

<210> SEQ ID NO 25
<211> LENGTH: 2872
<212> TYPE: DNA
<213> ORGANISM: Zea mays

<400> SEQUENCE: 25
tttaccgcag catcacgccc acgccggcct ccatgctctc gatcgattat tatatttccc 60
accgcgcgcg cgcgtccaga tgctgccaga atcccatcat tcatttccat gcccggccgg 120
ccggcctgcg tgttgaaaag ttgcagctag cacacagtat cgctatcata ttcaggttca 180
gccctgcagt tcgttgcagt taggctctga aacacatgta gatagttaga tagatgcaca 240

```
cacacacaaa tgcatgcgag gaggatcatg catgatgatg aacagtcgtt gcgcagtaga    300
gtgagtggag cacacgcaat cagacgcgct gatagctcct gtaattgccg ccatcagtga    360
catgatgatg atgctggcgc gttcattaat tccctgcagc tggcagatct ccgatcccat    420
ccgtcgtcgc ttgcagtggc tcagcgagag cctctgatga gcttaagctc ttgttcaata    480
tgcgctcatg catctcactg tattacatca tgcttactcg gtgatgatgc atgacgagac    540
cgggcaaaat gttgctcgca tcgggaatga tgaggaatag tagtgtatat aatgatgcgc    600
atttagtaca gccttttcga tttgtttagt cttgatgctc acgggatcga tgagaaaggc    660
tgcaggccgg gtgcatcagc tgctaatcat caccttgtct tatattactc cagcgatcga    720
tctaatctaa tccgatatat gtatgcggta tgcctagctt tctagttagt tatgtaaaat    780
gcagctagca aaagacacag gggtatactg atactagtat acaataataa tgccctaaat    840
aatgcagagc acatgtatct aatgcagcag aaaggcaaaa gaaagggtaa agaggtataa    900
gtagtgtagt gggtgtgcat gggggccaac cacaacagtc tgaacaaacc tcttgcattc    960
tgcaccatcc atatgcatat gtgcttgctt tcgagctctt ttggaacaat aatctgcagt   1020
ggcccgccta cacagtcact ggaccaccac agtgagaaca agagagagag agagagcttt   1080
ggtggtctgg tctctgaaac ccatgtgatc atcatatccc tgccctggcc actaaataat   1140
ataatttctt gttttccatg aaggatctgt tcacgcgatg tagatcaagc ttacgagcat   1200
gaaaagtggt cagaactcct acttaataag gagttcttgg gatatatatt tgaccctact   1260
tctagtatag taactacata taataaacaa ctcagttgaa aaagtggtca ggtcaactct   1320
gctggctggc tgttgaggtt tcagggtcat acaaacaaga ctggtgaaag ctatctgctt   1380
tacttgtcat ggcgccatat ccccacgatc gaggactttc ttttcttgct tcttcctctt   1440
ccttcagtgc tagctagttc tgtacgtctc tctgccccct gggcctgcgc atcctccatt   1500
ttgccgcgaa ccatatgcag acaacgcgcg tcaaaataac cctagtcgtt tactgctctt   1560
gttggtttcc ttggattcag ctagctgtgc gtgtgccccg gcccccaaat aaggtgagat   1620
ctgtcgtctg aaggcaggca tatgatttgc cttgatttct acacccagca ggccgggggc   1680
cggctccatc gagagctcag ggacacagag ttgacatcag tgtgtatact ttttgtacgt   1740
tacacttgag tgcttcatca gctagctgct agctactcca ctcctagtct cctactacta   1800
tatattgcgg tacatgacca tttgccagct gctgtaatga cacaggtgct atatatattt   1860
ctacaaacca aaatcaaagg aagaagaaaa aaaccagctt gattatcata tgctggatta   1920
aattatccaa tcatcccaca atcatgaaat agttaactag agtaacgtac ggtaaatgct   1980
tattattaat tttggatcat gagtaattaa acttttttct actgtttgta cgtactttaa   2040
cgtagctggc agctaaatcg ggtttaaaag cggtatcttg gtctagctca aaagggtcac   2100
ctagctagct ttattttcca tgcatgaaaa atatgaaagc tttgctcgat cttttataat   2160
ttagaaagtt ccgcgcgctg acttgtttgc atggtgtgtg tctttgcata gctctgctgc   2220
cgcattaatt ttgccgcgca ccacgcagag acagtgcgca tcaaaatgca agttctggtg   2280
gcaatgcttt tgttatttac tttgttcaaa caaaagaagg taaaaatgag tcgacgaaat   2340
ggtacgtaat aaatatctgc tcagttgcaa ggcatgattt gccttattgg ttgctttgct   2400
tccacccagc tagcgctgaa cgcttcgaga ggcagggaca catgacaggt ttggtacacg   2460
tactcgagtg cttcatctgg ctagcaccgc tggtgagatg agtaactttt acttaaacct   2520
aggatatatg atcactctta tagtagtatt acatcgtgca tcaggccacc aggttgaacg   2580
```

atacacagta aaaaatagga gtagaggtca ataaatattt atattccacg aataagatat 2640
catttttttt tttttgctga taaatggtaa aggagaagtt agaaccccta agggacataa 2700
taaatatttc agatgataat atcgttaaca cacaagagag taatgtccaa gatgaactaa 2760
ttgacaagag ccttatgcta ttaaacttat tcatcccttg tagttaaaca gctttcatta 2820
aagagagaaa tattatcagt ggtaaatggt aatgattttt gcataaaatt tt 2872

<210> SEQ ID NO 26
<211> LENGTH: 2642
<212> TYPE: DNA
<213> ORGANISM: Zea mays

<400> SEQUENCE: 26
gtgagtaaag taaacttcat aaatttgaat gcataagcac ctagtacgca aatacatgcg 60
tgaaaaataa gagtaaaatg tcggctccat aatcctgcat tagggataaa catgatatgt 120
tcagggaatt ctaacaaaga ccgatagatc tacacatatt ctcacctgaa ttggtgtacc 180
agtgagacac cagcgccgat ctgcagtcag agcagccgca gctagggata tcaaactttt 240
agaagatttt atcatgtgtg cttcgtcaag cacaactctg aaccaatgta cagagtacaa 300
agccccattt tctgttgaac cctagccaag cagatatcaa aagttcagtc aagaataagt 360
ttgcataatt caaactaaat attaatagca atggacccag cagttcccca tcattgcatc 420
catactttgg tcaatgtggc tatcttgttt atgcatgtat ggaccaaatt taagcaagcc 480
atattttacc aataagattg tgtaagtatg acatgaagga tcaaatgcag aaacatggtg 540
ggaaggacaa aagacaagca aatgggtaat gcattatctg tattattttg ataaaaaatg 600
gacacaagta aaagtagaag atgtcaaatc aagtggctat agtagtaaga gtatgcaaat 660
gaccaatcaa tcgcatggtc tggtgctatc taggttatct taattcttaa ccaatgaatt 720
ttttacaaaa gcttgaacat aataagagta aactgaaaga gatataagat ctcagagctt 780
acatcgattg aaaactctga tgacacaaca ccatatgtag tcaggacaat atcactctga 840
ccaatgatgc ttgcatcttt tggcctgttt tgtccatagt gaacatatat attcgcagtg 900
cctggcttag tatgagcttc aatctctgcc tgttattcat aacatcaact ctagtgttca 960
gaaaaatagt tgaaagaaac acttaaagat gaaattggta aagcaagtca aaattatgtt 1020
aacctcttat cttttacttt tctgcagcaa ataagcacac atataatgta gcataggcaa 1080
tggtggggtg gtgccacaat tagaactata ccttccactg actaattagt gtcattggac 1140
agataattag attgcttcct ccaataagtg gggccttagg tttcttgtgt ttgctaaaag 1200
agaaagggtt agcaagcttc ttcacagcat catgcgattc acccaaccca ctagcttctc 1260
taggggtctg agcagcattc tgagttgtga tgcatccttt gctagaatca gaaagaagaa 1320
gagctatcgt cataatagtc ttccccagtc ccattgcatc tgccagaatc ttaattttta 1380
ctccagttaa tagaattgat cgtaaaatca accagaaacg atagctatca tagaaatgct 1440
aaacataaag aaatacaata ttaaaaatat tcttactcct cctctagaaa gttgtaatgt 1500
actaggaaat tcagttgtag catcgcctga aaacacgttc aagtacaaaa cgagttccct 1560
cctgaaataa atgcaataaa atatgaaatg taatgtccaa ctattgccag aatggttatt 1620
aaaaacagct catataacac atgcatactt atcctcaagt ttgtatgctt cccaacaagg 1680
gtgaagggtt gtagcggcat cctgggaaga actacctttc tcaagctgca gcatccaatg 1740
aagtgcctgc ttttgataag agcgtagatc acacatcaga gaatcagggg gagccctttc 1800
ctacaaaata taaattcaga gcacactgag gtcaggataa tatccactag ttgctgaaac 1860

```
actgcacaac gatgggctgt tgaattacct ctagtgcaca gctgtctgag atcccaatta   1920
tatcatccaa atctgaatct gaaacagttt cttcaccatg atcatcttcg tttccatcag   1980
aagacaacct caatctgccg gatgtcagct ttgcagcagg agaccctata ctgctctgtt   2040
caggcagaaa aaacataaaa ggccaatatc tattattttg atagcagtgt aacgaatgaa   2100
gtactaaact attacctttg tttcagttgg ccgcttcctg gaataaagat cttctggagt   2160
aaaagcggcc tgttttcaat ttatgtcaaa ccaaaaaaaa tcagaccata ctaaaatgtt   2220
gattccagag aaagaggaat gcatgtgact taaatggact tgtttctttt aatgtctttt   2280
tataccttta tccacattct aaaatcatat gttgtacaat gttggggtaa agatatataa   2340
atggttctca tacttcttaa ttttttgctt tcagtgttca tcagtgactg ttcaaaaaat   2400
atttatcaac gctacgctaa tttcatgata ccaaagaaca cctaattaca attgtacaaa   2460
ctttggcaat gcatatttat acattcacct atccaagagc tttaaattgg tagacttttg   2520
cagtgcattt gcactagata ataaacgagc aggggatgat aagagcgcac agctcacctt   2580
aataaaagga gcaagtccta tcaatttgaa aagtgcaggt agggggtgaa atgtggagtc   2640
at                                                                   2642
```

<210> SEQ ID NO 27
<211> LENGTH: 1657
<212> TYPE: DNA
<213> ORGANISM: Zea mays

<400> SEQUENCE: 27

```
aatgattgaa ataaccttga atgacttaat atcatagttt caatacctat tcctatccac     60
caacttgttc tgatgagggt tatgacatct cagtgtctcg ctcctgttgt tcagcaatag    120
gagcctttgc accaacaccg cctttgccac ggggtggtct cctttcttca ccgtcatccc    180
catcatcatc cccccgtaca cctcgtcgtc cttaccctca tttcattcat ccttctcctc    240
atactagtgc tagcagcgga acatttatgt tcctagtata taaaacttaa atgagtcaat    300
gtcacaagaa acaatacgat gcaattcaat agcacaaaaa tgctattcct attaataaaa    360
tgttttcact gaatataaaa taagaggata tctgaatagg tgaagcatca ataaaaataa    420
cttaaaactc actgattcac tatccttctc ctgagtctca cgtgctgcat ttgttgcctc    480
ttaccaatcc tcatccagct ccatatcctt tatatcctca ccattaggcc gaggcttctt    540
gaaaacccgc ttctacaaaa aatcaaatgg cgtgaaaaca taatcggatg tctaaattca    600
tgaaaattat aacacaatga ctaaaactca caattgtgtg cctcttcgca cacattgcca    660
aagtagaata tccaattgag ccagccgaca ctttgtcaga actaataata gctctgatgt    720
ctccaataag cttctcatgt gccctcttta ggaccaactg tcattcctgg tattttccta    780
tgccttttca atcttcagct aattggcttg gatatttacc agacatcttt gaaacatctc    840
tattacaatc tctcaaagcc ctcaaaacct catccttaca aataatgtca acaatagtag    900
caatttctcc tacaagtagt ggctccaaac aagaaagccc atatgcctct atttgtggaa    960
cttcctgttg agaaacagga ggaggagtag gtctactaga aggtcctgcc ttcgtagcat   1020
cgtgtgtaga agatggtcta gctcctctca tagcaactat tttccaacca tgtcgtggat   1080
taggaatata cttcattatg ccatcctttg ctttaaatat gccagctagg gaagcgcctc   1140
cccaacatcc ttctgttgaa caccgtgatg aacatcatta tatatagtct caccgacatc   1200
cttcaactgc aaatcaaaaa gcaaaaaaat acaaataaac ttcatacaaa acgattgaac   1260
```

```
acaattgatt ttgtaaaaaa agatgaaaaa gaaagaaagg catgacatta ctaaccatca   1320

acttgccata agtaaaagca tgagaaactt ggtccacaac tcgatctgcc tttgttatcc   1380

tcatgatcac atcactagtg aaaatatcga gatcgaggtg tgcccaaagg gacatcgaca   1440

ccagacaaca aattatctaa aaagtaaaca tgtagatata caaaacaata taaaaatatc   1500

taaatgtcat aatacaaaag ctaattatgt gaaatgatta tgaatcatag gataatttct   1560

aagaatttat agaatgactt aaagtgacag aaacaaactc acatatattt attatgacta   1620

aaaaacatga tatatgaaat gacttaggta ggcaaat                            1657


<210> SEQ ID NO 28
<211> LENGTH: 1912
<212> TYPE: DNA
<213> ORGANISM: Zea mays

<400> SEQUENCE: 28

acattgcaac aatatgtcta tatatgatgg tttctgcacc gtgatgagta gcaaagccac     60

catgcatgac cgatatggcg attggcgaac ctaaaaggaa agcgcgaacg cgaccacttt    120

ggcttggcgt cttcctcgtc tttccactcc tacatgcacc ccctattcca tcgaggcatc    180

atgcatgcat gctgtcctgc tcgctaaaaa gccatggatc atgcgatgcg cacgagagcc    240

ggaggacaaa gcaaaggccc tagctagcta gctagcaagc ttttgtaaag ccgccatttc    300

cgattggcct ctacctcgaa cagatctcat cgatctcgat ctgccgcctc tcccatcaag    360

ctgtcatgag tgacaccgtc gtcgtcacat gcacacatgc gtggcgggca ggaaaaatgt    420

gcatgggcga acgagcgagc cgttggttgg aggcccgccg gccgtccaag cacgacatgg    480

agatgatcct agtcgtccgc cccgccctct ctgatatgta ctagaggcaa gtagtcctag    540

cttgcacttg tgtgtctgcc atgaacaaac acgacagtgc atgcatggtt gcgtatgtac    600

aagtcttgca tgttgccatg catagggtaa aaaagagaga gagagagcta aaagtgatca    660

tagcattttg aatgtcgtag ctattttcaa tttcttctat tttgaggaag ctaagctagc    720

cacagatttc cagatgctat agggtaaagc tcaaaatgct agcttctctc agctctgtct    780

cttgttctga gaagttgttg cacgtactag gagaagatcg attgaactct agctactggt    840

aaagttgctt ttgaaggtaa attaaagcct aaagctaact gatcagctga tttactagga    900

agctgagtct gcagcatggt gtggtagtgt gaagagagat atacagtgag agcatcatat    960

cgatcggcat gcatactact aatagtgctt cccacgttgt cactcgcttt ttgctctgcc   1020

ggccatatta attcgttact ctttattttg catgagttca tcagatcagt tcctctctcc   1080

ttagaccagc tacatacaga caacggtggc gagagtccat caccatcagt atctattggt   1140

atttaggatg gactaaggtc gttcgtcagt gcttaatcac accgtgcaag caatgtcatt   1200

gtacttacct ttgctttatg acatgcaaca gctgcatgcg ctgcagatgc attcacctcg   1260

aaatgcatgc atgcaccact cgccagtcgt cactcaccag cattatattg cttgtgtctt   1320

ggttttcggt caccccccct ccccctctac aaattactat agagagtgag tgagattttt   1380

tttttcactg gacaacacga cgagtagtag cataagatat atagcctaac ataataatcc   1440

cattccccta gaagaaccct atcacttaac caccgcccaa tgcaggaacc gctttatatt   1500

taaatctggc gatattcttt actgtctgat agttcgtgcc tgtgatcggg aggtgtgcct   1560

caatcatggt taacagaacg aacatggggc ttgtgattcc tccttagctt ggccaagagt   1620

cacagtcgtc gtcgtcgtca gtcagagggt aggctactca catctatgcg aactactgac   1680

atcttttcct cgattctttt tatcgtcatg ggaacatgga gcttttcatg agtctactgg   1740
```

```
gctagctagc tagctcgtac aaccatgaga ttggatacag cctataccgg cctgtctagg   1800

aggacaaatg cctagagaat tttggaacca aactcgaaag catgggagta gtttttcact   1860

ctcaagattc aagaggccaa gtagactagt agagtgtagc tagggagact ag           1912


<210> SEQ ID NO 29
<211> LENGTH: 1275
<212> TYPE: DNA
<213> ORGANISM: Zea mays

<400> SEQUENCE: 29

tatagtcgat ctaatgacat agaactgtac tgactcttga aagatttcct gaacttttgt     60

ttggtaaaat atcgcgaggt caataaaagc tataagtcat caccccatta ggatgaagca    120

aagcaacata gacaaaacaa aagttaagag acaaacagca aggacactca caggaaccat    180

gataatcatt atattatatt agcgtgtatg ttataaaagc taacctgcct gcccccacat    240

attacatact gtagcataaa atattcaacg aattaaagca agctaggttt aggaccacat    300

gagcagctct gcctgtccct gccgcggcgt ccaatgggaa gcagccataa gcaacgcgct    360

gccagtaccg ccattcagat ttcagagagg ctcatgatga catcacacat ctcactttgg    420

atgggtccca cttcgccact accaacgcct gcagtgggtc atgcatgctg ccatggcagc    480

atgtgggagg gggggctcag catcaggccc tcatcacaca gctcgtcaag tgatcggccg    540

gaatggagac ggagtatctt tttccaatgg aatccccccct gcacgaacaa aggaatccag    600

tgaaggcatg tggccgcatc agacattgta tcagctagcg gttagttaat aaaggagcct    660

cagctagcag ggaatctttc tgcactggca tttgctgccg ctgtgatctt ggtctttggt    720

cgtcttgcct tgcgcggtgg ggtagaacaa gccagcagct gttagcagag gtggatgaaa    780

accatggtcc ttgcatgcac agagagagag agagagagag tactcaggct ggcagcagca    840

gccagcagca gagcgagggt ggtcaaggac acttgttgag atgatgtgga gaggtccgtc    900

catgtccatc tactaccagc ctgcaggaac tctgttcctg attcagccca ttcaattaag    960

ttgttagtag taggagacat gtcatcagtc gatgtgcagt acgacatgca tgtgtcttct   1020

gctactgctg tgtctccaaa ggctcatggt ttcactgtca caccgaccag tgctgctgct   1080

gatgcaacag ttgcggtggt acttcactgt tgcatctcgc attcggttgc aataccttga   1140

cttcagttta gatctatcca aaaacacgct gcctgtcgat atcttgcccc gggaagcatg   1200

gagtgaacag aatcaccaca ccagggcgat gttcatctac aagcgtggcc aacgaatagc   1260

tgtttacgta caagc                                                    1275


<210> SEQ ID NO 30
<211> LENGTH: 2102
<212> TYPE: DNA
<213> ORGANISM: Zea mays

<400> SEQUENCE: 30

attttcacgc gaatatgccc ctaagaccct gtccacttgc ccttgccttc tcttgcacag     60

ctccccgcct ggcgcctgcc gcctgttgac cggacgcgtg cgtccgtagc gtggcgcacg    120

tacggagtac tcgcagcgac cccacccgaa acgagccaaa aagaaccaca ccgcacaagt    180

gccaagtgcc aacaccgccg gaaaccacct cgtgctggcc catcccgaca tcccgtcccg    240

tgctcccctc ccctcctctc gaccacctcc tcgtcgtctt cctcgccccc tccgccacct    300

ccgccccggc ctctccgctc ccaccccgc ggaaacccta actccctctt ggcacaggag    360
```

```
gcctatgacg gagattcgcc gcgcgcaagg agggagtgga ttcgcgactg cgcagccgct    420

gccgtcgtcc tagggcgcgt cgagcactgc caccccattg acgggcccat ccccacgaca    480

tccgccatgt tcgagggcca cgtatgatct cttacccttc ctccatgttt tcccattcct    540

tcagcacctt tgatcgtgac catttttgat gcgcgatatg gaggaaggcc gcgtgattgc    600

ctagtggacc gatgtgttgg tttagtcgtg gcgttgttct gtccgggtta ccaaatctct    660

gtgcagatca tgttcgtatt tggggatagt ttggagggtt agaattcggt gcgttgatga    720

ttgacccttg gtcgtttgcg ttatgatctt cccttgagga agaattgcat gttgatttat    780

ggaggagcct ctaaacgggc aagttgtgga cttttggtgc ttatgtatac gtttgttcac    840

aattttatag ttcgactgaa ttccaactat tgaggaatct gtttactttg gttgagcaaa    900

atgccttatt tcatttggcc tacgatcatt taagtagctc atgacacatt gtctgtgatg    960

gttgcatatg gtgatctggc agcaatgtga aagttcatag ctgcggcatt tctttctttt   1020

taaattgaaa tctcctagcc cctgttacct cccgacaata tgcacttgtt gccctttaaa   1080

tttggatatt cttctttcgt gattgcatct tattctcacc agtgaatgca gttttgagca   1140

tccacactat tatggtgaga gctatgtttt gtgccatcct actgcactgc ttgggatttc   1200

attgtgtctt ttcttttgcg tcattatgta agaaacaatc atgctggtaa atagtggagt   1260

cgtgagtaat tcatgaggtt ttacagcaac tttgctcatt catggcaata gacacgtacc   1320

acttaaatgg tgaatcatgt tatgcactct ttcgctatct ataatttcat atcgaatttc   1380

tattttttgt tttccttttt ttgactcttt catcattcat catttgtgtt aagttctgag   1440

ccatgacata gttgtaactt ttttctacag gtgctgtatc tgctacgcaa atatttgggt   1500

gaatatgttg aagggctttc tgttgaagct ctcagaataa gtgtatggaa aggtatattt   1560

ctttcataat aatgttcttt tctattgctt aaccttcatc tcctgcaatc cgattccaat   1620

tatttcatgt tgttatatat gctttctatt ctgctgttgt ttgaccaagc acactctttc   1680

cttatttaga caaaaaaata tcaaatctca actttattgt attgtttatt tgatactacc   1740

ctgaagttag atgaagtgaa caagttgtaa cttctttgtt gtatgaagtg ggaatgtggg   1800

ataggtgtta taaagcttgc cgattacgtg catacagaga aacagtctta ttcaggaact   1860

cgaggattgc ctcccacatt ttactcatgt acatcccttg cttggctcta agttgagtca   1920

tataatggat tactgctctc ctgcgctttc gaaaaaaaaa taatggatta ctggattctc   1980

aggcctgatt tggccatgca gtgtctctgt cactcttgca tgtatgctca tggatcctgt   2040

ttctagagat gaaataccca atggtgttct atctccatct tgctttttta accgtaattt   2100

tg                                                                  2102
```

```
<210> SEQ ID NO 31
<211> LENGTH: 2367
<212> TYPE: DNA
<213> ORGANISM: Zea mays

<400> SEQUENCE: 31

tatggataaa taaatccgga catagtaagt gtcacatatg ttatgctaga taggacaggg     60

tagccgcaaa tactttatga acaacggtgt tacggagtca gaatagtata tcaatgtata    120

ttcattttcc tcttatgatg actacttcac ggacttgtat tgtattatta aaaatcaaat    180

taggggataa aaaattgtga ttatatcaat caaaactaaa ggcaatatta gaaacataca    240

aaaatacatg atacatgaca cttcttagtt cttacatcct catgtcataa taccaaaact    300

aagggtcata atatatccat aattgttctt gattagcaaa aaaatcataa ttgttattag    360
```

```
aataatcatg ttggtacaaa ggcttgatta tgtcctataa atgaattata gcccaaaagt    420
taaaagaaac tcaaaacaaa acataaaaga tattaacaaa ctacaagtaa atagttgata    480
aactatatta aattgttggc atagtgtcac tgctgcatgt gcaaacatct gctgctgctg    540
tatccgccgg gttcttacgc atgtatgaga cagtgatttc atgagaaaga ttattgacac    600
gaaatcagaa tccagaaaac aataacttaa acagcacaaa gggagcagca gtgtccttgt    660
tggatacctt cgtcgggaag gtgatagatc acataagaat cactaatcta aaaaacaaaa    720
cagtaagttt aagagcaaaa cagcactagt accttggcta gactgtacat tgtacttgaa    780
tactctgggt gaccaacccc cagaacacgt ccttctatct acagatggca attaaaaaaa    840
gataaattgc atacttcaac aagtgaatta caagcacatt tacatttcca ttgttttgct    900
accatgcttt gatgctttca ttgaatgggt acaggtgtta agcagcagag tgacagaaga    960
tgacaacata tattcgtata gttctgaaag gttatatttt aacctatttg tatgcgatca   1020
accaaaaatg gacaattata agtatggtca agtaagatga tagtatagca taactcaaat   1080
attgttattg tggaatatca cattggtatc aattatgaca gaggcacaaa atttcaagaa   1140
taaatgttaa acataaataa gcaagagcac aaaaagttga ggtgtggtac cttcaaagca   1200
cgctgcaaaa gggggaaac aacaaacaga aaagggtata agaagcaagt tcaaatcttc   1260
gaatgaaaaa aattaagttc aagacttgga atgaaaaaat taagtgcaga aagtatagca   1320
gcagttgaca caaagggtat aatgctacaa tggaaacagt tcaattagcc tttcacaact   1380
tcatgagaaa aatacatcaa ggatctcccc tactgtgact tcgttactaa atttcattct   1440
gtgtatcatg ataatgatgc atatagtgag gactagcatg cctcaaacaa aaagctgcct   1500
acaaaaatgt ccattcgctc acttgcagct tgaacagagt attagcatgc aaaattttgc   1560
acagatttac aaatttctta gattatgatt cccatcaaag gtaacagata ttgtcattcc   1620
tacaaactat tgcatgcggt ctgttttcaa actgtttaat gatattcacc aaaaaagaca   1680
aaaacaaact tttcaaactg tgttgcatag caaaattaca gaagaaacta taaaatctaa   1740
acaaagaaga ataactcatg aggcaacaaa acgttacctc ataacatgtc tgggcttgag   1800
caagcttgag ttgaagatga tagcatattc caagactatg cacagttctt ccaaccctac   1860
attaaaaaat atataatttg atgaattgcc aaatttagga taccatgcat ttggtgtttc   1920
aacagttcaa cacataggat caagcataga aacacattga gatagatagg aaattcattt   1980
agaatgttca tgtaggtgta gcaacgactt acatctgcag ctttatccct gaaacttagc   2040
atttggaatg tgatggctat cgtgctaaaa tgttataagt ttgtcaaacc tataacttct   2100
atggcactgt gctccagttc acttgtgtgt gcgacgggcc tacaactgta atagcactat   2160
gctacaacac atttttgtaa atatgtactg aacctaatct atgactatca aatggtaccc   2220
ctttattggt agggtacatg tcataaaatg tccctggggc aagctgccat gtcccttcag   2280
aaaaagggga gagctagaaa agcatcaagc agaatcagag caaattatcg aacacgacat   2340
tcagggttca tcttccgatt ggaaacc                                        2367
```

<210> SEQ ID NO 32
<211> LENGTH: 1942
<212> TYPE: DNA
<213> ORGANISM: Zea mays

<400> SEQUENCE: 32

```
cggttccagc agcggggccc gggccgcatt tggtggtgat gggcacaatc accccggggt     60
```

```
cggggcattg agaatcgaaa aggccagtgg ccagtggtgc gtgcgcgcac acgctggtcc    120
acgcctgtac ggcggctcag gtgcgtgggg gcacgtcggt tatgggaggc gccacagcat    180
gcatgcagta catagagtgg cgatggcgag cgctgggggc gtcgttgggg gtgggctggg    240
ctgggcgggg gacgctggcc ccggcgacgc cacgcgacgg agcacccgac gagacggcac    300
gcgctagcta cctagctggc tgccccgccc gcccgggtcg gccgatctcc gttcccctgc    360
agcaattcaa cgccccgtcc cgtcccgtcc cgtccctgtg gcctgtgggc gggctgcccg    420
tcactcccgg ccagctgcca cgacgtacgg gcggggggct agctggcacg cccggggacc    480
ggactggagt acggtacggc ggtggcgtcg gcgcatggat ggggtggggg tgggccggat    540
gcttctgctg cttgtggtgg ccaaccacgc atccattggt tcatccgatc cggacaccac    600
accacacctc ccccgccccg cacgcacgcg gtgcgggagt gcgggactag cctgtgctgc    660
gcgtggcgag cgctcaacgc ccgtgccgcg ctgctggtcg ctggtcggtg ccgagctgcc    720
tataggtggt gatgacggtg ctgctctagt agttagttct ctactactac tcctagtctc    780
ctagctcact agtgaatgct ggttgcagat ccgtgtggtg cggatgcagt acggtacggg    840
cgcggagggg atctcgcgca gtggctgtcg gggcctcgtg ggggagctag gggaatggga    900
tctcgcgcct cggtgcggta cgctcgggtg tacggcggca tgtgcggccc ttactcccat    960
ggaatcaaat caatgtccgt cgtcgtgtgc tctggcaccg agcgccgcgt ccagtagcgt   1020
cgtcgtctcg tacgccttgg cctacgccag ctacgcgcgg tcaccacgca cgggaacggg   1080
aagcagtgca tgtacctttg gctagctagt agtaggcatc tacccacgcc atgcattctc   1140
cgcgccgccg tctgctgccc tagctcgtct cctctgctca cagtcaccgg aatgcatggc   1200
gtcaccgcca cgcaagccat acggagcagc gacggtcgat ttcatcaacg acacgacgga   1260
gcgatgaccg caacaaagca cggtcggtcg gtcggggtcc tgagcgcgtg cgtgcgcgcg   1320
caagcgcaag cgcaagctgg ccggcggatc aggaaatttc ggagcggaca gggacgggtt   1380
ggccagtcga caggggggcct ccatgcacaa gcgattgtgc ggccgtggtt cgctggcggt   1440
ggcggtgccc ggcgcccgcc cgctgggcga tcgatcgatc gatcgcccta ccacttcttt   1500
gtgccgctgt tggttgtgtc acgtcctcat ggccggttgg ccgggccccg gtcctggctc   1560
atcctgcgtc caagtgcaag ccgcgagtaa agtaactgtg tcctggccct ggctaccact   1620
ttgtgccgct gtgttgccta gtgaccgagc tcgcccagcg gggagaacag aactgtgtct   1680
tgtgcgtgcg gccagctgtg tggcgcgctg tggcgtacgt cgctctcccg cgccctgtgc   1740
acgtgtgtgc gcgcgcgcgc gtaaccacct ttttctcgtt ctcggcaaca gcccggcact   1800
gcaaatcagc aggcgatcac cgcccacaca gctgatgccg atcgagcgct ctgggcggcg   1860
acgcgcgctg ttgcgctcgc tgttcgtctc cgacaaagaa aaggtggcgt cggtgttggc   1920
tggtcatggt taatcatgtc ac                                            1942
```

<210> SEQ ID NO 33
<211> LENGTH: 1994
<212> TYPE: DNA
<213> ORGANISM: Zea mays

<400> SEQUENCE: 33

```
agggatccta actgcttgct ttcgaatgta acccaacaga ttcacgagat aggctaccaa     60
agagatgttg tttcgacaga caaaagaaaa agagtgggat atcttcgtct ataataaatg    120
agttagatgg cgagatgtta tcagaatacg cttgggattt aagtcacggg cctgacacgt    180
gtgagacaac cttgccatcc tccgacaccc gtccgtccat gtctgcactg acgcctccga    240
```

```
gagcgcaacc tgccaacaca cgctgacgag ttcagacgag ccgagcccat atgatatgcg    300
gccatgcccg tgccgctgta aggacttctg aaccactggc attagtttat ctaaccttat    360
tacattaccc tgaaagatta gcgcctgaaa gatttgcctt gctgctaaag catgcagtga    420
cattgcatcc agcaaaggac agcacccagg tgacaaatgc atttctctgg ggggcgaatc    480
acgaatccat ggcaacctga cgggctgcct gctctgccaa tactggtcac acttcagtga    540
caaagggcat cagaaccaat gcaagaaatg gtcggtgcgt ctgaagaaag atgagagcaa    600
gcaggcaggc cgtcgtggtc tcttaaaatc gacgccggta gacttttatt tttattttta    660
ggtggcttcc caagaatgtc cggcacgcgc cgagcttcca tgccgtggca ggaggcgggc    720
ggggcgaggt gaaaaggagg gcggctctcc tctgacgctg ctcctccacc ttacaattaa    780
aatatttgtt gggtcgattg ggatgatggc gtctgtcaac agctaatgga atcctcgaaa    840
gccaagtctc gccttttttt ttcttcttct cagatctgca gtgcagtgca gcgctcatgg    900
aagccatgtc tcgattggga tgattgctct tgctcgcccc aggatccgga tctttctgaa    960
agttttggga tggactatcg ttggtgtaaa agtatacagc tcactgctct tttcatgttc   1020
tatgctatat gtattatata cagagagaga gagagagagg tgagtttgga ggtttagata   1080
atggataaga gagcttagcg atccagctag gatcagatca tcagaaggcc aaaacctctg   1140
agagccttac acttgacaaa tgcttaagga ctcacgctta aagcttcaaa agacaacaaa   1200
gtggcagttg gttctcaggt aaagtacaaa tagatggaaa caagtcagtt ccatctgatt   1260
gcaacatttg gagggtgaca atgtattttg agcttgtttt ccaaacataa aaaacatgga   1320
caggaaaaca caacaaccaa cgtcagctgt cacttctaac aacaggctac caaacagtgt   1380
gacatataat gcaaggcaga cacgcaccat ttcaacgtac taccataaaa ccagacccag   1440
tgttctgaca gagcactagc acactgctac gtgtgcagtt aattaacgga gctgttgggg   1500
tttgactgca aaggtgcatc caacatccaa gcagcaaatc tgacgtacta gagctcttat   1560
gaacagcacc tgaattagcg tatcatatct gacgaaaacc aaaaggtact gtacctgtct   1620
ctccgcttgt aaatgaaatg aatggtggtt ctggtatttt gatctctgtt tcttggaggg   1680
cgtgatagct ttgcagttag gcaaggcaat caccggggga tgatccagtg cgttgttcta   1740
accaaaaggg cagtaaaccc aaccactcgc tagaggtaca agaagttcag gttgcctagg   1800
cgttctgtcg caactgccaa cagcaaaggg atctgttggt gactgcagct ggatctgact   1860
ctctgagttg agataatcgc ctactatatc ctgtcagtgt caggtccaat aaacagtctc   1920
actcagatat ttggtatcgc aacatgcgga ggatattctc gtcgaaacga aatgcaatta   1980
tccgtggatt atca                                                     1994
```

<210> SEQ ID NO 34
<211> LENGTH: 1898
<212> TYPE: DNA
<213> ORGANISM: Zea mays

<400> SEQUENCE: 34

```
tatatttgac actataacaa atactaacat attttttatg cattgagcgt tgctgactct     60
cgtcaacata tctcagaccg atggattttc gaccggacag agaaagcaaa ggcctgcagc    120
ctgccggggc gttcgtacgt acgcgctact tgtcatgagg cggaacgagc gagagcattg    180
aagcgccgcg agcaggcaac ggatttcccc agcagctata tagcctgtag agaggcgctg    240
aaaagattga tggatcgacc agcactcagc gctcttttcg atcgtgtcgc atgcatcttg    300
```

```
actagtagca gcttgtttgg atcggagctg cagctttatt catgcgtcgt cgtcgtcgac    360
cgctcatcta tctgcgcgca ttatatagca tctgctagct actactagtg cgcatgccac    420
gcgagcacat cattcggtca atgcagcctg cacagctgcg cgtacgtgcg ctgctgcatc    480
gatcgacgat ccgtcgccga ttaattacgt atactctggg aagatagata tactgtaagg    540
ctgatgcctt ttttctgatg agcccattgg atcgatcgat gtgcatgcgt gtcgccagaa    600
ataaagaagc atgcagccaa tcaagctagt gtgtgagcaa cgccgcaggc aggccaggca    660
tgaatgcgtg atgcgtctat taatttgtcc catgcatatt atttactgct gtgagaaata    720
tggcattagc atgcacactg ctccactcgc caatgggcac agttgctcat cagccatcaa    780
cttttgtttt gtgtcagcgc atgtatatat gtggcggcta gctgtgttct cgctatcatc    840
aatatgcagc agagagagat agaatagata gattgacagc tacgtactac tagtgtgtat    900
ctacatagat gtacctttgc agtgcagaga agatacatac aactacgtgc tgatatgcat    960
tatgcatgca acgcactgcg cacctgtcag tcagggtacg tagcagcaca tgcactacac   1020
tgtaccagca ggttttttcc ttggatcatg catctgtgtg tacgtgtggt aaaactctgg   1080
atccgatcca ggacgaggac gaccatatca cctcacctga tctacataca tatgccatgc   1140
agtgcaggat taattattgg cctccatgca tgcatgaatc ggatcccggg acaatatccg   1200
gacacatgca tgcttgaatg gacgtacgta cgtacgtgca tgtgtatatg tacgtgtatg   1260
taattatgta tgtaggtgtg tatacctagg cggctaataa ataaccggat gtgtatactt   1320
gtgcaagacg atttaattac tacttagata tgatcttgca gaattaaacc tactgagatt   1380
agctaggtat ttaggacgac gagatatata cctagctagt agtttgtaaa gccatgcatg   1440
actgcatgag cttctggagc tagctagcca gctatctgcc ggcggctacg ccgcaaacga   1500
cactggcacc gcgcggtcgt cagggctggc ccaggcagca atattgcaag ctgatcctgg   1560
ccattgattg gtcggccggc ctcgcgcgca ggctcaggtg gcttctgcca ttccggtcgt   1620
ggcgcgcacg ggtctgtgtg acgatgatta gggagggccg atggcgggcc atatattatg   1680
cgaccgatat catttggcca ggtacacggg ttaaatttcc attcaaactt tgcctacttt   1740
tttattgtat taggctctga ttccgccagt gatggatatc agtgtcggct caaaatccga   1800
cataattgct agaattggat ctggtttttg gggtagtaat tgacattgat gaggcctccg   1860
ctgattcctg ttctccgaga cgatagcgat agagagat                           1898
```

<210> SEQ ID NO 35
<211> LENGTH: 2417
<212> TYPE: DNA
<213> ORGANISM: Zea mays

<400> SEQUENCE: 35

```
actcaaatta ggcatccatg gtgcaaccca aatgtgttgt caaagttaac ccatacctta     60
gatctagaat tgctgacact agatccatat ggtgtcccat cttcattggt tctaggagta    120
gcatcattga cttatagtga ttgtagttgt ggctcatcat tgctaagaac atcaatcaga    180
gtggaagtaa tgccaaatag ctcttcatgt cgttcctcaa agtcatcttc atcgtcacca    240
cacatcctca acttatagtt gctaggggta ggatcatcgt ctatcacagg ccctttggta    300
cctcaatagt ggctactgca caacaagatg catgtgactt gcaagaagaa gacattctta    360
catgtttcat accaagggga tacatatgta gtcagggtta ggtcatatat tacttgcaca    420
aatacaacaa atgtttatga ccaagatcca tggatctatg taaagagaat aaactaggtt    480
tttaggaata gctataaaaa acagaaggag ggaggaaaac atggaggcgt gcagagggga    540
```

```
gaagactata gatggcccaa ataggaggct tcttaatgcc ttagtgaccg tgactagatc    600

ttctgaggca gcaactagag acaaacatag aggaaatatg tgtgtaggaa aatgaaggtg    660

gagctatgga ggtaagaggc atctttggtg gtcatggttg tagatctagc gatgaggtag    720

ctggagacat ggagagtgga gcgaggagat gaggatgaga catcgatgga ggcaagcatc    780

tatggctaca gggtgatcca tgctagggtt atacaaggtg gggaagggga ctgagtgagg    840

ggaggcgagg atggtatatg ttcaagctaa tatgtgggga caagggagtg acccaagcat    900

gaccccgtag tcatggtagg cgagtatggg cccaacaggc ctgtcgagct aaaaccctag    960

gccatgggtt gtggggattt tgaccatcta taggtgattt gtcaatgttt tgtccattta   1020

ataaaggtct attttacaag gtttttatga ttccactttc acaatatttt aaaaacctac   1080

aaaagaatcc atgtcggcaa cacaaacgac cctagtttac taaacatttt cccaatcaaa   1140

acaaatccta ctagagaaat gcatgtttct tagaagaaat ttgaacataa ataatattca   1200

agaaacaata caatattcct accaaattga cccgacatca tccctcttga atatgctttt   1260

tattattatg ttgttatgaa aaagattttg cagatagttt gaaagacaat gatatatttg   1320

cttaaacgat ggtttgagaa atgatgagtt gtttgggtgc aacaaatcta gtggtagtag   1380

tttggaagac aatgatatat tgctaacact agtgtttttg gagttctaaa gatgacttag   1440

gcagggtttt aggatttgga ttggaacata aaaaatcatc aaatttaacc aactttggtg   1500

aggctctatt taatatcaaa caagtaaaaa gttttagtct aatttgatta tttttctcac   1560

aaaagtgtaa gaagcctaca tgttcctcct tcatcatata agtgtaaacc tagaaatcca   1620

taaccattgg ttatgaactc taagtcaaaa tttgaagaca ttttaactag atttcattaa   1680

aacatgcctt tttaacatga acacctagaa tttccatgat ttatcagttt taatgggcca   1740

agtccgtatg ttccctcatc ttgatcatgg acttgtattt tttggtaaaa aatagtagct   1800

aaaatagctg atgtcaactt tcacacaaga gttaaggggg gctaaatgat catagttaac   1860

tcttgataca gttaggacac ctatgcttta taatcctaga taccactttg gccaaaaaag   1920

atactgaagc tcccttttaa gattaaagta ttcatttggt atcttaaaga tagaagtgtg   1980

ttgttgtgac taaaatagac atttgatcac ctctttttc taaaactaag atatttcgaa    2040

gcttgttcat attgggttta ccgcatctag atccattgtc catatgcttg gaagttgtgt   2100

ggtgggcatt gagagggttg gaaaaaacct tttttgaggc ttcttgctat tatttggata   2160

atttggtgtt acacataata attctgttgt ttatgcttga gaagacacaa aatgcttcat   2220

ttatgaatgc tacacccttg tgaacatatt ggttgtgctt tatatactct attgtggtat   2280

gaggacaaag gggagcagag tgtgaggaca tagggagaag gttcaagtgg taaaaaaagt   2340

gattgtagac tattgctttg agcgccttca actaaaatga tgtcatgaac taacaaaact   2400

ttggatttga ttttctt                                                  2417
```

<210> SEQ ID NO 36
<211> LENGTH: 1589
<212> TYPE: DNA
<213> ORGANISM: Zea mays

<400> SEQUENCE: 36

```
catgattgct tggatttatt ttcgttggca aaataaatta tattcctatg gctttcaaac     60

ggtgtccagg aattccacct gagagaagag ggtgccatgc gctgtgcatg gaaagaaatt    120

ctctctctgt ttttttttca atccaacaaa ggagagtcct agcctaggcg tgtcgttatt    180
```

```
ggtttctcac gtgatgtcgt cctccctgta gcaagcgttt aagcgtcaac gattaccgcg    240
tcgctatccg tcgccgttgc gatgcgtgga actgtggaag gcccggaaaa ctggaatatg    300
ccaagaaaaa aaaactgtca ggatcgtcag gccccactga acctcggtct ccgtcgcgag    360
gaaactgccg agaaggtgta agtaaacgct tgtgatatcc tctgaacgtt gttggatgat    420
caggtcgcag ccacgtgagg atttacgaaa attctcgcgc ttttctttat ctactagtac    480
tactatttcc tcaggtcgaa aacgacgccc atggttgctg ttcgggtttt ttttttcttc    540
tgcttctggc attttgttct cgttgtcgcg atttgatatg gctggagttg gtgtcaggac    600
ggacggggca ggttcattgc acccacgcca cacccggccc tggttcgtcg ttttttttga    660
agcggaggca tccgccatct gatgatcgaa tcgaacgagg ctaccggatc acgtctgaat    720
gcgatggcct acaaaatgag caacggcgat ggagcggatt cgaggtatga aagggccttg    780
ttgtgctaga tggctggggc tgcacccgca cggccggctc tgtgctgcca gcctgccact    840
accggtatgc aaatgcaacg acaaccacca gatcctcatg gggaaaaaat acgagacgac    900
aacgtcatag agaaacactg tagacgtctt ctttctctct ctctctctct cttggaaaat    960
agtcggcaag agcactgtta tgtactccta gtactgtagg acatgggaaa aaagaaagct   1020
ctacgctctc cacagtagat taccggcgcg cgcagttact gaactcctcg agcagcacgt   1080
gcgagcagtg gaatgttcgg ggcaggagga agcagaagca caccacgagg tttcctctgt   1140
cagtcgtgtt gccaccacca gatttcaatt cgacttctcg gcgtggtgct tcatgtacac   1200
gacaatggaa ccaatatata tattttttta tttttttggg gtcttgatcc ggtcggttgc   1260
ggcgtcagag agccgcgctc ctgcaatttc agaatggaca gtgtctgtaa cgccagattc   1320
cctccttgac ccatgaggaa tggatcaaac caatttagaa acaaaaaaaa atgcaggtac   1380
atatgcgttg tgtgtcgacg gcatgcgtgg tgaaatgaac cacgtgcagg ataacgagga   1440
cctgaagcta gtagcgatcg gctatcatca gcacgagtca aatatacacg aatggcgtgg   1500
cgtgcctttt ctgctctcta aagtttcgaa cgcagcagga tcatcaagac tcaaaagggc   1560
gcgaagcagt tagttgttgt gggactcga                                     1589
```

```
<210> SEQ ID NO 37
<211> LENGTH: 2299
<212> TYPE: DNA
<213> ORGANISM: Zea mays

<400> SEQUENCE: 37
```

```
taaagggaga cgggacaaac gagtgtgatc cagatcgtga cagcaaaatc tcgcactggt     60
gaagcgtctg tttcagaagc taccacaccg gtcaaaagta aaatcataag ctcttccttg    120
atccttccgt ggatagttca ggtaaattct aaaataaaag cggcttgtat gtgttctact    180
gttcttatcc acgcgttgac agacagacgg cgttgtcgtg gaaacgttgc cctaccattt    240
ctggagcggt agcagattcc ctttttgcct acctccaatc aacatgcatt ctcgtctaca    300
caaaggtgat atggtcatga tagcatggcc atgcctccat ctcgttgcca tcccttccgg    360
catgagggtg gtgcggtggt atgcatgtta gctgcagaaa ggaggacagt cgttcttctc    420
ttgctgtcct gcacaactga aagatggaaa cctgaaatat ggtaaagaac agcgcggtac    480
caacgtggct ttcgcgactg cgatatgcac ctgtacactg cacccgactg gaaccacaca    540
gccagtagca agtaggcatc atggaatgaa aatcaccgga caattttatt tttattattt    600
cccgaaaaga aaagggaatc acaggactat atacactgcc cccacacagt gtcacaaagt    660
ccattccggc aactgttccc aggctgcttt ctccgacctc ctagcctagc gatgctcgtc    720
```

```
gtacacacat tattccgctg cgctatcttc tcccagtgaa ggaaaccgag agggatttgt    780

cacaggagca caggacgatg tactgtgtgt tgctgcgatc gcaagcgata acagcgattc    840

atggtttgga aacacatggt ggtttgcaag gttatgattt atactattat atattctttg    900

tcagggacgg taatgctgca tcaacacaac agcaacgcga gtggtggact cgcgtctcgg    960

ttgttcgacg gatcgttaga gaccgaccaa atcagcgagg gagcatgacg agacaagcag   1020

atagtttagc acgagtacag gacaagccag ctttgtcgtt gtaacggtga ttacatctac   1080

ctgtcttgta ggacaggcta ggctagagta ggacggatcc aattggaagt ccctatgcat   1140

tattgtgtgg gccgggccgg gatcaagccg ataaggtgat aagtaccctg ttcccacctt   1200

ctagatggtt ggcgctcacg agtaaatcta ggttttgtct aaagcaaaga cggcttttgc   1260

tttgctttct catgtgcgtc ttcagagttt caggcgatat gccgcaaagc aagccgaagc   1320

gtcctgtcta cccgagatat ggcttttttc actgtatggc agatgagaga ttcctagccg   1380

ataaaagtca gaccacttgc tcggtcaaag ctttgtcctt agcatttgta tgaggctaga   1440

gagcgacata ttctgatcgc catttcgtgg gtgcgcgcgc tgctcaacaa cagtcatgtg   1500

ccttttttta aaatctactg tagtcagatc cagctgcagc tgatgtgaca cggtctcgga   1560

gagccaggcc ttaacgaagg gggcccaaca taatatgatc ctaggaggcc cggcaaatgt   1620

tgggccggaa gaactgtatg ccggcgccat tccaatttgg aaattcgttc tttgttctgc   1680

tgaccccaag tctgaactct gaagtagttt ctcaatcagc tcgagctgaa aatattatta   1740

attcgccaac tagcgaggtc tgacgaacga ggcgctgaga cattctcgga ttctccaact   1800

gctcagaggc gctgagagtc tgagatagac acgagtcagt tgcttgatca ttccgctaac   1860

cgctataaca ggatatgtgt agctcgcgtc gtaaaatcgc aacactggaa ctgttcaacg   1920

gggggacatc ggaattaaaa aaaatgtcgt ttgcaccaaa aaaaggaaca aaagagttaa   1980

ttcttttctc atgcgtccat ggtccagtcc atagggctca acaggcggtg ttagttgtgc   2040

acttctttcg tggaacattc ctttcgtggt taactaggag ccaaatagat aatgtccgta   2100

ttgtctgatt ggcaagttgc tgattaagac cgtcagaatt cgcagacgta tattctctcg   2160

cctcttgctc ctattccttt tggactttcg gttgcagttg gaacaaagga cgtccttgta   2220

cggtcagact cgcatcacgc tacttactaa aatgttacgc gggcatcggg cttgtgtggc   2280

tccgttctcc acgcgcgtc                                                2299
```

<210> SEQ ID NO 38
<211> LENGTH: 2603
<212> TYPE: DNA
<213> ORGANISM: Zea mays

<400> SEQUENCE: 38

```
ttgtagtgca tagttgctta attattcatc tttttaaacc agagtctaga gataagtaat     60

cttttgtcca ttgctggatc ttctgttctt aaagcttcat ggcaggcttg gaaattagtg    120

tgtctcatat gtatcttgta gcaggcactc tttcaagtgg cgacaacaga atggatgatg    180

atgtgattga tgatgaagaa gatgctcaga gaagaagatc aagatccaaa aagaatgtgg    240

tgaaggaagc taataatcca gcagtggcct atcaacttca cccacttaaa attatacttc    300

atgtatatga tactgaagat tctggtagca aacgccgtaa actcatcacc ctgaggtttg    360

aatacttggc aaagttgaat gttgtttgtg tcggaattga agattcagag ggtctggaca    420

gtaatatctt gtccaaccta tttccagatg acactggttt agatctgcct caccaggtat    480
```

-continued

```
gtaatttaat tcgaagcaga tggttttgat tgctagttac accatcctta tggaagtttt    540
ggtgtttgtt tatgtaccta cctgtttttg gtttatttca gcctcacagg cctttaatgt    600
gattttagca gggatatgtt ttgttactac atctgtatct agtatcttct tggggcctct    660
catttacgtc agctgaaata gtgacttgtc aattttctca gatggctaag atttatgttg    720
gggaggttcc aaacttcagc gacaaggatt caaggccata caagtgggca caacatttag    780
gtggtatcga ctttttgcct gaagtgcctc catctgttgg ggatgattct agcagagcat    840
taaacactgc tgatttgtca tctgggcttg ctctgtaccg tcagcagaac cgtgcacaga    900
ctattttgca gaggatccgc ttgcggaaag ttgcacagat ggctcttatg tgagtcactg    960
gtctatgttt tttgctgttt gggacatcga tgaaaaaaac cggatggcag attagcctga   1020
gagtgaccgt gtaatttgac tgacgatttt gagctaatga tgcttttgct tcattgcaca   1080
tgtcattctg agttatggca atactatgaa tcatttacca ggcagaaatt gtgaaacata   1140
ccatttatat cttcttcata tgttctctac atattgattc aaagctaatt attggcgacc   1200
ttcattataa tgttattcat gactgttata tacatggcct gtttgattgg tagcatccct   1260
ttgaagtttt cgagtctctt tgattacagg tggcaacttg attatttgac aaagctgaag   1320
tggcctcgaa tagaacataa gaatgcacca tgggcatcac gcaacccact gtgcagtcta   1380
catagttggt cattgacaag ttatcctgag tcatctcgtt ctattttgat gctaagtggt   1440
gctgcaagca atgttgacag tgatgtagag agatctgtga caaactggga agaaactgag   1500
agtatcaggg aggatgggga gcttccagtt gttattcctg ctgagaatga gccaaatggt   1560
tctacaattt tgcaacctga ggtgtcagct gagatccgga gccattctag aggcttatct   1620
cttatatcaa agagtgcaac accatctaag ctaagcatct cacgaagttt tggtagaaat   1680
gaggacgatc ttgatctctt gatgtatagc gacagcgagt tggaggacca gccctgcatt   1740
cttgacgaaa ctgaaaaagc tactagcccg attagagaca gattctggga ggagtatgct   1800
tccaaggaat tcaccatggt cctgagtaaa actatgaaga atggtctaaa agtcatgctg   1860
gaagccaagg taaactatgt catcactatt tgttctaagc cttcatgcat ctctccatgc   1920
tcttgcttct gacattaaga cttatcacag gttaagataa gtatggagta tcctcttaga   1980
cctccccttt tcagattacg tttgctctca gaaaagtctg aaattttgaa gtggcacaat   2040
gatcttcgtg caatggaagc tgaggtttgt gctaacatat cgtgtaacat gttttattta   2100
gtgcatttct gagggtagct cttaaagctc actatcatgc tgtgcaggta aatcttcaca   2160
tccttcgaag catacctcta tcatatgagg attatatatt gactcaccaa gttatgtgcc   2220
tggctatgct gtttgacatg cattttgatg aggaaaacga gaaaagaaaa gtcacttcag   2280
tgatcgatgt tggtctttgc aaacctgtta gtggaactat gcttactaga tcggttaggg   2340
gtagagacag aaggcaaact atttattgga gaggtgctga ttgctcttcc agttacttgt   2400
agagtatgtg cgatcttgat tggtcttggt tgagttcagc attgactacc ctctggagaa   2460
atcatttctg ggcattggag aactgcatat ataacttaag agctgacaca gatccccttg   2520
tttatcacta ctgtgtcttg acagcaatag ctgggaagat ttctctgtgc ccatactgac   2580
tcgagaaact atttacaatg ctg                                           2603
```

<210> SEQ ID NO 39
<211> LENGTH: 1609
<212> TYPE: DNA
<213> ORGANISM: Zea mays

<400> SEQUENCE: 39

```
cgcactctgc actgcgctgc gcttcatgca tgcatgctgg atcgatcgag ctcgatcact      60

tggaccaccg cgatgctcga tcatgctctc cggcctgcag cggccgccca gcatcgcaac     120

aagaagaaga acctgctttc gcagttacca tgcatattca tttattccac cccatcgaac     180

gcgatccatg atccatgcat ggccaccgtc tgatctgagc accaacacag ccccccccatg    240

aatacccatg cacccctacc tgtaccggat catcgctccg tggcttccca tattattctt     300

catttctaaa ctgtatgtac tagcttttac tatatacatc aatatatacc ctggtatatg     360

actacatata atatcaccac cacaccggtt ttttaatcac tagctaatga aagattttcc     420

taagcacaaa agggtaaaaa gaagcttgcc atatatatag atcttgacat gtgtgtactc     480

taaaacagct tgagaaaaac taacccttca gcaataaaaa aggctacttt aaagaatatg     540

cttatcactc gctgctagga ataggaacaa acgaactaaa gggaccggag ctagcgatcg     600

agtacacaat tccttttctt tttttttac ttgattaatt tgaaaacccg aaaggcgcct     660

tttgggtatg taggccggca ggagccttgg cagcatggac caaataaatg tgtatgcgct     720

gctcctagct agagagaaca tgctatcttc ttggcaagtc tctgtctctg atctctccat     780

gcgtgatggc cttacctcat cccatcgtat ttctgcagat cgatcgacta gttatattca     840

gcactaggag tactatatat actatatgca ttttttttgt tacttgcttg tccacataca     900

caatgatcct tgcatacttt gctttctagg cggcctccat tatattgcat atatcatcat     960

catcatcctc atgtgtgggt gcacattata ttatttctat ctccttatgc aacgatgtgt    1020

atgtatgtat gtatgtatga tcaattgatc tgtccctagc tcccgtgacg atatacaaac    1080

atttacacgg cgagttttgg atggatcgat gtgctgtgca attgcaacaa gcacgatctc    1140

ggatgcatgg ggatgcatgc agacagagaa gctaggccga atgaaagcaa gattgcatac    1200

atggatccaa gatgcgattt ttatccttgt tgtttggtgc cgcctgtcct agttgccaag    1260

gcgagcgtat gtatagcatg tacaactgtg tcaggcagat gcaggcaggc aggcatatga    1320

tgcttttatt tgcaggcaca ggcatgcaca ccaccacacc cggccggcac cggccagtgg    1380

agttgcctat gtgatgagaa attttggagc tttccttgcg gcttcggtat ggtccagctt    1440

ttatcatgcc aacgactaac attccctgtc ttgctgctct tactgagatg tataggtagg    1500

taggtaactt ctccaaaata aaatacacat tatgttaatt atattgctcc atcatgattc    1560

atatgattat gagaccacta tattattcta tactatatgt tgatagcta               1609

<210> SEQ ID NO 40
<211> LENGTH: 1794
<212> TYPE: DNA
<213> ORGANISM: Zea mays

<400> SEQUENCE: 40

acttttcttt gaaatcaatt aaggggctca gattttatgt ggcctcttac cttctagaag      60

ataatgagta gtgtaccata gcaaaggcca tgtgatcata ctggatcatc taggatagaa     120

catatgtgtc aagtagacat tgggctatac acttatttta tatactctcc gatgatggta     180

ttattataac aacaatatac taataaaata tatgctctcc tttgatttta tttccatgta     240

tatatagcaa gattaattta caggaggagt atcttaaaat gagcatattc aaacaaataa     300

aaatatacac tttgtccaat cgtcatggac ctgtgactag ccacttcacc tatatatata     360

tatatgcata taaattacac acagaaagga gttaaacaaa ttgtcaaaag ggagggtgat     420

acggtaaaat cgatgggcca acggaaaggt agagcgtgac gtgcacgacg atggctcgat     480
```

```
cgaagccctt ccaccaactt gtgatttatt gactaattaa cgccaagtgt caagtcaaac    540
ccacagcaga gaaagagaga gagctagaga gatctagaga gagagagaga ggggccagga    600
tggatggatg gatggatgga tcaatcacgc actaatgagc tagcgcaacg caaagggcgg    660
gagagagaga gatcgagcag agcattttct tgcatgcaat tatatatctc gtccgtggcc    720
ctctcatttt attttcgcgc gcgcggatgc gggggcgggc gggccaggaa tcgacgacga    780
cgacgcaact atttcatggt cgggcgcttt attttatggt cgaggagatg atgccgctag    840
cttgcactat tatttggaca aatcatcgtg cagcttttaa ttgtcggcac atgacctttt    900
cctccgtgcg atttgtgtgc gtgggcccgc cgccgtcgtc gtcgtccctc cgcccgatcc    960
catgcatgtc tcaagctctc tctacaccat gcacgcatgc atgcatgcat gtgtgtatgt   1020
atgtatgtat gcatcatgta gcagctagta ggctccattg atacatcgtc aagctttcac   1080
aactttaagg aaataagtat gctcaatata tatatactac tactatatac tactaggacg   1140
gagatcgaca aggaaattaa aaggagggaa gagatcgaga gagacagaaa gaaagagaga   1200
tctcgtcgat cgagagatcg tgaattctta attaatcaat tcatcagcta attatcaagc   1260
gttggttcct agtcaaatga gaggatcgat cgatgggcca ctagctagag gtcgctctct   1320
ctatactatg cctagcgcta gttacctata tgatgcatga cgacgaacct ctccggctcg   1380
tgtggcgttc gtttttgttg atcagtcgct gctggagttt ggacgataac taagtgacca   1440
caggagattg gccggccgac ttattatagt tttcagcagc agcagcagat attatatttg   1500
tacgtatata tggacatatg tatggcgaat cttatcactt tcactatttt aatttaacta   1560
gcatatggca agcaacttga ttttttattt taagcacttt caatctgtag tggtcgatga   1620
tacccaccga ctctgcattg tttatttgaa aattttttat gataatctaa gaccaaaaca   1680
acaataagat aaaagcgcat gaatacatag ctaactttcc catcaaataa aataagcgat   1740
tggttccaat acaaatttag agacaaaaat aagtatttta agattctata ttaa         1794
```

<210> SEQ ID NO 41
<211> LENGTH: 1898
<212> TYPE: DNA
<213> ORGANISM: Zea mays

<400> SEQUENCE: 41

```
aggcgacaac gatcgcaacg gattaaggcg ctgagttgag tttcgtggcc actcataccc     60
ctccaaccac cactagaggt cacacatgag caccaaagta ggaggaggag gtggtaacga    120
cgatggcgat gctagtgacg gcaagcatgg cagagcgtga cgccgctgag cgttgcatcg    180
gcaccactca tgaacaccgg cggtggtccg agggtcgctc tagaactact catcaacacc    240
gatggcaatg cacttgaagg caacgtcact tctgagcctg gatctagcaa ggacaacagg    300
tttgttctcc ctattaccac ctcaacagtg ttattgctgc gatcttacaa gccctgcaag    360
gtcattgtgg cccaacttcc tttagtgaag tttgagtatg ctaaacctgt tcctaggaag    420
tttatgtatg tgttggccta aattgcttta cttagggatt atcttattca agatttcgtg    480
gattttgcag cattttacac taagaaatta catttaagga atactttacc aatgctagga    540
ggaaaatttt gagctaggat ggcaataggt tattgtgcaa agtgacatta ccaaacataa    600
ataacgtgag agttaagatg acagatgaag gtttgcttat cgagttgggt gtgcctattt    660
accaggaatc atgttacgaa caagagttca aatagtgagt tcacattgga ttcattcgtt    720
cttttgtatg gacaagctca catagttaaa ctttccaatc tccgcttgac atccaataat    780
gaatggctaa aataattagt gaaaattgct aatttgattt taagggtctt cattctttac    840
```

```
gaaaagtaac caccctatct gaatcactta atcaataagt tgaataaacc taaattaaac    900

cccgttttga atcatatagc gtgccaatat aatctcacta ttacctactt acatcgatgg    960

gtcagttaaa tgtcatatat caggtgaata tcaaatacga tcattttgga aaattgcaga   1020

caaacatgtt tagaagtgtg attgaactta ccaaacttga gtcgggttgg ttaatgaggt   1080

tacgacgtat tgtcatattc agtagcataa ttgagtgcag agtggagacg gctgttgtaa   1140

taagaataat gacatatgtt aacacattaa ccggtgcttt tattctcaac agaaattata   1200

acacacatgt tttaaaaaca ttgtggattc caatggaaat cagttataca gtattagtgg   1260

aactgaatta ttggtttaca aaactttagt gactttctag cagatatgta gtttaatctt   1320

atggacaatg atttttaaat acatatagat gttaaagatg tagaaaggaa ctatatcctg   1380

tcactcactc aatcacttaa gtgctttata aaagagtgaa aaactttgac tcatccttca   1440

tacaagtaca aattggtgat aacatgattt caaaagttat gttaacaaaa atagaactca   1500

tacttttcat tagtgatcta gacaaaagta agaatcaaag atgcaatggt tagtcaagcg   1560

acgattggat ttagatacat ggataaaaga actcccaaca atatatatgt ttatcacata   1620

tggtgatgct tgatatgaaa ctataatcca accgaactaa ttaatctgat gtttgatcta   1680

tacgttttga taaataaaat aaaatgttat aatataataa tatattttgt tttatatagt   1740

attttatttt ctcgttaaag tttatatatt atttctgtga ttgagttatt tcggtgacaa   1800

aataatatat tttgtttatc acataatatt ttcataaaat aaaataatga ttgttgtttt   1860

tttacgtatg cttgagtttg tgtgagatat agtggtat                           1898
```

<210> SEQ ID NO 42
<211> LENGTH: 2594
<212> TYPE: DNA
<213> ORGANISM: Zea mays

<400> SEQUENCE: 42

```
gtgtggcccc ttcgttcatt tgcgcgaaag cggcatgatt aggccgagga atacgacccc     60

ggcgagtctt tttaaaatca tcggcggggg cacgctggtg gatttgcttc cgaggcaggc    120

aaggcttgct ttcgtcgcga tccacatgct aatggcctcc ggaaaaggct ggcgtcgctc    180

ccagagcgaa tcataagaca ggcacaggca caggcacctc ctggatggta taatacccct    240

agccttttc ctactttatc tttttattca tttttttata taaaataact gttgcttttg    300

tttatctttt tagttttcac tagtatttat tatacagtag gacggagtga gtggtatttt    360

aaaacggggt gagtgaacct cgtgacattg accactaccg agagcgggag atgggctggg    420

ccgtgggcgt ggtggccccc accagcggca gcaccggcag gggaagcaca tgcggcgcct    480

gccacaccgc cgggccccgc cagcgtggct gctcatcacc gcggcgccca ctctgcacct    540

acgccgtgga agcgcggagc agcacgccag caccgcagcc accacggaca cgagccgcgg    600

aggagaggac ggcgctctgt gcgtgctagt agcatgcagc ggtaccactg tgactgatga    660

acgaggccca cctggcagcc acgtacggag cgaggggggg cagcattagc attgtgcttg    720

cccgttgttg aaacatggca cgtgcgcaca gtagtggcgg gaaaagggct ctcgccgggc    780

cgcggcgcat gtgatggaga acggactccg tctcccgtgt cagagaggcc gacgttcatg    840

cggagccaaa acagactgcg aagcgaacga ggcgtggcca gtggaatgct tgctttgctt    900

ccctccctgc aactgcaagc catccctcgc catcgccaac gccgaacact gtggatctcg    960

aaacagaaat caagagcggc gcgaggcagc agtacacagt gctgctgctg ctgctgcctg   1020
```

```
cctctgcgtc actggctccc gcaatgaatg gaggccgctg cgccgcgctc tgccagtgcc   1080
caccacgcca cccctgcctg aaaaagggcc ctgccgctgc cgctgccgtg cccacgcaaa   1140
accaggcgcg cgcagcagcg gcacgcaggc gcaggcgcac cgtatcccat ctcgttctcg   1200
tctccgccca acggcccacc catcattcag cacccccctcc ccttgggcct ttggtttggt   1260
tcgcagggaa aaaaaagaac acacacaaag ctcgatagac ggacggtcac gtggcgcgca   1320
ccctgcctgc cgcctcatgc ttcgccacag ccgtaggatg cggtacgcta ataatccacg   1380
tacgatgcca aaagcttctc gtcaatgacc gtagcggatc aggcacacct gagtgcgtgc   1440
gtacggaacg accaccttga tctcgaactg ccttccgaac agcggccgtg cccgtggtag   1500
tgactggctg cctggctggc tggctggtga caagtggcag ggcgtgcgtg tcgtcacggg   1560
ccgggacggg ggaaagggaa acgaccacag aaccgagatg ccactaccgc tagcacgcac   1620
gcacgtacgt acgtactact actactgcta ctttttcgta cgtgcgaaag tttacactat   1680
tatgtactcg tacaccatgg ctacgacggt acaggtgaca ggtctactag agctgagcag   1740
cagctagcgc ggcgcgcagc caggaggagg tgctgctgct gcttttgctg tcaccgtcag   1800
tgctgctgag gtgtgcgatg cgtggcactg tacagcgatt cggttttaga gtcgtccggc   1860
ataaaacagg gggcgcgccc aggccagggc acgccggccg tccgcgatcg gcggtcgtgt   1920
cccgtccgca gcaagggcga ggcgaggcga ggcggcatga gaagtttgcg ttgcgtgccc   1980
gccggatgga tcaccacgct aaccgaatag ggatagaatg gtgtctaata ctgctacggc   2040
cccggatcat ggctcctcac tccccggggt tcaagagaga gcagcagcag cagcagcagc   2100
aggcggagcc gcggaggaaa gaagcattgc agttgcaggc aggccgggtt gcagcacaaa   2160
agctcttcac tgacgaaaac taatgaagca ggaagcatgc aatgcaatgc atgcatgacg   2220
cgcccaaagg tacacaattg ctgcagcaca gcaccagcaa cgccaaaaaa aaaagaggct   2280
cttgtcgtga cgccgagttg ggcccgcacg ggcgggtgtg cggccaccag actagagaga   2340
ggggccgagc ctttgcactt gcagcctttc cacccacgcg gcccctcacc aagcgcccgg   2400
ccagaggatc acgttactgt actaggttca tgagaatatg acattagaca agtacgtggg   2460
taacacgaga gctgcccgat gcgggcaacg ggcaacgggc aacggcccag gcttttgctc   2520
gcagcctcgc aggttttttt tttaatagtt gcggaggatt tgagaggcgg tgtcctcgat   2580
tctctctatt cccc                                                     2594
```

```
<210> SEQ ID NO 43
<211> LENGTH: 1814
<212> TYPE: DNA
<213> ORGANISM: Zea mays

<400> SEQUENCE: 43

gtcaactcta taaatcaatt tatagggatg actagaaatc attttccata aatcggggaa     60
aaaaacagta ctacctataa atcataaatc agaccaaaag cagcgtgtct ttaatccgga    120
ttttttgtgc aaattaacta cgcgcgaatg tttcaaggct tgagcgcgtc tcttctaatc    180
attccactct aattctccaa ggtcacttgt gagttgtgac taatatgtag atatacattc    240
cttggagtta gtggttcaaa gcgagcagaa taactacatg catgtttcag ctatgttata    300
tttaccagct accataataa gtagctgcta gctagcctgt ccatgctctt cagacacttt    360
tggaggcaga ctatgacatc actgaccagc tgaagtgttg atgggtggcc acttttcctt    420
tcaacaaagt atcaggtttc cagagttgag ctgaaatgat ggtgaacgac gcggcgcaac    480
gtctcctttg cccactttat agataagata tttcttttac cattcaagca ttcatcagga    540
```

```
tgagtgacac ttgaactgag cagcaatctg caaaaaaaac atgagttcaa ttggatctct    600

ctctctctct cctatcgaga tggcagctga taaaaaacaa gaaaagcagg aagatacttt    660

tgtagaaata aagtatttcg attgatgaac taaagaccaa gtttaaccaa tctctgcata    720

ttggttggta ggaaaatcga atgatatcaa agcaaaaaat tcagataaga aagtagacag    780

caaatcggta gcttttttg gttagtgttg tcctaatagg cagcatatct gaacctgttt    840

tttccaaaat gccactttac ctgatgcaaa ccgatatgcc tgcctgcttg cttgtgggta    900

tcaaacttgg tcggcaggat gttcctcagt tttcttggcc ctttgacgct ggctaataat    960

agtaccaaca ataaatggac cgtatgaatt catcgtccat gttgtggtgg tataggattc   1020

tcaaaattgt ttcagattct gacattttct tgtaatggca aaatgtagca atgtactact   1080

ttacacagct aaggaagtga ccaatatata tatttttaat ttctttgtct catcctaaaa   1140

tctcctgtct tacaagctct agtgcatata ggcatacaat actgaaaagc cactacacac   1200

aagaatctgt tccttgtgaa agattgtacc ctactctttc tcatagttgg atgcacacac   1260

caattgcatt tcattagatt ctattaatta gatggtgtac tattaagaac cttcgaccag   1320

tgtatatcat gtactgcatc tattcttcca gaaccaccat gggcagcttc ctgtcaagaa   1380

caccattatt agttactggt aggtgctagc ttcgacattc cacgtgagca gagcaagtag   1440

ttctccatgc tgcatttgtt ccctgccgga gatgctaacg agatcacaag atcaggtgta   1500

atatactgag tataaacgat ttatggttct cagaattttt tcagtgctat ttgaagataa   1560

cgaatggcgt agtctgtttg atgtgtcaac agttcatcct atatacaatt tcccagttgc   1620

atggacatga taaatgagta ataatgccag ggccataata tgtcatagaa taaactcttt   1680

ttccccttta atgactaaaa gtctatattg tgcacacatt tcatttgact gctgattgct   1740

gatcatatat ataaattcgt tgcctttttt atttatttag attttctttt atgggaacaa   1800

ctctgtgcat aggc                                                     1814
```

<210> SEQ ID NO 44
<211> LENGTH: 2071
<212> TYPE: DNA
<213> ORGANISM: Zea mays

<400> SEQUENCE: 44

```
gtctatacat gtcctagttc ttggctccat gcatgccctt atagttcctg gctcatcata     60

tactactgat cgatggactc ctggatcgct gaagctgctg cgtgtacgta gttccgtgca    120

gcacgcatgt tacgattacg actttgttag caggtcgttg ttatgcgccg tacgccgcgt    180

ctaagcatat atagtcagcg tcgtcgtccc ccctggcaaa ttatttggtc gttcttctct    240

gacgatgacg aaacacgttc aaaatgcatg cgcgtgttcc gtcgcgcgcg cgttcggtaa    300

acgcgcacgg gaacgacgta cgcgagctcg tgtcccctcg atcattggat ggtctcgtac    360

gtaagtttac tacccgacgt tgcaccgcga aattcaaatg ccagtgccga actaagtttg    420

gctgtcatac atcgtcagaa ggaaaacaga acccccaaaa aaaaacataa tgaggtattc    480

ccatcagagg taagcagctt aggcggctga gttgaatttg actgaataat atccatgctt    540

gtgtgtgcgt gcctaacgca ttgtcgtcgt gttctacgta cgctgctgca tgctactact    600

ttgctactaa aagtcatgca tcgtctcagg tagagctagg ctctaataat gtactagttt    660

atttgaaacg tacgtccggc atacggaaca agtagtaata atgagcatca gatcgcgtgc    720

aatgcagagg atagcagaat atacttgtat gtagctatgt ataggccacg acttgcgtaa    780
```

```
agctctaacg gctgttcacg accccaacgt cgtacgagag gccgggaaac aatcgtccag    840
caggccggcg gccggctagc tcggttgccg taagctacga ttcttagcac attaatatta    900
cattacatgc atgcatatcc cgcaccgctg tagcatctat acacagagta ctccacatct    960
acatctcctg gaggtcgatc gacctggcta gtactagtag tacacaggcc gcgggcgcgc   1020
gcgtttggtg cacgtcgtac acaaccccct tgaggaataa tcgcatgcct cgacgacgac   1080
gacgtcggag tcagcggcgt ggcaacaatg ttggttagtt gggcaaatta aattgaactc   1140
ccgaagagag acggttgaac tgatgactga gatgagtcgt cgtaaacgtg tgtgccaagg   1200
ttgggcaggg ttgggttggg ttgggccggg cgtacgtata cgtctctgat gcatcgtccc   1260
cctaaggacg gccgacgaca cacatctgtg acagtaactg acaaggactg catcactacg   1320
acgatgcacg cgtcattcgg attgtctgct tcagaataag cgagagctcc gtgccgtacg   1380
tgaccaaatc aaagcacagt cgctaacccc agcccagatg ttctagttga ctaagtgttg   1440
tttacttttt ttccccctt aagtagatcg agtaacatcg ttatcgcgcg tattgacgga   1500
cagataacca taagctaagt ctatataagt tcggccggtg ctgagctact gcaggtagca   1560
ggatcgatat agcccaagcg atcgagaggg cattaattga ttgtgcttag ttttgtcggt   1620
tgccgctttg ctctggataa ctacaactac tccagctaga cgtagatcga cctagcgaga   1680
gctgtggact cgagagcgag atttcaactc ctgaacgcgc agtctgtacg tacagctacg   1740
gcctatctaa catgcctttc acttcattcc tcttctggat ttcatctccg caagtcccct   1800
gggatttgct cgttttggtt cagaggattc gctgcttaca cgcacggtcc tggggttaac   1860
ggagctcaac acagtagagt accatctctc attctctctt aatatcatcg gcatgcctta   1920
caactaagag tctgtcgtct tgaggcggtt gatataaaac attcaccatt gttaatagcc   1980
tattactcct gacgacagag gctatacctc agtctgtaga gccatggtgt agcctccatc   2040
ttggcatcaa caccgagcac cagtattatt t                                  2071
```

<210> SEQ ID NO 45
<211> LENGTH: 2556
<212> TYPE: DNA
<213> ORGANISM: Zea mays

<400> SEQUENCE: 45

```
caaattaaat taacgctaac aactgattgt aatcagaata aaacgcacca cacgtaatgc     60
aagtcgacat atgactgaaa tattctagaa tagattccct tttgagacat tgtcgtgttg    120
ttgcagagtc caccaccaac catatattta ttcagaaatg ctgtcaaatt aagcaatagc    180
acgacgtgtg aacgatcaac atgactatga tgcaaagatc caaggtgcgg tgcgcgcatc    240
ttcctcctca aactggaact cgacacacct gccaactgag atcttattag ttgaactttg    300
agcccctgag acgactcatt tggctccaca aggacaatat cgctgctagc ttgttaacaa    360
caagataaga agatcagacc agtgtctgga aagatgcaaa tgttcagtga ctgtgtcgat    420
gaatgatttt ctagatgtga ataataaaac aatttaacct aatcatatca taacaatatt    480
aacaaccgac atgtaggccc agcgccatca tgcatggacc atcggccatg ttgaagtgtt    540
gaagcaattt cattggttaa agtaagctta taggtcaacc acagcaacat ttcaacggtt    600
tgtagtagga ttttttttt ttggcaaagg tgtgtggtgc agaatttttg tgccagtacc    660
cttgacgcca ccgcatgcag gtgccatgtg tcggaacgtg gctgcgaaac aaacataccc    720
caataatccc caaattttca ccaaaatctt tcaataaata gcgcctttct tcttactttg    780
ataagagaaa tgatccaaat ccaccctcga aattcaacac ttttgccaat ttcacatgta    840
```

ctctccctcg ttttagtcaa gcaaattatg atacccaacc tgcaattagc tctagcttgc 900
ttgctgtcgg aacatgtcaa agatccgaca aaagtatata aaatgttcta tgttgacata 960
gtctatggcc ttcagctgtg ttcttggcta caagcatacg ctcgagagat taattattcc 1020
ctgctttggt ttgtatatag tttcatttct tctagaagcc tttgtttgtt gcatctaaga 1080
cgaagaacca acacgtggcc tctgtagtta tttagggtga ggcaataaaa aaaaatttat 1140
gcttcgaacc ttcttctgta gcctccctgc tgcatgccta ttcgtataca aattaacatg 1200
atgccaaagt ctgcataagg ttttccttca aaaagaaaaa aaaaacaagt ccacgtaaga 1260
ttaacagtga cagattggat atattcagac acatttacag gtgtctttgg tttagttgcc 1320
aatgacatga gggtggtgga gaaaacaatc cccgtgatca tactaccaac ccctcttttt 1380
cctcacaata attgactttc accgtaccca gtttcggcta aaaaataata tttttgaaat 1440
gccagccaaa catcaaacag taaaattcac ccaccaacct aattgtgctt aaacaaatga 1500
cctactaact catagctaga cactacaaaa ggatcatgct gtcgctgttg gcggtatatt 1560
ctccagaagg ggttggacgt ctaagcatct cacatactag accagctagg ctgtaatcac 1620
cgagaggagg aggggtttat ttctttaaac catgcatgcc aagaactgaa gggatggaat 1680
ggaaagtgca tgcatccagt caattaatga ggcacgctac cttatccctg ctacagagat 1740
ttgtttaacc gtctcgatct gtgcaggtta attggtctgc ctctgaatat tcagaatcat 1800
gcaacgacga tgcgtataca gacacacatc atcatgcatg cacaaagaag ctagacagca 1860
ttaaactagt gcaataatga ttccagcata ttttaactgc attattgtgg atccagtacc 1920
gaccttcccc aggtgctgct gtggcgagct actatacggt gggtttgaca ctaattaatt 1980
ggatcgagct acgttactcg atcaatacgc atcgtcgtgt ttgtggaggg gttaaataaa 2040
ataaatacgt acggcagtgc catgattggc cgttttatat ataatctctc ccagtcgtaa 2100
catgcacgct ggctggctct acctctacct tgcttgtctg actgaatttt agcatgtgtt 2160
gtggtcaagt agatgatgca agtaattagt agactgtaaa gcttagcata caatgtcgtc 2220
aggtggttag tgtgagagcc tcttacacgc cactgaaagt gccaaacaaa ccttcggaac 2280
ctcggccttt tcgtttggct aaattaaaca aatgtgtggc cttcattaga ttggatcgta 2340
ctacgtgggc gataaaggag acaggtagcg gaaaccaacg acgcctttgg gtaaaaaatat 2400 aaacgaactg ccccgaccct tgtttctatc atcgtcttat aagtatatac atgactttgg 2460
ttctttaatt tgggggtcc aaatcaactg gttgttgcta catctactac taactcgacg 2520
atcaatgcaa tggaattcag tttaaactgg caagcg 2556

<210> SEQ ID NO 46
<211> LENGTH: 1577
<212> TYPE: DNA
<213> ORGANISM: Zea mays

<400> SEQUENCE: 46
aaggaccaac aacaagccaa aggaactaga tcactgacct cccattgcac tgaggagggc 60
tttgcgaagg gtgctcatgc acatcactct atatctagga atgagatgaa cacatgaatg 120
tttcaatcaa atgaaaaagg atggagagta ataggatggc aaggagtatt ttttgaaatt 180
tctaggcgtt ttcgaaataa tcataaatgt tggtggttgt gatgcctttt atgtaaccgc 240
gtagaagaag agagagagat agctatgctt atgataaaga agatgtgtgt tattgtttgt 300
atatgataat ttttatttac catgtgggta ttgatagtga tgcctacatg atgaatcatt 360

```
ttgaggagca atgcttgttt tcattattgg ccccaatgtt ttccaagatt ggacattatg    420
gaaggccttg acctcccacc ggtttattag gtaggtctcc tttatcttgc actaagactt    480
ctcatgttca tatccttagg cattggacat atggaccata caaaggtgaa aggaccatca    540
agatcctatt taggtccatt aaatatatat gtagttagaa gtagaagtgg caagtcaaga    600
ggactggtat gtcatacgtc acatgggtgc atgtcacatc ggagtgagct agcgctatca    660
agaagaaaat aaaggtaaat gtagcaatgg gtatattagt ctactatttg tacatgtgat    720
cctgaaagag acattaatat gttggcctag attggacttc ggtcttatag gacatgataa    780
gtaataactg aaactacttt cccgttccgt ttatcttatt tttcttcttc gcttcttcca    840
tctctatccc tatccctatc cctctctctc tcttttaaat tcttccccaa atatacatat    900
atatccctat tgcatccctg gatcgaaagg gacatgacaa ttcgtatgag atctaggctc    960
ttcatgcagg taattccttt attaccctct tggtcttgag tgacaatcat cattaactag   1020
tgttttcatt agacttgcac ttccattcca ggtctgtaat ctagtcattt tggactagag   1080
caattcacca tcacttgtaa ttggtaagca acttattctt tttaatttgc actatcatgg   1140
aggatgtgga agcgtgattg tgcaaattat ttggggacga acactcataa agaattttgg   1200
cggagttgat atgctcaagt aacaaatcat caacatcgac atcaattgta tcgactaggc   1260
catttggatc aaccaagtgc aagcaaagcc ggacttgtca atgtcttttc taggaaattc   1320
tcagcaagaa caacttcatg tcatgcatga tcttaaggag tcccttggtc caagggtagg   1380
acctctagat aaccatggtc cacaattgat gggaccgcct cctcaatttc aacctctacc   1440
atctcattct catatcatgc aggtgaattt acttgcctct tcttaaacaa gtgatttggg   1500
ttttttattt atgcggctgc tgtatgcatt gtgatgcttg ttgggtttac taatgcaagc   1560
tacggtgggc ttgtctt                                                  1577
```

<210> SEQ ID NO 47
<211> LENGTH: 2006
<212> TYPE: DNA
<213> ORGANISM: Zea mays

<400> SEQUENCE: 47

```
agagaagtgc acaaacgacc agctctccag ttcctatttg caggaagaat ggtctgaaca     60
gaacctctac aaaacctgca atcaattgaa acagaatcaa gaacccatcc tttctttccg    120
aaaagacact ttagaacagc aaatgacttt aaaagtttgc caatttgtat cctggacttc    180
caatgtccac aatatcaata cttccacagc caaacttatt gcagcttata acgacagtta    240
atcacttgaa catctgatag accactgatc tcaataaagt tgttcatcga tacagtgaat    300
tttttgtaag ttgtcaaaag aactcaggtt atagcatttt ccagacaaaa ttctagccat    360
actcgtaagg ggaggggggga gggggatcag ccagttggaa ttgatctttc ttcaaacctc    420
aacaggcaga aaactaccaa gtgaatgttt agattttaaa ttacacagat cgaagggagc    480
aatctgaaaa ttgcatggcc aagtagtgta tgatgaagtt ctgtcctaga aggtttctgt    540
gttcgcagag aggaatgggc aaatggctag aactctaagc tacattttaa aagatataaa    600
gttctcagta ttcacacata catttttcaa cagaaactgt ggataaatgc tagagtaaaa    660
tagtatgacc aaatcgtgat ccaaaaaaca gaagttccaa cgaggcatac attttgcaac    720
catcagaagt atatacttcc ttcagattcc gtatcctctg atcaaatgca acagactttc    780
ccgtttcatc atctcgaact aggacctgtc tctctgcatg gccctgaaat agtgattttt    840
tagcaacatg gtcaagaact aatattaaaa cagaagcatc tgaaccaaaa gaaaggaaca    900
```

```
gttattggca tctataaata aagaaattag cgaagtgaac cttgcgcatt acctgatcca    960

ctaacacatt taatatagta ggaatttccg aatgaataac tgaaagtact gttgggtgtg   1020

gcgttgacgg aagcaaatga tctggaatgt caaccctatt caaagatgga ataagaattc   1080

agacaaccaa atatgaacaa aatagaagac cttattgtct taccgtggtt tagtgaagtc   1140

atatataata atttgaaggt tgcgatagtt cacttctttc gcacattctc gtaaaacgag   1200

tgaatcctta tgacatgaga caatgaaagc atctaataac ctccctaatg catattcaat   1260

tgcaacagac caggaatcgc ttgccagttg ctgcatcaaa gcaaataacg caatgagtgg   1320

aacctggagt gaacaagtaa agtaatcaaa agaaatacga caacaatcaa ggatagttat   1380

gccataccag atgatatcct attggaccaa taggagggca tttgaattta ctcatgtgtc   1440

tctctactga tttatagagg ctcggaactc tatctcctcc gaaggccgtt agctgtaaag   1500

gagcatcact agttgctaca attagtttat acaaccaaat agttgttact taaaatgtct   1560

gaaaacacag cattaatata gtagaaatat ttcatgctta atgaagcatt ggatagtact   1620

ttgttttgtt ggcgccgtcg tatatcatca atttgacttc tcagttgatt gatcctacgt   1680

ccatcttctt ctatctgcaa agtacataca acagaatata cagtacaaca ccacaaggat   1740

ccaaaacaaa ggttaacacc ataaacatgg cagcgcggac aaaattacat gttgtgcaga   1800

taattgtgac tactcgaatt attcccctat gctgaagcca tgtcgctaac cagggaggag   1860

tatactactg ggttttggtc agggctaggg gcatctcatt tttccttgcc cttgggcctc   1920

agcagtcagt agaggtcctc ttttcccctt ggttaggtca aggttgttcg atgttttcaa   1980

gggcgcgtgt gtaaccaaac acccta                                        2006
```

<210> SEQ ID NO 48
<211> LENGTH: 1795
<212> TYPE: DNA
<213> ORGANISM: Zea mays

<400> SEQUENCE: 48

```
ttgtatatat ataaaaaagg aggctttgtg gctgacaccg ccatccccca aataaaatag     60

gcattcgcag ctggctgaag agaggggatg tcgcattaaa aaaaagatga aaatacctct    120

ggctaaaaaa tgagtgtcgg tgtatatata atactaaaca aaaccagatt ttttttacaa    180

tagacttaaa tcaaagaacg tggtgtggga cagacaaaat cactacgtac gactacagag    240

tgtgccatag acaaatggct caaaaaaaaa caaaaaaaaa agaaacaaaa aagaacgagc    300

gttgcgctgt gcaacacccg ttccgcttca atgccctgcc gtccttggct cctccttccg    360

cctgttctgt tctgctctgc tctgtttctc tctccctctc cctcaggcac tgtagcaggg    420

gcgtgtgggg cgagtccctg tgcgcgcgcc tacgacgaac gagaggacac tgccacttcg    480

aactgggaat taaatttgca tggggccttt tggcccgtgc agatgggagg ttggggttgc    540

cgttgccttg gtggaccacc accacgcccc ccgtgcactg tgcgccattc atcaccatat    600

gacctacagt acgtaggagt agggctttac tttgtcatcg caaatccagg ctgcactgca    660

ctcgacgatc atctgctggc ggtttagcaa ctaacgacgt acgggcgaca tcctttgatc    720

aggccgcctt tgtgtagcaa gcacagattt attaattacg tacgtatacg caacagcccg    780

acagatgaca ctgcttctta ctaattattt gatgcacaca tggtgtacca tgcgaaacgg    840

gaaaaaaagg ctgatagatg ccaacgagtt acggacgagt acgtacaatg ttgttgttac    900

acaagctatt cggctctagg taacaaacta gtacagcgag cagaacatcg cattaaggat    960
```

```
ggcagtaaaa accaagcgca caactttcat ttcgtctctt atttattcat cgcagtatta   1020

gtagtgtact actgaactag ctagtgttct tcgtaattaa tattttattt gacaatttaa   1080

tcttagatca gctgtgtgtg catcaagaca cggggaccac gccgaaacag ttcccggtcg   1140

agaagcccct gtcgccatgc catgcaacgg tcgtgcgtgc gagaggcgaa tcagtggacg   1200

acggccgtag tgtcagcaag agtgagcaag cccctggcgc cggcgtagcc agcggcgcag   1260

gctaaagccg cagggcaggg acgagacgac tagtacgtac tagcaacgaa gcgagcgaac   1320

gcgcgcccca aagtgcaaag cggccaggcc aggcatggtg cgttgggtac gcagggtgta   1380

attgcgagtg ctactccgcc taggactact ctactctact actactcgtc acggctgtac   1440

tagcagtaca ctgtagcaca cctggattac gggctaccca gggctggaca gggggcaggc   1500

agctgtatac taggtgttta acggaacgga aaccgagcga tgattgcctt gattgggttc   1560

gggggccttt gaccacctgc cacttttctg acttctgtct ctctctctcc cccatagagg   1620

aaccgaggag ggagagaggg acgcgtttgt gtcgcccgcg gcccagtagc ccgttggacg   1680

gatgggctgg tttgggaggg ctgacaccga cgttacgtaa gtccaattgt ctggacctgg   1740

ggcctgggtt aggtttcgac gacaagatta ttcagctttt gttttgttaa gtatc        1795
```

<210> SEQ ID NO 49
<211> LENGTH: 3690
<212> TYPE: DNA
<213> ORGANISM: Zea mays

<400> SEQUENCE: 49

```
ggagtagttc ttgatattgt attgtgatgg tgttaaagct atatacaatc atgaagggtg     60

taattattgt gaagacattc actttgacgc tggaaggggg tgaaaaaaca tgagctttta    120

tacgtccttc tttctcgcgt cttttaatgg aaaagattca gactgtagat ctatgcgacg    180

atccgatgat gccgttactc caccacgcac agcagtcggc agagcagagg caggcagtat    240

tgcagcccag cacacacgca ccgctcgttg cgcaggcgtg tggcgtccaa tcacccccgt    300

agtagtgggc cgtaacactc tccgccacag gacaggctca ttaaccccgg tcacactgcg    360

cttgcacagc acgggcacgg gcacgggaca gcgcgcggct cgcatcgcat cgcgtcaatc    420

gtttcgacgg gccgggcggg cgacgcccac acgccacgcc cacgccaacg agagccggca    480

gcgtgcgtgc tgtcagccgc gataactctc cattaactaa cccatgcgat ggccagctcg    540

cggctccggt gtcaacctga caaaacccgt ggcccggtcg gcggcccgcc cccgcccccg    600

cccccatcgt ccgtcggttt tggtcgggcg accgagccgt gcccggtatg ggagtaggcc    660

cggccgaggc tgcgtgcgag acaagggcgc gctcggcctc cggcctctgg ctccggctgc    720

gcgacctgac gcggataggc agccaaaggc gtgcgtagcc gcgtagggct gtttggattt    780

ttcatggtag tagcttgtct gtctgaggta gccaggggtg tagatggaag atggtccgtc    840

cgatccacaa gggatgatga tgatgacgaa ttgatgagtt caaatgtcta gctacctacc    900

tacctaccta gctagccggg tctgctggag cctgcacatt gcatgcaggg tcgaggggaa    960

ccgtgccgcc gcacgtaccg ggtgtacatt gttgaccaaa acatggcctg cctgcctgcc   1020

tgccacgtac tatcgtgagc ttagcgaaac ttgttcctcg aatcaatgcc agtgcctgtg   1080

cctgcactgc gactgcgagg gagcgagcga gcagcagtac ccccctcgtc acagtacgtg   1140

tcgatatgcc gtatgcgtgc tagtgctaaa aaaacactgg cagcgcatat aactactgca   1200

ctgtaacttc tttcgtctgg aatagttagg tacctactgt gcacagaatc tgcatctgca   1260

tgcgcgcgtc cttgtttttt gatgggtaag tataaagcat tggtacactg gaaacactaa   1320
```

```
tcaatcgatg agcaccggtc cagtgatgac atcttgaatt ttttttcctc cctccaaaag   1380
gacggataac tcctgctcgt ttactgtacg tagatgctgt agatacaatg gaatcgtgga   1440
gcatttgatc agacagacgg tcctccacac gcgccgccgc ggttttgagt tgactcctgc   1500
cccccccggc agaagccacg aggcccatcc acgccacggc catcgagtcc cgccggcatt   1560
ggcagttgga tcgatggcac ggcgtcccac tcgctcccac ctcattcatc agtgtcagcg   1620
tgcgtgcccc catccggcca acaccaacaa acaacccaag gcaaaccaaa ccaccctcca   1680
gagtccccag ctctgaacct ctcccatcca tccgccggcc agggacaaag gccgcccgag   1740
gagccagaca gccccacggg cgggcaggct gcgggcgcta ggcgatatat atcccactgc   1800
gcacccgcac agcctgcctg cccccgcgcg cgcaacaaca tccgccgtgc ccaggagacg   1860
ccgaggcacc gctccggcgc tccgcctccg ctccgcaagt ccgcagtccc cacaccacac   1920
gtggtagggg cgccacaaca actgctccgc tggctcgcct cctcctcctc gtgcgcccgt   1980
tctgccactg ccaggccggc gcccgccagg gacaggacag catgtggtca gtgtacagaa   2040
ttcacttctc cgtgccttct cctctcctcc ggggctacct gggcactgga ccagaacatt   2100
ctgaagccca gcctgtcctg gcccaggcct ccaacggaac cggacccgga gcggcctact   2160
tggcctagcg ttaatttgtt ttttttgtt tgggctccgg taaatcggat aagaaaaatt   2220
accatcctgg atttaaaaaa aatactatcc ctgatttcgg atactcggta attaaaattt   2280
tactactgta gttcgatgta ccccgagttc gcataaaccg aaacttgcat ggaattgcag   2340
cagtaattta tgtcatggaa tttatgtgcg ctaccaggtc atgaagttcc tctcctgtgc   2400
aaaaggaagc aaaccgtacg tacgtacgtg tgtggcgcgt ggcaccgcta gcgctagcgc   2460
tagccctgtc cggcgtcaca tgatgcaaac gaagtggccg taactacact acagacccct   2520
cgatcggcac tgttctttcc atccccacct ccgcgtgcca cgccgcactt ggcaaaacgg   2580
aatgctgccc tgccggctgc cggtacctgt atttactacc gccaccattc caccaacaca   2640
ggccacagca cagcacagca gcatggcgcg tcgctgtgca ctgtaccgct acgcccccct   2700
gcggcctgcg tacaccacca tcgagggcat gccacgccga gaagcggtgc tctgctagta   2760
aggaacgggc atctgatccg acggccgggc ggggcggtgt gcccggtacc cgtgtcgccg   2820
catgcacgta gagcgcttgc gcttccttcc aaccagcaac caccgcacca tcagggagta   2880
aatgcccatc acccgcgctc tcacctcttt cacggtcgcg gaccggaggc ctacccgtat   2940
cggcgtacta gtgcgtctca caaaggtgtc cgggcgcgcc cgcaggccta gagcgagggc   3000
ctcgtaacgc tgccccgaaa ccgaaacgtg ggcgtgtatc cctccagtcc agcgggattg   3060
catcacctgc gccggcgccg cgccatgcat ggcatggcag caccagctgc tgctgcccgc   3120
catgcatgca tggttgattg gcagcttgtt ttgttcgtgc ggtcgtgcct gtgtgtgctg   3180
atgtcgtcgt ctacgcaata cagtacgacg gagctagcta agctaccagt agactagagt   3240
actccgctcc gctgcacatt gacgattttt gattttggat cgaatattcg aatggcattg   3300
gcatggtgtc gagtacgtag tgtacgtagt acttcttttc ttgaggatag gctgctctgg   3360
ctctctcccg aataagctcg tgtatggatg gcagcagggc acccccatcg atcacctgcg   3420
gtgcggaggt acgggcgggg ctgacttttt ccgcagaacg aaccggcacc aagatttatt   3480
acagaattta cagcaagtca acactttcac tgtgatcgca ctgtccgtga attaacgcgg   3540
cagctgtacg agcgttcctt tccgtttccg tttccgtttc ggctgcacgc ggcactgtga   3600
catgcgtatt caaggtctgc tagctgtcgt cgtccccttc cgtttcaaat tgcaaatcta   3660
```

gtctatatat acaagtcaga cggaatatat 3690

<210> SEQ ID NO 50
<211> LENGTH: 1742
<212> TYPE: DNA
<213> ORGANISM: Zea mays

<400> SEQUENCE: 50
ccgaactgag agagtaatta atagcatcac agtgtaatat acgagtataa atgaaaactg 60
cgcgtgggca gatctaatca tctaatacgc ttaggcagaa ggtggttaaa cagaagcatg 120
atgtgcatgt taccgaccct gctgcgcaga atgggccttc gagatttaag gaaatccccc 180
atgtaatcaa tccatcatca aactgaggat tttggagcct tgtgaaacca gcatctaccc 240
aacagcaagg aagcaagcag gctagctagg gagtagcagt agctagcagt agcccttctg 300
gttgctggtg cagcatcagc gtccacagta gtccaggttg ggtctggcaa catggcatta 360
tatgtcggcc gtgaaacatt cttggggtgt taatgtgtta tatcccaggc acaagcacaa 420
cacacgaacg aggttgccgc gtactacgta caacctggaa aatggcttgc cgttgtggac 480
acgcgtagta ataacgcgga gcaagctctt gtaatggaca gctgtaaact gtaatggaac 540
tgttcaaatt gcactacaaa tggaacccgg ccgaggtcgt ccaggcagga tgcctggaac 600
agatagatac atgcagagta cgtaagtgag tactaaacaa atctgaacaa aggaaagctt 660
tcctgaaagt cgccaggcgc aggcgaagta ctgatgaatg gcgaacacgc aagtgcttgc 720
tcccacagac ccacactccc agctgatcgg cagccatcag ctcagaggct caggcgttct 780
ctaaaaaaaa tctgccaact atatgggaat ccaaggcctc gctgcattgg agagcatgga 840
tctcatctgt gacaccgaca ccgaccgact ggcagccgcg cgctggtgtt ttgatgtcga 900
acgcggcaag gccggtgcat ttgctcgcgt cgtcgtatcg tacgccccccg gcggggccat 960 acgcccatac ctgccgcgca ttaaaaatcc tccacgtacg tggtcggccg acgggccatg 1020
cgcctgccac tccacgccgc ggcacggcgt ggcactggca atgttagcac gacaagggcg 1080
ccactccgcg ctggcacacg cgacgtgctg gccgccggcc cgcggcgcgc tgccgcacgc 1140
ggcttcacgt tgcttggtct gccgctgctg gcgctcgctc gacgacaccg ggcgggcggg 1200
cgggcggcac ggcaggactc cggcacccct ctggctctac tatccgttcg gctttatcca 1260
cctgcgacgg ccctacgttc gtctacgtgc cgtggagagc acagggcgcc acggcgccgt 1320
gtttcttcgg tgcttgtctg gcccgtttgg caacggtggt tccttaaaat gcagatccgc 1380
tcgctgaaga gtgaagaccg accgactcgg ggatgcgtga gagagaaaat ggtgatgagg 1440
ccaagatcga gtcaatatac acgacaagat ggaaggtacg attggatccc gcccgtcgac 1500
actcaagcca gactacattg atagctagct gatgcctgac gtgtattttg gttgcagtga 1560
caggatgagg ccgatttagg attttgtttt agcgtaggta tgccatagta attaataatt 1620
tatccaccaa aatctggtat actctttgat atattataac tcggtgtagt ctatataatg 1680
tggtaagcaa ttttaaaaca ggtcaaaaca ggtaaaaatt atagatcaag tagcattcat 1740
ag 1742

<210> SEQ ID NO 51
<211> LENGTH: 1636
<212> TYPE: DNA
<213> ORGANISM: Zea mays

<400> SEQUENCE: 51
tgggaatgag ggctaaagct agctaataga agaaacaaaa aacgtgttat ccaaaggctt 60

```
cagtaacaag tctcgtgata tccaaagtaa tggatatcga tcgtgctctc gttgcacgat    120
tgtgcaattc caactctgac catgaatcag aattcagaaa gctcggaact gaaacccgac    180
ggacgaattc tcggtgtttt cgtataatcc gtgcaagaat ctgactggtt gagcagtgca    240
ggtcctgcac gatgtggtgc cctagcttcg cgtgccagaa aagcaggacc agcccgccgc    300
cccagtcacc gggcgggccc accctcgacc gcagccgcgc tttcaactgt tcaagtaccg    360
acccaaccgt cgccggtacg tcgtccgtcc aggctaccca gtagccctca tcggcgggcg    420
gcggccagca ccaccgccac ggcccccaga cccgaacgtc gccattcaat gcggcgcacc    480
tacaatttcg caacgaccgg ccgggtacgt acgcgacccc gcaggcccct gcagtggtgc    540
cgctctgcag ccctcgttgg ctgtctgccg gtcgccgtcg tcgggagcgc ttgggatggt    600
gggggggcca aaccggcggg gtagccgccc aggctaggtc gaccagagcc ggcccatgtg    660
gcccttcgct tggtcgggca gcaacgctac gctgtgtggc ctgtggctgc ctgtctgccg    720
tccccggctt gggttgcacc gagcagcaga gctgcagcag agacgtgacg tcgagcctgc    780
aatttgcgca tcaggacaca gccaccggct gggcacgtga acgcaacgca cagctcaacc    840
gagagggtcg tggcgatcac gtgactgctg cacccaaatt ggctgcggcg tgttgtgttt    900
aagcttccag ctggatctga aatcgatgtg aatgatttgc cgcgaactgt aatgaaccgt    960
atttaactct tgtgtagctc gcggggatga tgggttgcag cacaggtgtt gggccgaaat   1020
cctatggccc atcgctggtg aaacagggac tgctcactgg cttccacaca cacacacaca   1080
gaggaatgtt cggtgcgaat tgtgatcctg gacctggagg gagggagagg gggtgcaaat   1140
atcctgactc ctgagagcgt aataaatttt ggtcagatca acgacgttct tcagaaacag   1200
aggtgcatca tggcgaaaga aaaatgctgg cgcgacgttc atggcaggta gacacgacac   1260
acaaaggatt actctatctt gtgaaagatc tcttgtatac tgtcatcaca tttactgctg   1320
tagatagagc tatgtgtaat ggatgttcag acaggcgtga aggactctgc aacttccttt   1380
gtcattggct cgttgattct tctcaataat ggaattgaga tccctgggcc ctggggtggt   1440
aagacaacgt gataatggag tgcatgtatc ctagcctcct agtagggaga tcgagaccgg   1500
aataaagact attattcctc tgaatagctg tacagctata tacgtataat ctgcaaagct   1560
atatcttaat cttgttctga tggcctacat tgcgtcatta tctgctttgc tttggtcttc   1620
ccctcccctc aatgca                                                   1636

<210> SEQ ID NO 52
<211> LENGTH: 2937
<212> TYPE: DNA
<213> ORGANISM: Zea mays

<400> SEQUENCE: 52

cagagccgag cacatcgtag tagataaaag gaaggaacac gcggtccttt ttctagaagt     60
ttcggaaccc aattgcacga gtcagcagct catgttaatg ttagcttttt tttccaagcc    120
gaaccgagag cttgcaagcc gccagccaca ccaagtcgaa gtggagtttc agcccacttt    180
cgtcgggaac ggaggccgcg gcccaatgga tccgacaggg tgatctgagc tcctgtcggc    240
gggccgctgg gagcagagtt cctttgcgac aagcccacaa ggaactcagg tccggagtct    300
gaaacagtgg cccaacgaac cggattttcc gtagcgtaga caactgttcc acggaaacgt    360
aggcgtggac ctccgtgggc tggtggtagc cgacacgagg aatagtagga cacctgcgtg    420
actgaagagg aacagccacg gttggtggtg ttcgagtttg cgtcattctg aagcctgaac    480
```

-continued

```
agctagcatc ggctttgact gctctcgcaa cagcaagtca gcgacccagc ttattaccta    540
cgtctacatg ccaattgaca tgacttctca tggctaccct ttttatgact gcgccttaag    600
actagtaaaa ctcacgaaag ggggagactg tgaaacgatc cagttcggcc cgtccccgac    660
cgctcccgct cccgctcctg catgtggtgc caaaagggtc aatggagcta gctagatact    720
cgtgagaact gattatgtct cctaatcatt taatcaatca tgagattgtt tatgctcgtg    780
gttatgatta ggccaagaga cgaagacaag cggcgcacac tcaagtgatg ccccccagag    840
ccttcttgcc atgcactact actactacgg cgccaccgaa caggctgtcc ccgctttgca    900
cgtccaggaa atcaaaactc cggtatagaa gtagaaggac ggcagctgca gcgcatgtaa    960
tggccgacca gggcggcagt agaaaaaaaa aggtcgagga attcggttcc tttcctccag   1020
gcagcccttg ggctagcatc gttggcaact cgctatcctg ctctaggacc tcagtcagtg   1080
caaatcttcc actagccatt tgttaatggc gaccagcgct agtagctagc tagctatcta   1140
ctcgacacag tgagcgtcgc ccgagcgaga actcaacgcg ccgaggcacc aggggcccgg   1200
ggtcctgttc ctgtagccta gtccacacaa gctgcaggtg cgtgacacgc acaaaccacg   1260
ccacgcttaa ttaaccacgt cattccacga tctgttcgtt tggcgcaatg attgtctcag   1320
caacggaaca aacaagggtt cggctcatca tcaggggggg taatgcatgg aggcgaccac   1380
ctaacgagag gtcttaccct tgaccacacc ggccggccgg acgggggcct gatcctggct   1440
aaaacgtgct aacaacggtt ctcataccaa ctgttggtcg tgtggatgta cataaccaac   1500
tgttgcagca cacgtgcagc aaggatttct agacacgtct atatagtacg aaaggagaca   1560
cgtatggacg aagcagtttt atagaagaag aagaaaaaaa aacccaagcg attctgccat   1620
cataattgtg ccgctgcagt cgcgccttaa tagaatacgc taatggagac gaaaagcctg   1680
gttgttgtag gttgagatgt caggacgcgg ctatagaggg agctgaggag aactttagta   1740
cagttcggtt tcttggttcc taatgaacaa tgatatgcat gcatgcgtag ctaataaggg   1800
gggtgcccca gctgcccttg aattcaggct ggggggcggg ctccacggcg tctgcatacc   1860
acaaccgaca ggaacgggat aatattatta ttctctccac cggactcatt agcgtttatt   1920
aggaaccaaa cgtcccctca caagacaaca aaagtagtcg agtagatggc gcttatatta   1980
actttaagat aaccctacat acgttagggt ttttgttttt cttccttttt ttaacaaata   2040
aagtacacat tttatttgca ctggttagca ggaactgccc cctttcacac gctcttgatt   2100
tcaggacaat tttttgaggc attacgtacc gatgtaatat atcaacacga gatacatagt   2160
aataactaat ttttagtttt accattatac aaatataatc atcatattcg aacatgttat   2220
gccctcacct taagagctaa caaaaccctc ggtgttaatc ccaatagcca attgtaatcg   2280
gttgcaccgt cgggaacata aaaaccacat cggccgccaa tcataaaacc ttgccaacga   2340
attgtcgaga actcactaga accctaggca acaaaaaaaa atgcagttct agtagtatga   2400
acagattgta gataggccat cttcgtgctg gagcttcttt ccccccctgaa taattaagat   2460
ttatctcatg atatattcgc agcttaatac atgtatcatg tatgtacact gttgcttgtc   2520
gtctggtgga ctggtgggcc tatagactat agtataagca ggcactctgg catggcagcc   2580
aaaatcagag agacagtagt ctcacaacat agtcccgaat catttaatta tccaggggac   2640
ccaacaatct gcgagcagga gtgtcgtatt gccacaaaca aagtgctcgt ggcgtcgtat   2700
aaaagaaaaa taggggacaa aatttcatta ttcggaactt tctctcgcac actatggcag   2760
aataaagcga acactactac agatcctacg accactggat cagcaaccgg caaagggagt   2820
actactgtat gtcaaagtgc aagctccagt ctatatctag ttgttgcgag tagcaaattt   2880
```

tgcaaccgca ctcaagggac agagagcggg ccatatttct gaaacataaa tatgacg 2937

<210> SEQ ID NO 53
<211> LENGTH: 1941
<212> TYPE: DNA
<213> ORGANISM: Zea mays

<400> SEQUENCE: 53
gaaggaaaaa aaaacatgcc atgcaacatg catgcatgcg tgtatgtgtg tgtgttgcac 60
tgcacgcgct gcctgtgtgt aggcaccttt gccttcgctg gcaataaaaa agcatacgga 120
aacagtactg ttaactagta gatctggaga gatcgagtgg gtggactgga cgagctgtgg 180
catctgcatt tggcgtacct atactataca gatccaatcc acgggggaaa aaggtataga 240
tcaggagaga acgcactggg ctgggctcga aacgaagtgg ccaagaattg tccttatttg 300
cagcggcggt gaaaatgaaa tcctcttgga tcttttgatc gggagaaaag cgggcctgca 360
tctgcatgcg tgacgcaccc agccacgtga cagaggatgc ctgatccgac ggtcgtatct 420
gtccgcggca tctttgcgca aaaaaaaaaa aaaatcatgg agggcagata gcgccggtgt 480
gccagccagc cagccagcct tgggggaggg gggccgtcag gatcaggact caggatttgg 540
accacggcaa agggcctggg accctcgccc ttgttcaatc atttgcacga gcgaatgctg 600
cgctgcgccc tgcaggattc atccgactgg aggccgaggg tgcatgcacg tcagtcgcat 660
tgcacggcca tggacacgta caacgcaagc ttgtgactct gtgactggga gcggtgagca 720
tgtgagggtg ttagactgga ggaggactcg agtgacgacg aatcgttgca gactgctggc 780
ttagttgcca ctgtgtgtga ctgtggtaag tacagcagga catgtggcat tggcatgcat 840
ggcggtgaat taagaccagc gtagtaatca tgcatgcatg gccagttcat ctcgtctcgc 900
tcgcgttact gcagagtctc gctgtagtat atctgtactg tacccgggcc gggcggacgg 960
acacacagca gcacagcaga tccatcaatg ccgttgtact actacacaca cagctacgca 1020
ctcagtgcat gcatggagag actggagagt atagtagtac tctacataca cacacacgac 1080
acgagggtac atcaacagct catcgccttc atcaggtcag tcattcgccg agtcaccagc 1140
agcctggccg cccttttgct tctgcactgc cacaggagta gtactactgt actagctagc 1200
aaggccatcg atcgctagct gtacgcgctt gcgcctttct ttgtggctgg ctccgtcgct 1260 tttccccct tttccgagaa acgggtcggg cgggttcggg caggcggaca cgacggacat 1320
cctgtccacg agaagaattt ctggacgggg tttttttct ctctctctct ctctcccaaa 1380
ctcagcggca aaagtttctc aggtccacgg cgggcgccga ggcagacgct ttcagtgcgt 1440
tcagattcag atagatgaac gcccgcggta ccggcttcca gacaaacatg ccttttttt 1500 tttgaacgag tatgatgagg agaaaacaag gcggaattgt tccaggaaag acggatgcgt 1560
cttgactgcg tttcggtgaa atttgaaaaa ggtcgcgaaa aaaagtgatc cttcagggtg 1620
ggcccgccgg agcacggcag atggacggaa tccacacatg acgctgtgtt gtttgactac 1680
catgtactag tagtgtttag ttataatgca ctctccctga gccctgactt accacgtcac 1740
tttaaaaaat gctcagacat atataaacgc gatgcattta actttctact cctggttgac 1800
atggaaagac agacaaagat aatagtataa tactagcaca ccacatagat cagggtcaga 1860
gaggaataat tacgcgcgct cgcgcggtct gggcaacgtc tgcgtgcctc gagtttgatt 1920
tgaccaaaaa aaaaaaagaa a 1941

<210> SEQ ID NO 54

<211> LENGTH: 1560
<212> TYPE: DNA
<213> ORGANISM: Zea mays

<400> SEQUENCE: 54

```
tagtactact gtctactcct acgtacgtac gtacgaccgg gccgttttgc acgctctgga      60
actggtagtt cgctagctag tacgtgcgga gagccggaga cgaagcgacg gatccgttga     120
tcgagcgcgt cggtcccgat ggcgacagga gcgcactagt acgtgctagt cgcgcgcgtt     180
gtttcggcac atcttccatc gatcgcccgg ccggccgttg acgacacgcg cgcactgcac     240
atacgtacca cagcgtcgtc gcgcagccgt ccgttttctg caaccagcta tagctgccta     300
gctacctagc tagtctacca gcagacagac gccaacctga cccttgactt gcgcgttgtt     360
tgcgcgcgcg cggggccggg cacacgctct cgcgtacgta cccgtccact tcctcacgcg     420
agaataaacg gcttggcctt agcttggcgt ggcccggagg agtcgttatt attattgcca     480
catgcagctc tggagacgag acagcatctg ccgtgtgtct tcgcgcggaa ggaaagaatc     540
cagagcgtgg ccgcgccgcg caggcagtag gcgacgagac gtacggaggc cgcggccgaa     600
agcgagaggt cgggtcgggt cgtcgccgcg gaccgacgac gagctagcga ggttgccccc     660
gtgacgcgtc ggcaataacg cccgcgcgcg cgcgtatata tatatatatg cccagatcga     720
cacacggctc gtcgaaataa ttagccggca ggcgtttgtg ggcgcggtgc gcgcgtacgt     780
gcacacgcat gaggtcgagg gccgaccgat cgcccccggcg gcgactgacg acccatcgtc     840
gcgccgtgga cgattcgaat ttggggatcc ggacgccgcc atgggtcgat ctgcatgccg     900
gtcaaatgaa aaccgtgtgg atggagatgg gggatgggga tgggttgctc cgatccggcg     960
tcgctagcta gctactacct gtgctagcta gtggtggcgt ccacggcgcc acccacctcc    1020
actcaggcgt attcgttgct agtacaagta cgagaaccac ttgctacgac tcgtcgtcct    1080
gctaggtgct agctcgtcca tgcatgctag ctagacgcca ctgggtgcat gagtgggtgg    1140
cgtggcatgc aggaaatatg agctagctag agagcgaaat taggacgacg ggttaattag    1200
agagatagca gctgctatct atatagttag tagcctatta ttactagggc taggacgagc    1260
tgatgaggga ccgacaggga gagagattct ctttgtttgc tgctaacccc gtgctcctgc    1320
tcgtgaagga aaggacggcc gatcagggga gaaagagaga gagagagaga aagctgtatg    1380
tatgcggtgt aggattatta cagtttagct tctctctctt ggcaagtaga gtaaacaaac    1440
aaatcaatcc actagatggg acgactggac gagaaaggga gagagagagg aacaattcaa    1500
gggccgccgg agtgcgtgac tgactgatta tatatcggaa atggacgacc gaccggatgg    1560
```

<210> SEQ ID NO 55
<211> LENGTH: 2113
<212> TYPE: DNA
<213> ORGANISM: Zea mays

<400> SEQUENCE: 55

```
acggtcatgg gggcacgtga aagcgtacgc gtgcgcggcg ggcgcagcgt gcgcacgttg      60
gaccgagcgc ggaacggaag gcccgaaccc gaagcggcca aacccgccgc ggaaaacgta     120
cgagcgggga aggaggcgtg ggcgcccatg ctgctggggc cgccgttagc ctcgccggcg     180
cgcgatcgta ccgcgcggcg gcggcttttt tccatgggcg gtgccgcccc gccggcgggc     240
cctccgtccc tatagtcccg tcgcaagcgg ccgctggttt ggttggtcgc ttcgctcggc     300
aggaagcgag cactgttgac gggttggcgc ggcgcggggg gctcgctttt cttgccgtcg     360
actcgtggct ggctgcacca cctgactggc ggcgggccca ccgaggcggg gaagtgggag     420
```

```
gagacaggcc ggatccgcga ccgcgaccgg ggcggggagg gccccccacc ccacgtctgt    480
ctgctctggg aagtgaaacc aaaccagcag acgaggacga gacaagccag cagccagctc    540
ccgtgttgct gccgccggcc gctctctgcc cgcagcccgc agcccacaga caggaggggc    600
gtggggggcc cgggccggag agagccacct cgcgactcgc gccgtcgccg ctcgcaacga    660
ctttaactgc cacatttatg gccctgctat aaaacaaact gccgcattta ataggctacc    720
ggccaggcct gagagagatt cgggcagaat ggggaatgca gatgcatcag tggtgcagca    780
gtgctacagt accagcgtat tgcattgcat cgccggaacg cgagcaagat tccttcgtcg    840
tgaccgctcc aaaacgaccc ttgccttggc ttgcactgtc aggtggaagc attgttcact    900
gtcggataca tacatgagat catgtgtgcg acagactgta cagcaaacag ctagctcaca    960
tcacaaaaca tgtggccggg gcgcacacag actaataagc tctcgttaat ttagtgtacg   1020
ccgaccgcgc gcgtcggtct cactttgctg ctttgcatca gatcaggtag gtaggtaggt   1080
tatatatgtc attttgttaa gaaccatttg ctaattaaca acctgcgccg ttttggcgcc   1140
aaagttttca gacagagtta ggtcaaacca atcctctctt ctattttatt catcaacgcg   1200
tattaacaca accaaccacg tatagaacga ctcctaaaaa gaggctcttt cttctgcagt   1260
tgtttttttt ttctcataat gtatgagctt cgaaaagttc agcaattgct tgctgcactt   1320
ggattacaca tgttcattgg tcgagtacgt gtcgtttcag ctggatttga tgctgcgatg   1380
tagtaaccag ctatagtgca cgcgtgggcc ctttttatca cccccaaacc cacctttaag   1440
gaaatcgtaa aggagatacg tacatctcta tctagcttca acgaaaggtg cgtgccaaaa   1500
acaatggcag atgactagat tttgtgattg gatgatatgg aaagcaatta ttaatcatct   1560
tttgatatct cgcggtcgga ttcatttgat tgatagagag ccggcgttcc acttttcata   1620
tttttgcccc tactagcaga cagtggctct gtaacttcca atatggattt gtgggactga   1680
agggttaatt attatctgta ttctgtataa tcggtggctg tatgtacgat ataatcattt   1740
tgaaacataa cggtacatta tttctcattc ctgtccaaga agcttaagtc atgtatggat   1800
ctaactaaca acaggctaac taacttctta gtctatgatg atccaaatat acaaactaaa   1860
atatgagtcc gctagttaat aggactagta gttgttagtt tcatatatca atccagttgt   1920
tactctctgg taacatcaat ctaacaagag ttcagtccat gctgtttgtc tcacgcaaat   1980
atatgtgtta cgttgaacgc cattcgatag tggtatatta tcaacttatc ttgtggttaa   2040
tatgattagc aaaagaataa caccatttgt cactatattt tacttctata gtataagtag   2100
tttttaggaa tac                                                      2113
```

<210> SEQ ID NO 56
<211> LENGTH: 1580
<212> TYPE: DNA
<213> ORGANISM: Zea mays

<400> SEQUENCE: 56

```
gttccgtccg catctgcaca agtgatcgaa cggcacaccg cacacgcaac cggccggggc     60
cgtgaatagt ttcctgaaga cgattcccca acgacgacga cgacgacgcg cacagccacg    120
cggcacagtg ctcatcaagt acacagtagc acacacagcg tgcgtgcggc tgcaattaat    180
catatatacg ggttatttaa gggcaggcaa agcaaggcga ggcaagcagg aggccgacgg    240
cgaggtcacc cacccagcgg cggcgtacca gcacacgcta cgccagtcgg gcagtcgtgt    300
gttttttat gatagaattt tcttcgtaga catatagatg ctggtattga ttgagatgtg    360
```

```
gctagagtga tcggccggca tgcatgcgat gcgatgcgtt gcgacggagg ggagatcctt    420
ctcctgctat ctcgtctcgt ctctatacta gctccgcgcc aagaacgtcg tcacagaacg    480
tacttactac cagcaggggg ccgggcccgg gaggggctct ggccggtcga cagatcgttg    540
gcaaccaccg ccggccactc attgagcgag atgcatgggc tagtaggcta atcctatatt    600
tttttaaca cgcatgcata tgctgatcaa tgcgaacaga cggactgaac tcgacccatc    660
tggatgtagc agtagtggtg gctgctgttt ggctggcatg gcatggcatg cgtccggcag    720
gcacgcatga cagcatccat ccagtacctt attgtctaca tcgaatattt tgaaaatttt    780
aaattcgctg gttttcgtcg actggctata tatagcgcat ggaaatgaat ttaatttagc    840
tgcagatgga aggttgttag aggacgaagg agctcaaatc gagcttttgc atggaataat    900
ttatacgttc ccagcatata tatgcataca tagacataga gctgaaccgg cgcatgtcta    960
cctactacat acaaacgagg cagatgaggt tgctagtagc tcgacgatca tgcccttgtt   1020
cttctttatt ccccatttaa tagcaaatag agagagagag agattaaaaa aagggaaatt   1080
gttcagtcag gagtcaaatt ccttctctat ctagaggcaa tacacgcagt atatatacac   1140
atatctctgt caccggatta ttgaaacttt tgtttaagta gtatagtagt atatagcaag   1200
caagatttta aaattttggg tgccctcaac tatacataca aaattcacca ttcacatggc   1260
ctgcttgcca ctccttcggt ccttaagagc tgctgtgccc tgccctgcgc agactgcatg   1320
agcgcgcgca agaatgttca gaaggcaaca gaacaggtcg tgcagaaatt aaattaaaat   1380
agaagaatcc atgtgagcta agctaagcat gcagcagccg ctccgtcaaa tatgtcaatg   1440
catcaaggag agtagagctc ccaatcctgc tgcttgccac ccgtcgtgga cgcacacgca   1500
tggatccgtg ttgcatatgg ccagctcgat cggagcagcg gcaggcgtca tcatccgtga   1560
cagcaacggc gcaaccaccg                                                1580
```

<210> SEQ ID NO 57
<211> LENGTH: 1967
<212> TYPE: DNA
<213> ORGANISM: Zea mays

<400> SEQUENCE: 57

```
gctggtgcgc gtctcaaagg tgctcgagga cttccgcgcc tccaacgccg agggttcgca     60
ccattcgcct ccctttattt tggctcctgt ttttgaactt cggagcggca aatttggtgc    120
gttcgaacga gtgtagcagt agtgttgatg caccgctcag tggactttgc gcctggggct    180
agagtttgag cgtatccttt ccaattcttg ccgcatttgg tccttttgct tttctgttct    240
tttttttca actccattag aacagtgtat tttttgtcct gtgatcctgc cgtccttagt    300
cctgagtgca tttgtattac aacctgcgtc gtggtttgct ttgatgtttc tgttgtgtac    360
tgatcacaat agtgctgctg tttctcatcc acatcgtgct tttatcaaca tgtctgttca    420
catttgcagt tacatataac ttgcacatcg gctctctgat gctaatatcg tcacacaaag    480
tttgaacgtt ttcttaggtt tgacatgtgc taagtggtgc attcagtgtt tgtaatgtag    540
ctttccagtg atatattttg gaatctccca atcttaggtt atagaatgca atcgtctttc    600
cacaaactta taactgttta ccattgggtt gcatcttgca attttagaca tgattgttgt    660
tagatacctg tacgcctcct agatatatag taaaattgcc ttgcaaaagt ctttgcatgt    720
tttcatggct gtatattagt gggagtacca gcacattgag cacaagcaca gacccaatta    780
attgtttgat ataatttatt gatggtagaa ttctagttac gcgcataagg gtcagtgtag    840
cagtagatct tattttgatg gcattctttt tctcgtatat tggctggccc tacttcagtt    900
```

```
gaagcctcac ccatctatat tatgtagtaa tgcattgaga ttattgctct cttcctttgg    960

tgctgtgagc tgaataaact gatacttaga ctattttacc ttgcagtgta cacatttgaa   1020

cctgatatat ccaaacaaga gcgagctgca atccatgaga tgtgtaggaa aatgggcatg   1080

atatccaaaa gttctgggtg agtaagataa ctaggattca ttgagcaaaa ttgtttcatc   1140

gaagagttgt aaggaatcta tggttttgct tgcgccatcc taatgttatc tttacaaaag   1200

ttacttgtta aatgtctatt ctgagttcta tttgacttca ggaacgggga acgtcgacgc   1260

ctttctgttt ataaaagaaa acagaagcgg gggcctgaat tggaacaagg ccctagctac   1320

cttgggtttt ctgaagaggc taggcatgtt ttgcaggatt tatttatgca ttatcctcct   1380

ggtgatgctg atttaagtgg ggatgttgac cagaattcta gtgataaggc tgcaaacatc   1440

aaatggagaa cagatagtgc gttttgcagg cccacaatga gtaaacttga tataacgaag   1500

aaagttgaga tgctcgcctc aaaaataaat ggatccgaac agttgagaaa ggtctcacat   1560

tctggcttga taataatatc ttcctctctt tgcttagttg ctgctactta ttagttttat   1620

ttatgagaca atcttattga tagctaaagc ctaaaggttt acttttgaac aggtcatgga   1680

agatagaaca aaacttccta tttcatcctt caaggatgtc atcacttcaa ctttggaaaa   1740

tcaccaggta tagtttttag ctccaaaggt ttctcacatt tgctagacca catcttcaac   1800

tcacatggtg cactggtgct agtttttcct ctcagatgtg cagggaaact gttttttttt   1860

cattaaagaa gcatagcata atacaacaat ccccaatccc caaggcccca accaaaaaac   1920

agaaaggaaa aactgggttt ccatcgtgaa ttttagaaca tgcatac                 1967
```

<210> SEQ ID NO 58
<211> LENGTH: 1606
<212> TYPE: DNA
<213> ORGANISM: Zea mays

<400> SEQUENCE: 58

```
tcgcgttcta cgcgaaccac agtctaagcg agagagttta cccggtccat ttcgtttatc     60

cgttacaaat gttggctgac agctgtataa atccatcagc tttcacagtc acagtaagga    120

cgtttacatg gtcaagtact ggtcaagaat acgaacgcca gaacacgtat gaaagaacac    180

ccccaatcat atatatgtac atgccgccgg ctggcgggcc ttaataattc tgtaaaaagg    240

tttaacataa ttggccgtaa aaaattttca ctggcagata gctagggcgt ggcgatcgag    300

tgtggtgtgt gtgtcagctg gcaagttgcg agtgctcagc gtctactacg atccacgacg    360

catgtacgta tcccggtgga tctatcccat gcaatgccaa cgcactggtc gcgctagtac    420

gtgccacttt attatttatt ttgagaccgg cccggcccgg cccggtcatg catatgtgtg    480

gcgcttgtag aaggctgctt gcctgctctg cttgtcatca tcacacacgg ttgagacctg    540

tcgacttgag atcaatcaac taacaagcta gtgtagtgta gtgttgcgtt ttgattgaga    600

aaaacgaacc tgatgtattc actaaaacgg ccacacatta ttgtcgcttc gttgggcaat    660

catatcggat gtttacggtc gaggtacaat gcatggctat atgtgcacaa aaagaaaagc    720

tgatgaaccg gccagcagca tcgtcgtccg tatccatgca atttatcgta ctgccagaaa    780

cgtgaagaca cagcaggact tgcacattct ttgactgatt tgttttaagc cgatgcgtct    840

tcgtaagtag tatctcggtt agttgtcctt cagtggttgt caggcgccca accaacagga    900

tggcatgcgg gagatgcggc gtcacctggt tgcttcttcg cctcttcttt ttgcccaagt    960

ttcttggtca ctttagctca cttttggact actgcgaaat ttacccggcc ggttctgcgt   1020
```

atacaccaca gggtcgtgat actttttttta ctttcaggtc gcacttgcat cactgcatgg 1080
ttcctccgga agcagatagt cttaaagtta cgtttggtaa aggtgtggaa cgaccgaacg 1140
agtaaactga ttggtgcgcc gcttgtactt gtgatcttct gaaccagagt tcagtccacc 1200
taccacggta tgtgtggtgg gaatacccat tcgcaacaag gggacaggta acttgtttct 1260
gatttatagc attgccgtgt gaaaggttgg aaccaaagta tgtcgtgtgt accagtgtat 1320
gtggagaccg tgtcttaggt gaggacaaga aaattgtttt aaaagatttt ccatttgctc 1380
aagaataaaa tttcacatat ccctagtgtg atacagaaat aactgaataa ggtctaagtt 1440
ggtatgcaaa cttgttcccg caaatccgag actaaaaaaa catgtggtgc ccacatgtat 1500
cagtcttgta aaccaagagt tcaatatgcc taccacaata tgtatgaaag ctactcccta 1560
tagagattca cttgcctcag atttaccatc actacagcaa gagagc 1606

<210> SEQ ID NO 59
<211> LENGTH: 2765
<212> TYPE: DNA
<213> ORGANISM: Zea mays

<400> SEQUENCE: 59
tgcatacaat tacgctaaat ggtgcttcgc tgagaatatt gtagtacctg cagtttgtca 60
gtagtcccct tggagtacat aaaggaaacc ctccagtcat atgcatgtaa gacctttggc 120
tcatcctcaa tactaagttt taagtacaaa tcttgtccgg ccctgtttgt gaatgttata 180
tacgggcgta catggataac ctgttgttgc ataacatgaa gtcaactgat tgacacttta 240
atatgaagtt gtagattaac atgcagctac ctttgttgga acagcttgat acgaggatgg 300
ctttgaacaa agaagaatat gcatgcattt tccatcatca tcataggcag aaagatcaac 360
tgctccatcc tgaatatgga atcagtacta tttaattgta gtggtagaaa acaagaaaaa 420
gaagaaaaga agatccaaac taaccatatc gccaagaggc gacaattctt tcacagatcc 480
aaaccgtcca ccatgtccaa cagatgatag aagtcctaat cccttaaaat ttaatccaga 540
cgctatagtg tatccctcaa ccaattcatc gtgttttata tcatagagtt gcttctcacc 600
cctttccaga tgtgaacgtg aaagaaggcg cctcttctct ttccttccag aaatatcaat 660
gagacgcaga gtaagtggag gcaatctaga aaaagatatc caatagggaa catatattct 720
gataagcctt gccatcaaat agtcactatc actgctttgt tcaagcagaa tctgtacaac 780
cctacagaag aatgaaagac aaacaggata aaagatgatt agtgaaaggt tatggcattt 840
tatccaccat aattttttca tgtttgtgtt gttaccttcc tgataaagag cttcttagat 900
tgataaattt ggaaggtgct tgggttggat gtgatataac aacaggctcc taggaccaga 960
aaatcatttc aatagtatgt agaaaaaaaa tagaaaagca aggcatctat aaaaggaagt 1020
aattttatcc atacatgcat cagttcccat cctccatgtg gaaccaggga taagtacaaa 1080
gggtttcttg gatcaacatt gtgaaccttt acagcctcac ccggacttaa ggtgccaagg 1140
gagcaacttg aatcttcatt atcgaggtgg ctagaactga cagtataatg tgcagcaatg 1200
ggaagatagt atgtcaaaca caacggggac ttaataatga tgcaccaatc atatattggt 1260
tccatctgta catctttgcc tatttccttg ccttctatgc tcaagcaaaa ccacagtcca 1320
tgacaagaat tcgaggtgcc atctacctgt gagcagaata gcaagttttc cgattcatac 1380
agatctgata cacataaatc taggatctcc tcctttctaa actcggtttg actgcgcctc 1440
tcctggacat cactccagga gtaattttca tgatcatgat gttttgccgg ccttaactgc 1500
aacatatagg gcataagagg atgtgagagg cctgatagtg ggactggaat agtagaattg 1560

```
ggctccagcg ttccaatcag gatttgatcc tctttaccaa aactgtctcc ctgttcatct   1620

gcccgtgcac tttgagaaat tcttcctttt agacgtaaat caacaatgaa attggttgta   1680

ttagtaactg acacaaggga acgtatgcta acgtatctgt tgccttcctt gactgttgct   1740

tcactagcaa tcacacaatt accaaacctc caacatgctg caggtacagc atagttcaac   1800

ttcatgcttg tccatggccc ttcttttgaa gggctaatct gaatatatcc agtcttgctt   1860

tcaggactgg ctctgttccc ttgttgtaca ctagctctac cagaaacaag taccgcaaat   1920

cttatttttc cactaggttt aacagtttcc tgttcctgca aagaattgtc aatataattt   1980

tataaaatat tgtaagtata tttcgcagaa gcacactttg tgtggactct attttgcaaa   2040

agtgactcaa tacatgattc tccaaatgtc agagttctca ccactgtctt agttgacata   2100

aggtctccta aagccaaatc aaatttgaca gagtccggat tagaggtagg agggagcttt   2160

tgcacaactt gctccaatgg agcagagtat ataccaactg gttgacctgt tctcaacata   2220

aactataaac tagagttggg aaaaaacaaa aaaaaaggca tttgttgtga actaaaatca   2280

cgaaccttta ccagcatcaa gcacaagaag ctctagagta tagctgtcct gaaacattgc   2340

agtgaaaatg aaatgttact taaatgaaag catgcctctt ggaaaattca ccattaataa   2400

cagtagagaa caatttccat ggatatctaa accaaagaga gtaaaagtgt tccagaatgt   2460

tttgcgttta cataccacac gttcgacttt gaaaaagaac atttcgttcc agttcacctt   2520

tctggtgttc tgtgacaagt gttctccaat agcagcacaa gtacgggcac tctgttgttg   2580

aacagatatg gaatggtttt ctgaaaagag ccgcacagca gtcatatatt caccagtttc   2640

taatccttca tcatccttga cctgggatgg gaacctaagt ttagaacagc caaaaaagtc   2700

cttcgcaaca acttacttag caggcaagtt aactgcaata caaggttcag aattcggtgt   2760

aaaac                                                               2765
```

```
<210> SEQ ID NO 60
<211> LENGTH: 1725
<212> TYPE: DNA
<213> ORGANISM: Zea mays

<400> SEQUENCE: 60

ccttttactt tcctccagac taagcgatcg gaacctgctt attatgccgc acaatctgct     60

atttttcact tctgattact tgtagtggtt caatgaaaaa agaagagtac ttatagtggt    120

tgcatgtacg tgatgaccga ggtacacaag tgttctacgt gaagtgttat agatcaagca    180

cttgtgctga ttggaattgt tattttgttt gaactggcca ccatgtcatg tagttctatg    240

attacattga tggaaaataa atgcctttac ccttttctga aaaataaaat taggtatcca    300

tttaagaagg aacgggcttg tgtatttcca gttgcttgtt gccttgttga cttaaggagg    360

tcaagccatg cataacttta atgctgcccc tttacattat tttttgggta ggttgtggtt    420

gaattggtga tatgtgtggt gtggtgtagc gaaaggtgct gcaggagagg tctgattatt    480

gtttttgaac ttaccccctt gttagggatg caacagttga agatttctaa ttgccaaata    540

ttcattattg ttttgagaaa acttctaatt tggtaatctt tccttgatct attattattg    600

ttttaaaaaa tataataatt ttgttgtaaa cgaacatata gtaggcacaa gaagctagtg    660

attctctttg tttacttgat catatagttt tcaagattat gttggtacac aagttcaaaa    720

attcacattg gccgcgcata gcataattga tcatctacga gtggcaatgt ggcataattg    780

aagaaggcta actggctaag acaggcaaat cgacttgttt cactaataac caataatgga    840
```

```
aacttagaca cactagaacc caccatttag aaatctagta ttcatttatt gtcatctaaa    900

taaccttcta ttgaaagcca tctcccttag agtttccaaa gctttgccca ttggatttgc    960

cctagatttc caatttagtt ttggttacgt tactaggaga aggagaatag gagatgtcgc   1020

ttgcagagaa agggggttgc ggttatgtgt gagaagctca acaatctaga tcagttgtgg   1080

tcttgtgaaa gtaggaggtt gtgatcgcca agatcaacat catgcacatg aagatctatt   1140

gttgtaaacg agtttcgaac cctaaaccta accttccata cttcatactt gcattccgtt   1200

ttgccaaaca actagaactc gaccagaatt ttagtacaat agaaagttgc caatttggtt   1260

tcttttccta taggtttgtt tagatacttg ctttatgacc tttttcccac caaaagattg   1320

cctaagcatt gtgttatttt tgaaggaaat aattggaacg acttaagccc ttaggctatt   1380

ggctgtgctt attatatatt ttgtttatgg ctacggggtg gaggaccagg attccttagg   1440

tggtggtcgt ggactcgtgg tccgtttcag gccgaggttt gacacccctt caccctgtag   1500

tggaagagaa ggattaggca gaagggagag gtaggagaag actattgcac ttcttgatcc   1560

cactaagtac attggcttcg tttacaagga catatgccaa tacaagcaag ggctagttt   1620

ccctctatta gaccctatac cttcctagcc tctattgcta atcatctagc tacttgcctt   1680

tcgtgcctct acactgatat gcctttccca cataacatat tgggc                   1725
```

<210> SEQ ID NO 61
<211> LENGTH: 1584
<212> TYPE: DNA
<213> ORGANISM: Zea mays

<400> SEQUENCE: 61

```
gctctagtaa aattgtattt cctctggctg gcgagcggag gacgacggag cagaagcagc     60

tggcctcagc cgctggacag tgggcctcga ctagcagcag ataggaaacc gggatagagc    120

tgccttcccc ttccggctcc gctcagtcag gcctcagatc ggtcgaatcc agcacccccct   180

ccagatttgc gtcaccaatc ttcttcttct tccgccgccg ccgccgctcc cccacaagga    240

ggttagctgc tatccccaaa tcgattcatc aatcatccgt gtccttccat ttcattccag    300

tcggtcgccg cagcacggac cgagaacaga gcatcacgtc acatcaaact aacctaacca    360

gcctcgtccc tcgctgcgta tctgctgcac tttcatcaac accagtcttt ctcctcctgg    420

attgcattgc ccaggcaaga gaacgcacgc acaccgaccg gaatagccat gatcttctga    480

tccaatccaa gatgggcctc aaggagcagc agctagacgc cactgaccaa actcgtgatg    540

ccgccaactc cctcgcttct gtttctgacg agcaccacga gggaccccgt gtctcaagct    600

gcagcaccga caaggattct ggccttccaa gttgccgagt ctgccattgc gtggaacccg    660

atctaagagg cgagtccgcc ctcggattct tgggcatcgt gccccccttcc cctcccagga   720

ctgacactgg ggggccaaag gatgatgctg ccaccagccc caagggggag atattcgtgt    780

gcgctactga cgtcgaattg cagcagcagc aggaccatct tgtggatcta gggtgttgtt    840

gcaagaacga gcttgccctt gcgcactatg cctgtgcgtt gaagtggttc atcagccatg    900

gatccaccgc ctgcgagatc tgtggaactg ttgctgcaaa tgtaaggcct gacgatttca    960

acaaggttct cgcgtccctc aaggattacc aagctctcag ggaaagtaca tccacatact   1020

ggtggttgca gcagcatagt ggtgttgatc cagacgctgt tgcagcaata cgaaggcacg   1080

agatctcatc ctggttcaat cctcacgtgc ctatctccca aggccacatt gatcaaccgc   1140

atccctcaac caataattct tctgttcttg agcagcatac tagtgttgtg gcaaacacaa   1200

gatggagttt ggagagtact ggagtttttta ttgctatctg cctggttgtc attattcttg  1260
```

```
catggttggt cgctccacat gttggcaagg tatgctgcaa cttctgctaa agagtagtta   1320

gtactacgta cttgtccttt acaaatcata aagcggagaa gcattttctg tgcagaaagc   1380

tgctgtaatc tgtcttcata tgcttcttgg aggtctatgc atattgactg tagtaatatc   1440

cctgagattt gtaagtaggc ggtgacatat ttcatttttc cttttagcca gatttttcac   1500

ctctgactga gtttaaatgt caaaaaaata aataaatatg caggttttcc cgagaatcca   1560

gtatgggtct atgcaatatt gggc                                          1584
```

```
<210> SEQ ID NO 62
<211> LENGTH: 2420
<212> TYPE: DNA
<213> ORGANISM: Zea mays

<400> SEQUENCE: 62

cggttgtact tgtaaatcta gctgcttgta cgatagttat atgatgtgtt tttttatcca     60

tagcgaccac cacgacaatc tagacctagc tagtgcgact gatttttaca tcaatacatc    120

gcaaaagcta cgcacttaga gagaaaaata aacattggaa tttagagggt acagtattta    180

gcacttcgtt acagatgtgt gaaaatccgg agccgatttt gcaatagccg tggatcgctg    240

aaatcagacc ttccttgtgc tgtctaaaat aaataaatgt tttgtgttct tcgtcggaac    300

aagaacaagc accggttgct cggaccgtgg agaaaactgg ttgggctgtg ccgagaaaca    360

atgagcgggc tgggctgcgt cttgacggcg ggccaccaaa ctgtcccgcc gtgcgcgcag    420

ggcaacaacc acaacgtcat gtgcggcttg cttaactggg cccgttagac gcgggcttcg    480

tgtggccttg gaacacggcc gttcgacctg gcttcacgtg acgtgaacca gagcggagcg    540

gggccatcga tttcggccgc gcgaaacgcg tgcgcgaggc ctgcgaaagg ccgctggatg    600

aagctccctt tgattgaagc ccgtgtgggc cgcaccgcat ggtccggccg gcgatcgtga    660

ccgttggagt acgatttatt cgatgcgtat gtactcagct cgatccatat acgatatgat    720

agtacgtaga catcttagac gtaagttgtt taaggaactc tctctctctc tctctctctc    780

tctcgggttt ctgtgttcat ctcaaagttt tttcagttca aaaaccaatt cgaaaacaaa    840

tcggcttaaa attcaggtaa tcaggtcaag cgactttact ctggtctgaa taacttgaga    900

catccgggtt gccatggccg actctagaca gcggccataa acacggtggt ttctttttct    960

tattgggata gtaggtcact ccaaataaag gctattgcca tatgctaagg agacggaatt   1020

tgtgacgcca tcgccaccgg gttaacgtta atattctact actagagaat ctagcttacg   1080

tttcggttcc ggccggccag tagaaaactc tctctgaacc gaccggtcag aatcccctgc   1140

tcggtgctcg gttgcttgga ccgcacgcac gcacccctat atcgtcagtg cctgtaacag   1200

ttcttattcg gtgattatta ttataatatt attccacgtt tgcacacacc gcacatccgc   1260

ccgtttgtaa aactgtgagt tgatcgtcga gacgaaaggt ggagctggag tatatggctg   1320

ggcttcgatt gccgctcgca ggtcggtgtc ggtcccgaac ttttttactc gcgctccatc   1380

accacatagc ctggcgatcc tatcgtctgc ctacggggcc gcagcggcgc tcctccatct   1440

cctgggtctc gttgtagcca catatagagt agtagattgt tcgtcctcgc aatgatccgt   1500

agtgcacaat gcccagtcga atagtcgatg aatagcacat acacatatat gcgtgtgtgt   1560

ggtcttgtca aggttaactg ctgcagagat gagatgccaa agaaaaaaca catattctaa   1620

ttaataaagc tttgtgtgcc gcgacaagct agctaggcta ctgtctcgta cgttcacgcg   1680

gtctaaatca cgggcgcagc acaaattcga tggcagcctg gactaaacga ggccgtggcc   1740
```

```
gtcgtcacca ttcaccgatc cacaggattc acccgggggc aaaaccagcg cacattacct   1800
ttgcaggaca ggagttagag gcgccttttt cctggtccct ctctctgctg agcacatgca   1860
gcagctagct agctcacgct actagtcact cgcgaagaac gaatccccgg ccggcgccac   1920
tagttgtggc tagctctcgc gtctttacat tcgcagctgc agcgtccatt tcacaggcag   1980
tatacatgca tgtgatcgag tggaaggagg agaggccacc gctggccgct gcccgctgct   2040
tttcacgtac aggcgccggc agtgcaattt ggcgacgatg cgaggtgttc gccagtatgt   2100
ctcgctgaaa gggtgaagcc ggagaaaggg ggaagaatgt ttgctgcggc ggatggagat   2160
aagatcgcat ctcgatggga attagaacgg ccgccggccg agtgtgtgtg tgtggactgt   2220
ggatcgaaca ttccgccgcg cgcctgaaag gactgtcgaa gcattgtgac atctgtcagt   2280
cgatcgatcg tgtggttaac ttaacggatg ctaaccctag cttctttttt ctcttcagtc   2340
tagctagctt tctatcttgg gagacaggga cagcattttt ctttttgttt ttttagtggt   2400
acctttaatt ttgctggtgt                                               2420
```

<210> SEQ ID NO 63
<211> LENGTH: 2011
<212> TYPE: DNA
<213> ORGANISM: Zea mays

<400> SEQUENCE: 63

```
gcggctagtg gatggatcac acatgtttcg aactatcttc ttttccctgt atgaggtaca     60
gtagtagctt acggacgaag ggatagatat atacatacca tgctatgcgc gtctcacttg    120
tgtacctaca gctacagatg tgcatctcta tcctatctct tcactctggc caccttttct    180
tctagctcgg aaggaaaaaa aaaagcatgt attattgcat cacttttttt tttgcaaggg    240
atacggtgca gcagtactac tactgccacg cgaatgttca ttcacgccgc gtacgatagg    300
caccgctgca tgtacccacc ggcacagtac taacggttta gatgtctact acttattaat    360
tcaatcacgc gtctgcgaga aagcaagccg acgggcatct tctgcccgag tctctccgcg    420
tttctgtaac tagaattgtc atagtcaggg ttgccaaaca tcagcatccc gaggcagttt    480
ctttaattct gctttttttt atatatgtaa gtttgcttac cgaatgagct agttctaaac    540
aaactcaaaa acaaaacagg gcaactgggg gtcccttgac attgcacaga tggacctgac    600
cactttgaga ttcccccggc ttctatctcc ttttccctcc ccttggatca aatgaacaaa    660
ggagcgcatt ctctctctct ctctctctct ctctctctct ctctctaaaa gattaaaaaa    720
aagcctgcat gtagtgttct ttgacaagga caaggaagcc cttttacatc aatacatcat    780
tcgtatgttg ttgttttctg tgttctttgc gttccttttt ttttccctcc ctccgcctta    840
ttttttctac ttgattgttg ccaagatctg gagcacctga tctgatcgtg tgcgctggtt    900
tactgaacct tgggagggct atacgcttcg tacgggacat accaatttca gagaattcag    960
ttatcaggta ggtggttcaa tcattcctcc ttgtggattt gtgggaagtc agagctcgca   1020
agcatcgcca aaacttagag aaaaaataga cctgaacctg agaggatgat gatccgggac   1080
gcagctttcg tatcatattc gccgctggtt tcctcactgc aaggtgtgta aagtgtaatc   1140
ctcaaagttt agacgaagca gtaccaatca taggctcaca acgacactgt aaactgtact   1200
gcacagcaga gcagctggat gatgaactaa cagcttctcg ttttttttac gcatcatatt   1260
ttttgtatcc actggtcttt atcactcacc ttctcatttt tttatgcatc atattttttg   1320
ttcccttctc cttaattccc atgcggtgaa ggagagatgc gaactaacag tttggcgctg   1380
cactgttcga ccggctaaac acggggccaa tgctctctgt acgtgcagat ggataggata   1440
```

```
gtctttgatt cttgtttcaa gatgacgtgg atagtctata atagctaaat gtttgcctcg   1500

actactaact tgccgatatg ggcgagggta actttaaatt aaatttttaa agcatttgac   1560

ttgttaaaaa aaaataaaag cctatattct ttgttgatgg agggagcaag tggctgaaaa   1620

gccgttgcca tttctgggcg ctccctaaac tacgcggcaa gcaggctatt gggagccctt   1680

gtcgctgtcg acgcgatgtg cggcctcttt cttcgtcctc ttggttaggt cttatctaca   1740

tggtcacgca tccagtttat tcattaggta cgctatctgt gtgatcgtat gttcagttta   1800

atttatatgt gttagagtat aaaaaaattt atgtaaattt tacattagct tgagtcagtc   1860

agtcagagca aattaattta gcggctagac cgctagaggc tagtcgcgtg cgtgcgtcgc   1920

tgatactcac cgtcagtccg tcaccgacac ttggcctggg cggcgtgtag cagcagcacg   1980

gatacgggca atacggccgg gtgcatggtc t                                  2011
```

```
<210> SEQ ID NO 64
<211> LENGTH: 1766
<212> TYPE: DNA
<213> ORGANISM: Zea mays

<400> SEQUENCE: 64

gctggacttc agcgccatag gtattttcgt caagctcgtt gccaaggttt atgacattga     60

ggtcagcgcc ataggtcatg gtgttaccat atcgttacgt cacttctacg ctaacatctt    120

gtcgatggtg tcaaactatg taacctcgac gctatagaac atgaaataga cctagagtct    180

cgaatcgatt gtagttttgt ctcaagtcta aacatgtgtt gttgccctct tgttttgtat    240

tttgttcttt tttttgttac gagagaagag atttaaaaaa aacacaagaa ttgacgtatc    300

tgtaacgagc agagtacaca cgtgggctag ctctccgctg aaaagaatac gatttacata    360

cgtgtaaaga ttgtgcccac tcggcagaaa tttggtgatg cgggtccagg tcgttagcct    420

cggatgcagc ctgcaggcag cctgtggtgt ggtgtggtgt ggtccaaaaa gggcgggaac    480

agaaacgagg ggctggacgc ctggacccat ggatcaggtg gactggtggt ccgtgtgggc    540

gcaagcacca gtacagtaca gtacttaccc ccgctcctgc atgcatcgtc ctctgtaaac    600

acaaagcaca aggctttacc cgaaagcaca agctcaccta attaagctca tgtacgcttc    660

tggcgcgcac aatagacacg cccgtacgca ggagcacatg gcaccaaccg aatgatttga    720

gcaaccgtct ccgcatctgg aatccattcc actcacccaa acagagctcc agctccccct    780

ctatccagcg agctggacgg acgggacgga gcgtagacta gcagaacaga agccaggcag    840

gtcgtccggt cggggtcctt tccctctttc tctccgtttt ctccgctggg gaaaaagaaa    900

atcggaaaat gacgctccac ggaagaagcg cgcgagccga tggcaatgct tcccgtcagc    960

gtcgagcggc gagggtcccc gagacttttt ccccccctcct cccctgcgtg ccgcacacgg   1020

ccagaacggt ccttgctgtt gcggctttct atcttggaac agcgccggcc ggttgaatcc   1080

gccgtggagt cgagagccgt agtgattcct agtgcaagtt gcagagcgga gcaaagcaag   1140

ggaccttgcc gcaaaaaccg tggcgggtgt cgtctaactt tgtccgtcaa gggtcgccgt   1200

cggccttgac aaaacggaca gctgctgacc gtgacgagtt agaagagaga gagagaggga   1260

gatagaagaa aaatcaccca cctccggacc tccccacacg aaacgaaaag ctacgaccta   1320

cctctcttcc agacgtaacg taagcatgaa acagaaagca ctgcctgccg gaaaaacaaa   1380

aacaaaaaca aaaaaaaccc gaaagactaa taaataattc accgctcctc tttcgcattt   1440

ctccggatct tgtatgcatg atgtgtgtgt gtgtgcctgt ggataattgg acgcactcca   1500
```

```
ccctacagtc tcctctctca gcttcgttcc tgcgcccccg tatcgtatcc taatgcatgc   1560

tcacggctgg gtcccgtggg ccaccaggtt tttaatgtgc ccttctgtag ccacacgcgg   1620

agaggaaaag gaacccgcaa gaaacgggag tggaatagaa ggcgtctatt tttgcacgat   1680

ggtataggaa gcctgctggc gggctcggcg gtgcctcaga gtcggcgcgt acaaaatgaa   1740

gatgcgaagc tgttggagtt gaccta                                          1766
```

<210> SEQ ID NO 65
<211> LENGTH: 1600
<212> TYPE: DNA
<213> ORGANISM: Zea mays

<400> SEQUENCE: 65

```
ttcgtaataa taatgcaata ctgatggaga cgtcgacgac tggacacaga ttcatatata     60

ataatgcaat actaatgggg cgccctcagt ttcagtcttt gcgctggaaa tggccgatca    120

ttaaaaaaat ttcttttgtc gaaattcata gacttgcgaa acgatcttga aatatactta    180

cttcaccatg ttcctgcacc caaaaaaaaa agttctccca ttcccatcct cttccaggaa    240

caaaagcaca gctaccctac ccaggtgagg gctgagggat gtgtagtagt actgtccatc    300

cctgcatggc tgcatggcgg aatgggcgcc ggagtcggcg gcgcttcgag aatcatgcgt    360

ggcaggcagc gagaactcca atgcaaggca gcttgctgcc atcgattgcc atgactgaaa    420

cacgcatgca tgcatgcatg cagagttcta gtgtctgcaa tggacaatga tgaatcctcc    480

tctcccctgc attgcaattg caaagcagca tgcaatgcaa tgctctagat cttccggcga    540

ctgggcgccg gcgaccacgc ccgcccgccc accaccaacc atacgcatga attttaagct    600

gcccctcatc aaccagtcat gagtcatcat tgccatgcac cccccccccc cccccccccc    660

ccccccggcc gcgtcgtccg ccgtgcctgc catgccatcg ccggaccaga cacaatgatt    720

cgcccatgat catcgccgga ccggctagtc gatgtggatc gaagcaacgt acgcactgta    780

cgctgtgctg cagtggcacc accactgtat gtatccactg caccgcttgt tgcgcccaca    840

ccaagcactt ggtagtttgc atgccccgca gagggtgcag gccggccatg cctgcaggct    900

ggctgcagcc ggctgcatgc atcggccaag cttggctgca gagctagcga tgcatactgg    960

gctactggcg tcgcaggcgg cggtgatgcg tagtgcggca gtggtcgcgg tcgcggtcgc   1020

agccggccag cgggaagcgc cactggggtt ttggagagac gtgcatggcg ctttctccgg   1080

gcgctagcta gcttagctcg agattgactg gcaggctgca tgggcaggca gtgcgcctgc   1140

ccgcgcctga cgacggctgt gcctcggcta gcttgctgcc agtgccagtg ccaggcaagc   1200

tgacgcccgg tttcctccac caccggccac cgccatccag gatcaggttc agaagacgag   1260

aggaaagtgt gcatgatgga gaaatatact gtgagcttca gtttgcccga tgtcacagca   1320

gcgcgcgcgg tgggcgaggg aacaggagga catgtgctca gctccatgac ccggccctcc   1380

aactgtttac ggtcttcgtg gccctctaac ggttacagtg tgaggatagc gtgcgctccg   1440

tcaggccaag tcaaccggat gagtggacgc agcaaaacag tgttgcatgt cacacatgaa   1500

tagaaatttt ttttcccctt cgcggacccc tttttattca ccggtggtgc cagtaactct   1560

ttcctcccta cgcttacgta tcaatgtgca gatagctaga                          1600
```

<210> SEQ ID NO 66
<211> LENGTH: 2367
<212> TYPE: DNA
<213> ORGANISM: Zea mays

<400> SEQUENCE: 66

```
tatggataaa taaatccgga catagtaagt gtcacatatg ttatgctaga taggacaggg     60
tagccgcaaa tactttatga acaacggtgt tacggagtca gaatagtata tcaatgtata    120
ttcattttcc tcttatgatg actacttcac ggacttgtat tgtattatta aaaatcaaat    180
taggggataa aaaattgtga ttatatcaat caaaactaaa ggcaatatta gaaacataca    240
aaaatacatg atacatgaca cttcttagtt cttacatcct catgtcataa taccaaaact    300
aagggtcata atatatccat aattgttctt gattagcaaa aaaatcataa ttgttattag    360
aataatcatg ttggtacaaa ggcttgatta tgtcctataa atgaattata gcccaaaagt    420
taaaagaaac tcaaaacaaa acataaaaga tattaacaaa ctacaagtaa atagttgata    480
aactatatta aattgttggc atagtgtcac tgctgcatgt gcaaacatct gctgctgctg    540
tatccgccgg gttcttacgc atgtatgaga cagtgatttc atgagaaaga ttattgacac    600
gaaatcagaa tccagaaaac aataacttaa acagcacaaa gggagcagca gtgtccttgt    660
tggatacctt cgtcgggaag gtgatagatc acataagaat cactaatcta aaaaacaaaa    720
cagtaagttt aagagcaaaa cagcactagt accttggcta gactgtacat tgtacttgaa    780
tactctgggt gaccaacccc cagaacacgt ccttctatct acagatggca attaaaaaaa    840
gataaattgc atacttcaac aagtgaatta caagcacatt tacatttcca ttgttttgct    900
accatgcttt gatgctttca ttgaatgggt acaggtgtta agcagcagag tgacagaaga    960
tgacaacata tattcgtata gttctgaaag gttatatttt aacctatttg tatgcgatca   1020
accaaaaatg gacaattata agtatggtca agtaagatga tagtatagca taactcaaat   1080
attgttattg tggaatatca cattggtatc aattatgaca gaggcacaaa atttcaagaa   1140
taaatgttaa acataaataa gcaagagcac aaaaagttga ggtgtggtac cttcaaagca   1200
cgctgcaaaa ggggggaaac aacaaacaga aaagggtata agaagcaagt tcaaatcttc   1260
gaatgaaaaa aattaagttc aagacttgga atgaaaaaat taagtgcaga aagtatagca   1320
gcagttgaca caaagggtat aatgctacaa tggaaacagt tcaattagcc tttcacaact   1380
tcatgagaaa aatacatcaa ggatctcccc tactgtgact tcgttactaa atttcattct   1440
gtgtatcatg ataatgatgc atatagtgag gactagcatg cctcaaacaa aaagctgcct   1500
acaaaaatgt ccattcgctc acttgcagct tgaacagagt attagcatgc aaaattttgc   1560
acagatttac aaatttctta gattatgatt cccatcaaag gtaacagata ttgtcattcc   1620
tacaaactat tgcatgcggt ctgttttcaa actgtttaat gatattcacc aaaaaagaca   1680
aaaacaaact tttcaaactg tgttgcatag caaaattaca gaagaaacta taaaatctaa   1740
acaaagaaga ataactcatg aggcaacaaa acgttacctc ataacatgtc tgggcttgag   1800
caagcttgag ttgaagatga tagcatattc caagactatg cacagttctt ccaaccctac   1860
attaaaaaat atataatttg atgaattgcc aaatttagga taccatgcat ttggtgtttc   1920
aacagttcaa cacataggat caagcataga aacacattga gatagatagg aaattcattt   1980
agaatgttca tgtaggtgta gcaacgactt acatctgcag ctttatccct gaaacttagc   2040
atttggaatg tgatggctat cgtgctaaaa tgttataagt ttgtcaaacc tataacttct   2100
atggcactgt gctccagttc acttgtgtgt gcgacgggcc tacaactgta atagcactat   2160
gctacaacac atttttgtaa atatgtactg aacctaatct atgactatca aatggtaccc   2220
ctttattggt agggtacatg tcataaaatg tccctggggc aagctgccat gtcccttcag   2280
aaaaagggga gagctagaaa agcatcaagc agaatcagag caaattatcg aacacgacat   2340
```

tcagggttca tcttccgatt ggaaacc 2367

<210> SEQ ID NO 67
<211> LENGTH: 2071
<212> TYPE: DNA
<213> ORGANISM: Zea mays

<400> SEQUENCE: 67
gtctatacat gtcctagttc ttggctccat gcatgccctt atagttcctg gctcatcata 60
tactactgat cgatggactc ctggatcgct gaagctgctg cgtgtacgta gttccgtgca 120
gcacgcatgt tacgattacg actttgttag caggtcgttg ttatgcgccg tacgccgcgt 180
ctaagcatat atagtcagcg tcgtcgtccc ccctggcaaa ttatttggtc gttcttctct 240
gacgatgacg aaacacgttc aaaatgcatg cgcgtgttcc gtcgcgcgcg cgttcggtaa 300
acgcgcacgg gaacgacgta cgcgagctcg tgtcccctcg atcattggat ggtctcgtac 360
gtaagtttac tacccgacgt tgcaccgcga aattcaaatg ccagtgccga actaagtttg 420
gctgtcatac atcgtcagaa ggaaaacaga acccccaaaa aaaaacataa tgaggtattc 480
ccatcagagg taagcagctt aggcggctga gttgaatttg actgaataat atccatgctt 540
gtgtgtgcgt gcctaacgca ttgtcgtcgt gttctacgta cgctgctgca tgctactact 600
ttgctactaa aagtcatgca tcgtctcagg tagagctagg ctctaataat gtactagttt 660
atttgaaacg tacgtccggc atacggaaca agtagtaata atgagcatca gatcgcgtgc 720
aatgcagagg atagcagaat atacttgtat gtagctatgt ataggccacg acttgcgtaa 780
agctctaacg gctgttcacg accccaacgt cgtacgagag gccgggaaac aatcgtccag 840
caggccggcg gccggctagc tcggttgccg taagctacga ttcttagcac attaatatta 900
cattacatgc atgcatatcc cgcaccgctg tagcatctat acacagagta ctccacatct 960
acatctcctg gaggtcgatc gacctggcta gtactagtag tacacaggcc gcgggcgcgc 1020
gcgtttggtg cacgtcgtac acaacccccct tgaggaataa tcgcatgcct cgacgacgac 1080
gacgtcggag tcagcggcgt ggcaacaatg ttggttagtt gggcaaatta aattgaactc 1140
ccgaagagag acggttgaac tgatgactga gatgagtcgt cgtaaacgtg tgtgccaagg 1200
ttgggcaggg ttgggttggg ttgggccggg cgtacgtata cgtctctgat gcatcgtccc 1260
cctaaggacg gccgacgaca cacatctgtg acagtaactg acaaggactg catcactacg 1320
acgatgcacg cgtcattcgg attgtctgct tcagaataag cgagagctcc gtgccgtacg 1380
tgaccaaatc aaagcacagt cgctaacccc agcccagatg ttctagttga ctaagtgttg 1440
tttacttttt ttcccccctt aagtagatcg agtaacatcg ttatcgcgcg tattgacgga 1500
cagataacca taagctaagt ctatataagt tcggccggtg ctgagctact gcaggtagca 1560
ggatcgatat agcccaagcg atcgagaggg cattaattga ttgtgcttag ttttgtcggt 1620
tgccgctttg ctctggataa ctacaactac tccagctaga cgtagatcga cctagcgaga 1680
gctgtggact cgagagcgag atttcaactc ctgaacgcgc agtctgtacg tacagctacg 1740
gcctatctaa catgcctttc acttcattcc tcttctggat ttcatctccg caagtcccct 1800
gggatttgct cgttttggtt cagaggattc gctgcttaca cgcacggtcc tggggttaac 1860
ggagctcaac acagtagagt accatctctc attctctctt aatatcatcg gcatgcctta 1920
caactaagag tctgtcgtct tgaggcggtt gatataaaac attcaccatt gttaatagcc 1980
tattactcct gacgacagag gctatacctc agtctgtaga gccatggtgt agcctccatc 2040
ttggcatcaa caccgagcac cagtattatt t 2071

<210> SEQ ID NO 68
<211> LENGTH: 1577
<212> TYPE: DNA
<213> ORGANISM: Zea mays

<400> SEQUENCE: 68

```
aaggaccaac aacaagccaa aggaactaga tcactgacct cccattgcac tgaggagggc      60
tttgcgaagg gtgctcatgc acatcactct atatctagga atgagatgaa cacatgaatg     120
tttcaatcaa atgaaaaagg atggagagta ataggatggc aaggagtatt ttttgaaatt     180
tctaggcgtt ttcgaaataa tcataaatgt tggtggttgt gatgcctttt atgtaaccgc     240
gtagaagaag agagagagat agctatgctt atgataaaga agatgtgtgt tattgtttgt     300
atatgataat ttttatttac catgtgggta ttgatagtga tgcctacatg atgaatcatt     360
ttgaggagca atgcttgttt tcattattgg ccccaatgtt ttccaagatt ggacattatg     420
gaaggccttg acctcccacc ggtttattag gtaggtctcc tttatcttgc actaagactt     480
ctcatgttca tatccttagg cattggacat atggaccata caaaggtgaa aggaccatca     540
agatcctatt taggtccatt aaatatatat gtagttagaa gtagaagtgg caagtcaaga     600
ggactggtat gtcatacgtc acatgggtgc atgtcacatc ggagtgagct agcgctatca     660
agaagaaaat aaaggtaaat gtagcaatgg gtatattagt ctactatttg tacatgtgat     720
cctgaaagag acattaatat gttggcctag attggacttc ggtcttatag gacatgataa     780
gtaataactg aaactacttt cccgttccgt ttatcttatt tttcttcttc gcttcttcca     840
tctctatccc tatccctatc cctctctctc tcttttaaat tcttccccaa atatacatat     900
atatccctat tgcatccctg gatcgaaagg gacatgacaa ttcgtatgag atctaggctc     960
ttcatgcagg taattccttt attaccctct tggtcttgag tgacaatcat cattaactag    1020
tgttttcatt agacttgcac ttccattcca ggtctgtaat ctagtcattt tggactagag    1080
caattcacca tcacttgtaa ttggtaagca acttattctt tttaatttgc actatcatgg    1140
aggatgtgga agcgtgattg tgcaaattat ttggggacga acactcataa agaattttgg    1200
cggagttgat atgctcaagt aacaaatcat caacatcgac atcaattgta tcgactaggc    1260
catttggatc aaccaagtgc aagcaaagcc ggacttgtca atgtcttttc taggaaattc    1320
tcagcaagaa caacttcatg tcatgcatga tcttaaggag tcccttggtc caagggtagg    1380
acctctagat aaccatggtc cacaattgat gggaccgcct cctcaatttc aacctctacc    1440
atctcattct catatcatgc aggtgaattt acttgcctct tcttaaacaa gtgatttggg    1500
ttttttattt atgcggctgc tgtatgcatt gtgatgcttg ttgggtttac taatgcaagc    1560
tacggtgggc ttgtctt                                                   1577
```

<210> SEQ ID NO 69
<211> LENGTH: 2098
<212> TYPE: DNA
<213> ORGANISM: Zea mays

<400> SEQUENCE: 69

```
acggtcatgg gggcacgtga aagcgtacgc gtgcgcggcg ggcgcaccgt gcgcacgttg      60
gaccgagcgc ggaacggaag gcccgaaccc gaagcggcca aacccgccgc ggaaaacgta     120
cgagcgggga aggaggcgtg ggcgcccatg ctgctggggc cgccgttagc ctcgccggcg     180
cgcgatcgta ccgcgcggcg gcggcttttt tccatgggcg gtgccgcccc gccggcgggc     240
```

```
cctccctagt cccgtcgcaa gcggccgctg gtttggttgg tcgcttcgct cggcagaaag    300
cgagcactgt tgacgggttg gcgcggcgcg gggggctcgc ttttcttgcc gtcgactcgt    360
ggctggctgc accacctgac tggcggcggg cccaccgagg cggggaagtg ggaggagaca    420
ggccggatcc gcgaccgggg cggggagggc cccccgcccc acgtctgtct gctctgggaa    480
gtgaaaccaa accagcagac gaggacgaga caagccagcc agccagcccc cgtgttgctg    540
ccgccggccg ctctctgccc gcagcccaca gacaggaggg gcgtgggggg cccgggccgg    600
agagagccac ctcgcgactc gcgccgtcgc cgctcgcaac gactttaact gccacattta    660
tggccctgct ataaaacaaa ctgccgcatt taagacgcta ccggcctgag agagattcgg    720
gcagaatggg gaatgcagat gcatcagtgg tgcagcagtg ctacagtacc agcgtattgc    780
attgcatgtt gcatcgccgg aacgcgagca agattccttc gtcgtgaccg ctccacaacg    840
acccttgcct tggcttgcac tgtcaggtgg aagcattgtt cactgtcgga tacgtacatg    900
agatcatgtg tgcgacagac tgtacagcaa acagctagct cacatcacaa aacatgtggc    960
cgggcgcaca cagactaata agctctcgtt aatttagtgt acgccgaccg cgcgcgtcgg   1020
tctcactttg ctgctttgca tcagatcagg taggtaggta ggttatatat gtcattttgt   1080
taagaaccat ttgctaatta acaacctgcg ccgttttggc gccaaagttt tcagacagag   1140
ttaggtcaaa ccaatcctct cttctatttt attcatcaac gcgtattaac acaaccaacc   1200
acgtatagaa cgactcctaa aaagaggctc tttcttctgc agttgttttc tttctttctc   1260
ataatgtatg agcttcgaaa agttcagcaa ttgcttgctg cacttggatt acacatgttc   1320
attggtcgag tacgtgtcgt ttcagctgga tttgatgctg cgatgtagta accagctata   1380
gtgcacgcgt gggccctttt tatcaccccc aaacccacct ttaaggaaat cgtaaaggag   1440
atacgtacat ctctatctag cttcaacgaa aggtgcgtgc caaaaacaat ggcagatgac   1500
tagattttgt gattggatga tatggaaagc aattattaat catcttttga tatctcgcgg   1560
tcggattcat ttgattgata gagagccggc gttccacttt tcatattttt gcccctacta   1620
gcagacagtg gctctgtaac ttccaatatg gatttgtggg actgaagggt taattattat   1680
ctgtattctg tataatcggt ggctgtatgt acgatataat cattttgaaa cataacggta   1740
cattatttct cattcctgtc caagaagctt aagtcatgta tggatctaac taacaacagg   1800
ctaactaact tcttagtcta tgatgatcca aatatacaaa ctaaaatatg agtccgctag   1860
ttaataggac tagtagttgt tagtttcata tatcaatcca gttgttactc tctggtaaca   1920
tcaatctaac aagagttcag tccatgctgt ttgtctcacg caaatatatg tgttacgttg   1980
aacgccattc gatagtggta tattatcaac ttatcttgtg gttaatatga ttagcaaaag   2040
aataacacca tttgtcacta tattttactt ctatagtata agtagttttt aggaatac     2098
```

<210> SEQ ID NO 70
<211> LENGTH: 1580
<212> TYPE: DNA
<213> ORGANISM: Zea mays

<400> SEQUENCE: 70

```
gttccgtccg catctgcaca agtgatcgaa cggcacaccg cacacgcaac cggccggggc     60
cgtgaatagt ttcctgaaga cgattcccca acgacgacga cgacgacgcg cacagccacg    120
cggcacagtg ctcatcaagt acacagtagc acacacagcg tgcgtgcggc tgcaattaat    180
catatatacg ggttatttaa gggcaggcaa agcaaggcga ggcaagcagg aggccgacgg    240
cgaggtcacc cacccagcgg cggcgtacca gcacacgcta cgccagtcgg gcagtcgtgt    300
```

```
gttttttat gatagaattt tcttcgtaga catatagatg ctggtattga ttgagatgtg    360
gctagagtga tcggccggca tgcatgcgat gcgatgcgtt gcgacggagg ggagatcctt    420
ctcctgctat ctcgtctcgt ctctatacta gctccgcgcc aagaacgtcg tcacagaacg    480
tacttactac cagcaggggg ccgggcccgg gaggggctct ggccggtcga cagatcgttg    540
gcaaccaccg ccggccactc attgagcgag atgcatgggc tagtaggcta atcctatatt    600
ttttttaaca cgcatgcata tgctgatcaa tgcgaacaga cggactgaac tcgacccatc    660
tggatgtagc agtagtggtg gctgctgttt ggctggcatg gcatggcatg cgtccggcag    720
gcacgcatga cagcatccat ccagtacctt attgtctaca tcgaatattt tgaaaatttt    780
aaattcgctg gttttcgtcg actggctata tatagcgcat ggaaatgaat ttaatttagc    840
tgcagatgga aggttgttag aggacgaagg agctcaaatc gagcttttgc atggaataat    900
ttatacgttc ccagcatata tatgcataca tagacataga gctgaaccgg cgcatgtcta    960
cctactacat acaaacgagg cagatgaggt tgctagtagc tcgacgatca tgcccttgtt   1020
cttctttatt ccccatttaa tagcaaatag agagagagag agattaaaaa aagggaaatt   1080
gttcagtcag gagtcaaatt ccttctctat ctagaggcaa tacacgcagt atatatacac   1140
atatctctgt caccggatta ttgaaacttt tgtttaagta gtatagtagt atatagcaag   1200
caagatttta aaattttggg tgccctcaac tatacataca aaattcacca ttcacatggc   1260
ctgcttgcca ctccttcggt ccttaagagc tgctgtgccc tgccctgcgc agactgcatg   1320
agcgcgcgca agaatgttca gaaggcaaca gaacaggtcg tgcagaaatt aaattaaaat   1380
agaagaatcc atgtgagcta agctaagcat gcagcagccg ctccgtcaaa tatgtcaatg   1440
catcaaggag agtagagctc ccaatcctgc tgcttgccac ccgtcgtgga cgcacacgca   1500
tggatccgtg ttgcatatgg ccagctcgat cggagcagcg gcaggcgtca tcatccgtga   1560
cagcaacggc gcaaccaccg                                               1580
```

```
<210> SEQ ID NO 71
<211> LENGTH: 1972
<212> TYPE: DNA
<213> ORGANISM: Zea mays

<400> SEQUENCE: 71

gctggtgcgc gtctcaaagg cgctcgagga cttccgcgcc tccaacgccg agggttcgca     60
ccattcgcct ccctttattt tggctcctgt ttttgaactt cggagcggca aatttggtgc    120
gttcgaacga gtgtagcagt agtgttgatg cgccgctcag tggactttgc gcctggggct    180
agagtttgag cgtatccctt ccaattcttg ccccatttgg tccttgtgct tttctgttct    240
ttttttccaa ctccattaga acagtgtatt ttttgtcctg tgatcctgtc gtccttagtc    300
ctgagtgcat ttgcattaca acctgctttg tggtttgctt tgatgtttct gttgtgtact    360
gatcacaata gtgctgctgt ttctcatcca cattgtgctt ttatcaacat gtctgttcac    420
acttgcagtt acatataatt tgcacatcgg ctctctgatg ctaatattgt cacacaaagt    480
ttgaacgttt tcttaggttt gacatgtgct aagtggtgca ttcagtgttt gtaatgtagc    540
tttccagtga tatattttgg aattggccaa tcttaggtta tagaatgcaa tcgtctttcc    600
acaaacttat aactgttttc cattgggttg catcttgcaa ttttagacat gattgttgtg    660
agatagctgt acgcctccta gataatatag taaaattgcc ttgcaaaagt ctttgcatgt    720
tttcatggct gtatattagt gggagtacca gcacattgag cacaagcaca gacccaatta    780
```

```
attgtttgat ataatttatt gatggtagaa ttctagttac gcgcataagg gtcagtgtag    840

cagtagatct tcttattttg atggcatttt tttttctcgt atattggctg gccctacttc    900

agtttaagcc tcacccatct atattatgta gtaatgcatt gagattattg ctctcttcct    960

ttggtgctgt gagctgaata aactgatact tagactattt taccttgcag tgtacacatt   1020

tgaacctgat atatccaaac aagagcgagc tgcaatccat gagatgtgta ggaaaatggg   1080

catgatatcc aaaagttctg ggtgagtaag ataactagga ttcattgagc aaaattgttt   1140

catcgaagag ttgtaaggaa tctatggtta tgcttgcgcc atcctaatgt tatctttaca   1200

aaagttactt gttaaatgtc tattctgagt tctatttaac ttcaggaacg gggaacgtcg   1260

acgcctttct gtttataaaa gaaaacagaa gcgggggcct gaattggaac aaggccctag   1320

ctaccttggg ttttctgaag aggctaggca tgttttgcag gatttattta tgcattatcc   1380

tcctggtgat gctgatttaa gtggggatgt tgaccagagt tctagtgata aggctgcaaa   1440

catcaaatgg agaacagata atgcgttttg caggcccgca atgagtaaac ttgatataac   1500

gaagaaagtt gagatgcttg cctcaaaaat aaatggatcc gaacagttga gaaaggtctc   1560

acattctggc ttgacaatag tatcttcctc tctttgctta gttgctgcta cttattagtt   1620

ttatttatga gacaatctta tttatagcta aagcttaaag gtttactttt gaacaggtca   1680

tggaagatag aacaaaactt cctatttcat ctttcaagga tgtcatcact tcaactttgg   1740

aaaatcacca ggtatagttt ttagctccaa aggtttctca catttgctag accacatctt   1800

caactcacat ggtgcactgg tgctattttt tcctctcaga tgtgcaggga aactgttttt   1860

tttttcatta aagaagcata gcataataca acaatcccca atccccaagg ccccaaccaa   1920

aaaacagaaa ggaaaaactg ggtttccact gtgaattttg gaacatgcat ac           1972
```

<210> SEQ ID NO 72
<211> LENGTH: 20
<212> TYPE: DNA
<213> ORGANISM: Zea mays

<400> SEQUENCE: 72

```
agcaccggtt gctcggaccg                                                  20
```

<210> SEQ ID NO 73
<211> LENGTH: 20
<212> TYPE: DNA
<213> ORGANISM: Zea mays

<400> SEQUENCE: 73

```
tacagaaacg cggagagact                                                  20
```

<210> SEQ ID NO 74
<211> LENGTH: 20
<212> TYPE: DNA
<213> ORGANISM: Zea mays

<400> SEQUENCE: 74

```
taacgagcag agtacacacg                                                  20
```

<210> SEQ ID NO 75
<211> LENGTH: 20
<212> TYPE: DNA
<213> ORGANISM: Zea mays

<400> SEQUENCE: 75

```
tgaaagcgat gcggtttaga                                                  20
```

<210> SEQ ID NO 76
<211> LENGTH: 20
<212> TYPE: DNA
<213> ORGANISM: Zea mays

<400> SEQUENCE: 76
tacaatgtac agtctagcca 20

<210> SEQ ID NO 77
<211> LENGTH: 20
<212> TYPE: DNA
<213> ORGANISM: Zea mays

<400> SEQUENCE: 77
acgagaccat ccaatgatcg 20

<210> SEQ ID NO 78
<211> LENGTH: 20
<212> TYPE: DNA
<213> ORGANISM: Zea mays

<400> SEQUENCE: 78
tggagagtaa taggatggca 20

<210> SEQ ID NO 79
<211> LENGTH: 20
<212> TYPE: DNA
<213> ORGANISM: Zea mays

<400> SEQUENCE: 79
tgaaaccaaa ccagcagacg 20

<210> SEQ ID NO 80
<211> LENGTH: 20
<212> TYPE: DNA
<213> ORGANISM: Zea mays

<400> SEQUENCE: 80
taggtttgac atgtgctaag 20

<210> SEQ ID NO 81
<211> LENGTH: 20
<212> TYPE: DNA
<213> ORGANISM: Zea mays

<400> SEQUENCE: 81
cttcgtagac atatagatgc 20

<210> SEQ ID NO 82
<211> LENGTH: 988
<212> TYPE: DNA
<213> ORGANISM: Zea mays

<400> SEQUENCE: 82
ccgtggagaa aactggttgg gctgtgccga gaaacaatga gcgggctggg ctgcgtcttg 60
acggcgggcc accaaactgt cccgccgtgc gcgcagggca acaaccacaa cgtcatgtgc 120
ggcttgctta actgggcccg ttagacgcgg gcttcgtgtg gccttggaac acggccgttc 180
gacctggctt cacgtgacgt gaaccagagc ggagcggggc catcgatttc ggccgcgcga 240
aacgcgtgcg cgaggcctgc gaaaggccgc tggatgaagc tccctttgat tgaagcccgt 300

```
gtgggccgca ccgcatggtc cggccggcga tcgtgaccgt tggagtacga tttattcgat    360

gcgtatgtac tcagctcgat ccatatacga tatgatagta cgtagacatc ttagacgtaa    420

gttgtttaag gaactctctc tctctctctc tctctctctc gggtttctgt gttcatctca    480

aagtttttc agttcaaaaa ccaattcgaa aacaaatcgg cttaaaattc aggtaatcag    540

gtcaagcgac tttactctgg tctgaataac ttgagacatc cgggttgcca tggccgactc    600

tagacagcgg ccataaacac ggtggtttct ttttcttatt gggatagtag gtcactccaa    660

ataaaggcta ttgccatatg ctaaggagac ggaatttgtg acgccatcgc caccgggtta    720

acgttaatat tctactacta gagaatctag cttacgtttc ggttccggcc ggccagtaga    780

aaactctctc tgaaccgacc ggtcagaatc ccctgctcgg tgctcggttg cttggaccgc    840

acgcacgcac ccctatatcg tcagtgcctg taacagttct tattcggtga ttattattat    900

aatattattc cacgtttgca cacaccgcac atccgcccgt ttgtaaaact gtgagttgat    960

cgtcgagacg aaaggtggag ctggagta                                        988
```

<210> SEQ ID NO 83
<211> LENGTH: 1001
<212> TYPE: DNA
<213> ORGANISM: Zea mays

<400> SEQUENCE: 83

```
ctctccgcgt ttctgtaact agaattgtca tagtcagggt tgccaaacat cagcatcccg     60

aggcagtttc tttaattctg cttttttta tatatgtaag tttgcttacc gaatgagcta    120

gttctaaaca aactcaaaaa caaaacaggg caactggggg tcccttgaca ttgcacagat    180

ggacctgacc actttgagat tcccccggct tctatctcct tttccctccc cttggatcaa    240

atgaacaaag gagcgcattc tctctctctc tctctctcta aaagattaaa aaaaagcctg    300

catgtagtgt tctttgacaa ggacaaggaa gccctttac atcaatacat cattcgtatg    360

ttgttgtttt ctgtgttctt tgcgttcctt tttttcccct ccctccgcct tttttctact    420

tgattgttgc caagatctgg agcacctgct ctgatctgat tgtgtgcgct ggtttactga    480

acctttcgga gggctatacg cttcgtacgg ggacatacca atttcaaaga attcagtcat    540

caggtaggtg gttcaatcat accgatggtt tcctcactgc atcactcacc ttctcatttt    600

tacgcatcat aattttttgt tcccttctcc ttaattccca tgcggtgaag gagagatgtg    660

aactaacagt ttggcgctgc actgttcgac cggctaaaca cggggccaat gctctctgta    720

cgtgcagatg gataggatag tctttgattc ttgtttcaag atgacgtgga tagtctataa    780

tagctaaatg tttgcctcga ctactaactt gccgatatgg gcgagggtaa ctttaaatta    840

aatttttaaa gcatttgact tgttaaaaaa aataaaagcc tatattcttt gttgatggag    900

ggagcaagtg gctgaaaagc cgttgccatt tctgggcgct ccctaaacta cgcggcaagc    960

aggctattgg gagcccttgt cgctgtcgac gcgatgtgcg g                       1001
```

<210> SEQ ID NO 84
<211> LENGTH: 1000
<212> TYPE: DNA
<213> ORGANISM: Zea mays

<400> SEQUENCE: 84

```
acgtgggcta gctctccgct gaaaagaata cgatttacat acgtgtaaag gttgtgccca     60

ctcggcagaa atttggtgat gcggggccag gtcgttagcc tcggatgcag cctgcaggca    120

gcctgtggtg tggtgtggtc caaaaagggc gggaacagaa acgaggggct ggacgcctgg    180
```

```
acccatggat caggtggtgg tggtccgtgt gggcgcaagc accagtacag tacagtacag    240

tacttccccc cccgctcctg catgcatcgt cctctgtaaa cacaaggctt tacccgaaag    300

cacaagctca cctaattaag ctcatgtacg cttctggcgc gcacaataga cacgcccgta    360

cgcaggagca catggcacca accgaatgat ttgagcaacc gtctccgcat ctggaatcca    420

ttccactcac ccaaacagag ctccagctcc ccctctatcc agcgagctgg acgggacggg    480

acggagcgta gactagcaga acagaagcca ggcaggtcgt ccggtcgggg tcctttccct    540

ctttctctcc gttttctccg ctggggaaaa agaaaatcgg aaaatgacgc tccacggaag    600

aagcgcgcga gccgatggca atggttcccg tcagcgtcga gcggcgatgg tccccgagac    660

tttttccccc cctcctcccc tgcgtgccgc acacggccgg aacggtcctt gctgttgcgg    720

ctttctatct tggaacagcg ccggccggtt gaatccgccg tgttcctagt gcaagttgca    780

gagcggagca aagcaaggga ccttgccgca aaaaccgtgg cggggtgtcg tctaactttg    840

tccgtcaagg gtcgccgtcg gccttgacaa aacggacagc tgctgaccgt gacgagttag    900

aagagagaga gagagggaga tagaagaaaa atcacccacc tccggacctc cccacacgaa    960

acgaaaagct acgacctacc tctcttccag acgtaacgta                         1000
```

<210> SEQ ID NO 85
<211> LENGTH: 990
<212> TYPE: DNA
<213> ORGANISM: Zea mays

<400> SEQUENCE: 85

```
aaaccgcatc gctttcaggc tttatttaat ctctgcgtca aggaaaggag caatcttctg     60

cgagaaaaga agaaggtctc gcgtccatgt atgcagttga actgtttact catgagaatg    120

agaggggga gagagacatc agacatccca gtgaaggttt cagagacgcg actgttgatc    180

cgatggcccc ggcccctcat cagcaataat cagctggacc gaaaaagata cacgtactgg    240

gattttccat gtaccccca aaaacaatat tagctcatgc atgaactggg cgattatatc    300

gtcatttaat ttgtgggtta catgttgttt atgcgtagag agaagataga gttggtagca    360

agtcccggtt tgtgcatagc aagatgtgat ttttgtccat taattcgtca gtaggtgatg    420

attgactctg acgatgagac cgacaggcgg acgcatatat tatgcatcga tgtgcattct    480

gtgtgtgatt tgtgactcaa tattattcct ctggctagtc ttgttcccgg ccatttctcc    540

ctgaattccc ctctgatctt tttttaatat tttatgtaaa gaaagaaaaa aacactgaag    600

gccgacgata tgcgcgtgag gacgacaatc gcacacgtgt ttgcatttga taacatttta    660

tcttgtctag cagacattag tttgattaac ttgtttcatg ccaatcatta atttggagta    720

tatatgattg atatcttatt atcctgtccg tttgtatatt atttaagtag catggattgg    780

agtactacac cgttaacaat acattccaca aataccttc cctccatcca aattaaggct     840

taattttaga taatgacgca tcttcttcct atagcccacc ctatgcacag gtaagcctca    900

caaggtacgt agtttttaca ctaattatta gctttgcaaa ttgcaatata gctacaagtt    960

ttgcatcggc tgattttttt gattaattgg                                     990
```

<210> SEQ ID NO 86
<211> LENGTH: 993
<212> TYPE: DNA
<213> ORGANISM: Zea mays

<400> SEQUENCE: 86

-continued

```
ctagactgta cattgtactt gaatactctg ggtgaccaac ccccagaaca cgtccttcta     60
tctacagatg gcaattaaaa aaagataaat tgcatacttc aacaagtgaa ttacaagcac    120
atttacattt ccattgtttt gctaccatgc tttgatgctt tcattgaatg ggtacaggtg    180
ttaagcagca gagtgacaga agatgacaac atatattcgt atagttctga aaggttatat    240
tttaacctat ttgtatgcga tcaaccaaaa atggacaatt ataagtatgg tcaagtaaga    300
tgatagtata gcataactca aatattgtta ttgtggaata tcacattggt atcaattatg    360
acagaggcac aaaatttcaa gaataaatgt taaacataaa taagcaagag cacaaaaagt    420
tgaggtgtgg taccttcaaa gcacgctgca aaaggggga aacaacaaac agaaaagggt     480
ataagaagca agttcaaatc ttcgaatgaa aaaaattaag ttcaagactt ggaatgaaaa    540
aattaagtgc agaaagtata gcagcagttg acacaaaggg tataatgcta caatggaaac    600
agttcaatta gcctttcaca acttcatgag aaaaatacat caaggatctc ccctactgtg    660
acttcgttac taaatttcat tctgtgtatc atgataatga tgcatatagt gaggactagc    720
atgcctcaaa caaaaagctg cctacaaaaa tgtccattcg ctcacttgca gcttgaacag    780
agtattagca tgcaaaattt tgcacagatt tacaaatttc ttagattatg attcccatca    840
aaggtaacag atattgtcat tcctacaaac tattgcatgc ggtctgtttt caaactgttt    900
aatgatattc accaaaaaag acaaaaacaa acttttcaaa ctgtgttgca tagcaaaatt    960
acagaagaaa ctataaaatc taaacaaaga aga                                 993
```

<210> SEQ ID NO 87
<211> LENGTH: 998
<212> TYPE: DNA
<213> ORGANISM: Zea mays

<400> SEQUENCE: 87

```
tcattggatg gtctcgtacg taagtttact acccgacgtt gcaccgcgaa attcaaatgc     60
cagtgccgaa ctaagtttgg ctgtcataca tcgtcagaag gaaaacagaa cccccaaaaa    120
aaaacataat gaggtattcc catcagaggt aagcagctta ggcggctgag ttgaatttga    180
ctgaataata tccatgcttg tgtgtgcgtg cctaacgcat tgtcgtcgtg ttctacgtac    240
gctgctgcat gctactactt tgctactaaa agtcatgcat cgtctcaggt agagctaggc    300
tctaataatg tactagttta tttgaaacgt acgtccggca tacggaacaa gtagtaataa    360
tgagcatcag atcgcgtgca atgcagagga tagcagaata tacttgtatg tagctatgta    420
taggccacga cttgcgtaaa gctctaacgg ctgttcacga ccccaacgtc gtacgagagg    480
ccgggaaaca atcgtccagc aggccggcgg ccggctagct cggttgccgt aagctacgat    540
tcttagcaca ttaatattac attacatgca tgcatatccc gcaccgctgt agcatctata    600
cacagagtac tccacatcta catctcctgg aggtcgatcg acctggctag tactagtagt    660
acacaggccg cgggcgcgcg cgtttggtgc acgtcgtaca caaccccctt gaggaataat    720
cgcatgcctc gacgacgacg acgtcggagt cagcggcgtg gcaacaatgt tggttagttg    780
ggcaaattaa attgaactcc cgaagagaga cggttgaact gatgactgag atgagtcgtc    840
gtaaacgtgt gtgccaaggt tgggcagggt tgggttgggt tgggccgggc gtacgtatac    900
gtctctgatg catcgtcccc ctaaggacgg ccgacgacac acatctgtga cagtaactga    960
caaggactgc atcactacga cgatgcacgc gtcattcg                            998
```

<210> SEQ ID NO 88
<211> LENGTH: 999

<212> TYPE: DNA
<213> ORGANISM: Zea mays

<400> SEQUENCE: 88

```
gcaaggagta ttttttgaaa tttctaggcg ttttcgaaat aatcataaat gttggtggtt     60
gtgatgcctt ttatgtaacc gcgtagaaga agagagagag atagctatgc ttatgataaa    120
gaagatgtgt gttattgttt gtatatgata atttttattt accatgtggg tattgatagt    180
gatgcctaca tgatgaatca ttttgaggag caatgcttgt tttcattatt ggccccaatg    240
ttttccaaga ttggacatta tggaaggcct tgacctccca ccggtttatt aggtaggtct    300
cctttatctt gcactaagac ttctcatgtt catatcctta ggcattggac atatggacca    360
tacaaaggtg aaaggaccat caagatccta tttaggtcca ttaaatatat atgtagttag    420
aagtagaagt ggcaagtcaa gaggactggt atgtcatacg tcacatgggt gcatgtcaca    480
tcggagtgag ctagcgctat caagaagaaa ataaaggtaa atgtagcaat gggtatatta    540
gtctactatt tgtacatgtg atcctgaaag agacattaat atgttggcct agattggact    600
tcggtcttat aggacatgat aagtaataac tgaaactact ttcccgttcc gtttatctta    660
tttttcttct tcgcttcttc catctctatc cctatcccta tccctctctc tctcttttaa    720
attcttcccc aaatatacat atatatccct attgcatccc tggatcgaaa gggacatgac    780
aattcgtatg agatctaggc tcttcatgca ggtaattcct ttattaccct cttggtcttg    840
agtgacaatc atcattaact agtgttttca ttagacttgc acttccattc caggtctgta    900
atctagtcat tttggactag agcaattcac catcacttgt aattggtaag caacttattc    960
tttttaattt gcactatcat ggaggatgtg gaagcgtga                            999
```

<210> SEQ ID NO 89
<211> LENGTH: 997
<212> TYPE: DNA
<213> ORGANISM: Zea mays

<400> SEQUENCE: 89

```
acgaggacga gacaagccag cagccagctc ccgtgttgct gccgccggcc gctctctgcc     60
cgcagcccgc agcccacaga caggaggggc gtggggggcc cgggccggag agagccacct    120
cgcgactcgc gccgtcgccg ctcgcaacga ctttaactgc cacatttatg gccctgctat    180
aaaacaaact gccgcattta ataggctacc ggccaggcct gagagagatt cgggcagaat    240
ggggaatgca gatgcatcag tggtgcagca gtgctacagt accagcgtat tgcattgcat    300
cgccggaacg cgagcaagat tccttcgtcg tgaccgctcc aaaacgaccc ttgccttggc    360
ttgcactgtc aggtggaagc attgttcact gtcggataca tacatgagat catgtgtgcg    420
acagactgta cagcaaacag ctagctcaca tcacaaaaca tgtggccggg gcgcacacag    480
actaataagc tctcgttaat ttagtgtacg ccgaccgcgc gcgtcggtct cactttgctg    540
ctttgcatca gatcaggtag gtaggtaggt tatatatgtc attttgttaa gaaccatttg    600
ctaattaaca acctgcgccg ttttggcgcc aaagttttca gacagagtta ggtcaaacca    660
atcctctctt ctattttatt catcaacgcg tattaacaca accaaccacg tatagaacga    720
ctcctaaaaa gaggctcttt cttctgcagt tgtttttttt ttctcataat gtatgagctt    780
cgaaaagttc agcaattgct tgctgcactt ggattacaca tgttcattgg tcgagtacgt    840
gtcgtttcag ctggatttga tgctgcgatg tagtaaccag ctatagtgca cgcgtgggcc    900
ctttttatca cccccaaacc cacctttaag gaaatcgtaa aggagatacg tacatctcta    960
```

```
tctagcttca acgaaaggtg cgtgccaaaa acaatgg                              997


<210> SEQ ID NO 90
<211> LENGTH: 999
<212> TYPE: DNA
<213> ORGANISM: Zea mays

<400> SEQUENCE: 90

aagtggtgca ttcagtgttt gtaatgtagc tttccagtga tatattttgg aatctcccaa      60

tcttaggtta tagaatgcaa tcgtctttcc acaaacttat aactgtttac cattgggttg     120

catcttgcaa ttttagacat gattgttgtt agatacctgt acgcctccta gatatatagt     180

aaaattgcct tgcaaaagtc tttgcatgtt ttcatggctg tatattagtg ggagtaccag     240

cacattgagc acaagcacag acccaattaa ttgtttgata taatttattg atggtagaat     300

tctagttacg cgcataaggg tcagtgtagc agtagatctt attttgatgg cattcttttt     360

ctcgtatatt ggctggccct acttcagttg aagcctcacc catctatatt atgtagtaat     420

gcattgagat tattgctctc ttcctttggt gctgtgagct gaataaactg atacttagac     480

tattttacct tgcagtgtac acatttgaac ctgatatatc caaacaagag cgagctgcaa     540

tccatgagat gtgtaggaaa atgggcatga tatccaaaag ttctgggtga gtaagataac     600

taggattcat tgagcaaaat tgtttcatcg aagagttgta aggaatctat ggttttgctt     660

gcgccatcct aatgttatct ttacaaaagt tacttgttaa atgtctattc tgagttctat     720

ttgacttcag gaacggggaa cgtcgacgcc tttctgttta taaaagaaaa cagaagcggg     780

ggcctgaatt ggaacaaggc cctagctacc ttgggttttc tgaagaggct aggcatgttt     840

tgcaggattt atttatgcat tatcctcctg gtgatgctga tttaagtggg gatgttgacc     900

agaattctag tgataaggct gcaaacatca aatggagaac agatagtgcg ttttgcaggc     960

ccacaatgag taaacttgat ataacgaaga aagttgaga                            999


<210> SEQ ID NO 91
<211> LENGTH: 986
<212> TYPE: DNA
<213> ORGANISM: Zea mays

<400> SEQUENCE: 91

tgctggtatt gattgagatg tggctagagt gatcggccgg catgcatgcg atgcgatgcg      60

ttgcgacgga ggggagatcc ttctcctgct atctcgtctc gtctctatac tagctccgcg     120

ccaagaacgt cgtcacagaa cgtacttact accagcaggg ggccgggccc gggagggggct    180

ctggccggtc gacagatcgt tggcaaccac cgccggccac tcattgagcg agatgcatgg     240

gctagtaggc taatcctata ttttttttaa cacgcatgca tatgctgatc aatgcgaaca     300

gacggactga actcgaccca tctggatgta gcagtagtgg tggctgctgt ttggctggca     360

tggcatggca tgcgtccggc aggcacgcat gacagcatcc atccagtacc ttattgtcta     420

catcgaatat tttgaaaatt ttaaattcgc tggttttcgt cgactggcta tatatagcgc     480

atggaaatga atttaattta gctgcagatg gaaggttgtt agaggacgaa ggagctcaaa     540

tcgagctttt gcatggaata atttatacgt tcccagcata tatatgcata catagacata     600

gagctgaacc ggcgcatgtc tacctactac atacaaacga ggcagatgag gttgctagta     660

gctcgacgat catgcccttg ttcttcttta ttccccattt aatagcaaat agagagagag     720

agagattaaa aaaagggaaa ttgttcagtc aggagtcaaa ttccttctct atctagaggc     780

aatacacgca gtatatatac acatatctct gtcaccggat tattgaaact tttgtttaag     840
```

```
tagtatagta gtatatagca agcaagattt taaaattttg ggtgccctca actatacata    900

caaaattcac cattcacatg gcctgcttgc cactccttcg gtccttaaga gctgctgtgc    960

cctgccctgc gcagactgca tgagcg                                         986


<210> SEQ ID NO 92
<211> LENGTH: 22
<212> TYPE: DNA
<213> ORGANISM: Zea mays

<400> SEQUENCE: 92

tgacaagacc acacacacgc at                                              22


<210> SEQ ID NO 93
<211> LENGTH: 23
<212> TYPE: DNA
<213> ORGANISM: Zea mays

<400> SEQUENCE: 93

gtgacggact gacggtgagt atc                                             23


<210> SEQ ID NO 94
<211> LENGTH: 23
<212> TYPE: DNA
<213> ORGANISM: Zea mays

<400> SEQUENCE: 94

atgatgtgtg tgtgtgtgcc tgt                                             23


<210> SEQ ID NO 95
<211> LENGTH: 21
<212> TYPE: DNA
<213> ORGANISM: Zea mays

<400> SEQUENCE: 95

tgcccacttt tgctttcaca t                                               21


<210> SEQ ID NO 96
<211> LENGTH: 23
<212> TYPE: DNA
<213> ORGANISM: Zea mays

<400> SEQUENCE: 96

tgaactgttg aaacaccaaa tgc                                             23


<210> SEQ ID NO 97
<211> LENGTH: 20
<212> TYPE: DNA
<213> ORGANISM: Zea mays

<400> SEQUENCE: 97

tcagcaccgg ccgaacttat                                                 20


<210> SEQ ID NO 98
<211> LENGTH: 22
<212> TYPE: DNA
<213> ORGANISM: Zea mays

<400> SEQUENCE: 98

gctttgcttg cacttggttg at                                              22


<210> SEQ ID NO 99
```

-continued

```
<211> LENGTH: 25
<212> TYPE: DNA
<213> ORGANISM: Zea mays

<400> SEQUENCE: 99

gcttcttgga caggaatgag aaata                                             25


<210> SEQ ID NO 100
<211> LENGTH: 24
<212> TYPE: DNA
<213> ORGANISM: Zea mays

<400> SEQUENCE: 100

agcagcaact aagcaaagag agga                                              24


<210> SEQ ID NO 101
<211> LENGTH: 19
<212> TYPE: DNA
<213> ORGANISM: Zea mays

<400> SEQUENCE: 101

aagcagcagg attgggagc                                                    19


<210> SEQ ID NO 102
<211> LENGTH: 21
<212> TYPE: DNA
<213> ORGANISM: Zea mays

<400> SEQUENCE: 102

tgtgctgcaa ggcgattaag t                                                 21


<210> SEQ ID NO 103
<211> LENGTH: 21
<212> TYPE: DNA
<213> ORGANISM: Zea mays

<400> SEQUENCE: 103

tgtgctgcaa ggcgattaag t                                                 21


<210> SEQ ID NO 104
<211> LENGTH: 21
<212> TYPE: DNA
<213> ORGANISM: Zea mays

<400> SEQUENCE: 104

tgtgctgcaa ggcgattaag t                                                 21


<210> SEQ ID NO 105
<211> LENGTH: 20
<212> TYPE: DNA
<213> ORGANISM: Zea mays

<400> SEQUENCE: 105

ccgggtgaat cagcgtttat                                                   20
```

TARGETED INSERTION SITES IN THE MAIZE GENOME

RELATED APPLICATIONS

This application is a 371 of International Application No. PCT/US2018/065114, filed Dec. 12, 2018, which claims the benefit of U.S. provisional Application No. 62/599,831, filed Dec. 18, 2017, the contents of which are incorporated herein by reference.

STATEMENT REGARDING ELECTRONIC SUBMISSION OF A SEQUENCE LISTING

A sequence listing in ASCII text format, submitted under 37 C.F.R. § 1.821, entitled "81487_ST25.txt", 206 kilobytes in size, generated on Dec. 14, 2017 and filed via EFS-Web is provided in lieu of a paper copy. This sequence listing is hereby incorporated by reference into the specification for its disclosures.

BACKGROUND OF THE INVENTION

Recent advances in the field of targeted genomic modifications have made it so that routine targeted modifications for agrobiotechnological approaches may soon be possible. Significant advances include the development of methods and compositions to target and cleave genomic DNA by site specific nucleases (e.g., Zinc Finger Nucleases (ZFNs), Meganucleases, Transcription Activator-Like Effector Nucleases (TALENS) and Clustered Regularly Interspaced Short Palindromic Repeats/CRISPR-associated nucleases (CRISPR/Cas) with an engineered crRNA/tracr RNA), to induce targeted mutagenesis, to induce targeted deletions of DNA sequences, and to facilitate targeted recombination of an exogenous donor DNA polynucleotide, such as a transgene, within a predetermined genomic locus. However, this predetermined genomic locus is not obvious. Many sites in the genome are non-ideal for targeted genomic modifications, particularly for targeted insertion of a DNA of interest, due a number of factors, including highly repetitive nucleotide sequences, methylation, chromatin structure, epigenetic modifications such as acetylation, and other characteristics that result in a high level of recombination or a poor level of expression of introduced coding sequences. Therefore, there is a need in the art to identify ideal target sites within a genome for targeted modifications such as transgene insertion. The present invention addresses these shortcomings in the art by providing ideal target sites for a maize genome.

SUMMARY OF THE INVENTION

The present invention provides a method of integrating a DNA of interest into a target maize genomic locus, wherein the target maize genomic locus comprises a nucleic acid sequence of at least 100, at least 500, at least 750, at least 1,000, at least 1,250, or at least 1,500 contiguous nucleotides having at least 70%, at least 75%, at least 80%, at least 85%, at least 90%, at least 93%, at least 95%, at least 96%, at least 97%, at least 98%, at least 99%, or 100% identity to at least 100, at least 500, at least 750, at least 1,000, at least 1,250, or at least 1,500 contiguous nucleotides of SEQ ID NO: 1 through SEQ ID NO: 71, or a complement thereof, comprising introducing into a maize cell: (a) a first nucleic acid molecule comprising at least 50, at least 60, at least 70, at least 80, at least 90, at least 100, at least 110, at least 120, at least 130, at least 140, or at least 150 contiguous nucleotides, wherein said contiguous nucleotides have at least 80% identity to at least 100, at least 110, at least 120, at least 130, at least 140, or at least a 150 contiguous nucleotides of SEQ ID NO: 1 through SEQ ID NO: 71, or a complement thereof, and further comprising a DNA of interest; and (b) a second nucleic acid molecule comprising a nucleotide sequence encoding a nuclease for site-directed cleavage at a genomic nuclease cleavage site of, adjacent to, or proximal to the genomic nucleotide sequence of SEQ ID NO: 1 through SEQ ID NO: 71, or a complement thereof, that corresponds to the contiguous nucleotides of (a), under conditions wherein expression of the second nucleic acid molecule can occur to produce the nuclease and the nuclease can cleave the nucleotide sequence at the genomic nuclease cleavage site, whereby the DNA of interest is integrated at the genomic nuclease target cleavage site in the maize genome.

In some embodiments, the first nucleic acid molecule and the second nucleic acid molecule can be introduced into the maize cell by biolistic nucleic acid delivery, via an *Agrobacterium*, by co-transformation, and/or with a T-DNA vector in any combination and/or order. In some embodiments, the first nucleic acid molecule and the second nucleic acid molecule can be present on a single nucleic acid construct or on separate nucleic acid constructs.

In some embodiments, the first nucleic acid molecule and/or the second nucleic acid molecule can be transiently expressed in the maize cell or can be stably integrated into the maize genome of the maize cell.

In some embodiments, the DNA of interest comprises at least one expression cassette. In some embodiments, the DNA of interest comprises a transgene.

In another embodiment, the present invention provides a method of making a maize plant cell comprising a DNA of interest, said method comprising: (a) selecting a target maize genomic locus, wherein the target maize genomic locus comprises a nucleic acid sequence of at least 100, at least 500, at least 750, at least 1,000, at least 1,250, or at least 1,500 contiguous nucleotides having at least 70%, at least 75%, at least 80%, at least 85%, at least 90%, at least 93%, at least 95%, at least 96%, at least 97%, at least 98%, at least 99%, or 100% identity to at least 100, at least 500, at least 750, at least 1,000, at least 1,250, or at least 1,500 contiguous nucleotides contiguous nucleotides of SEQ ID NO: 1-71 or a complement thereof; (b) selecting a site specific nuclease that specifically binds to and cleaves a genomic nuclease cleavage site within said target maize genomic locus; (c) introducing said site specific nuclease and a DNA of interest into the maize plant cell; (d) allowing the DNA of interest to insert into the target maize genomic locus; and (e) selecting maize plant cells that comprise the DNA of interest inserted into the target maize genomic locus.

The site specific nuclease of the method described above may be introduced into the maize plant cell either as a polypeptide or as nucleic acid molecule, which is transcribed and/or translated in the plant cell to produce the site specific nuclease. The site specific nuclease may be transiently expressed in the plant cell. The site specific nuclease may not be expressed in the maize cell, and may only be present in the maize cell as an active nuclease. The site specific nuclease and the DNA of interest may be introduced into the cell simultaneously or not simultaneously.

In some embodiments of the methods of the invention, the site specific nuclease is a CRISPR-associated nuclease, a zinc finger nuclease, a TALEN, or a meganuclease, singly or in combination. In some embodiments of the methods of the invention, the site specific nuclease is a CRISPR-associated nuclease, such as Cas9 or Cpf1, and the method includes at least one additional nucleic acid molecule encoding a guide RNA, which is also introduced into the maize cell. The guide RNA may be a single guide RNA or a dual guide RNA. The additional nucleic acid molecule(s) may be DNA molecule(s) that can be expressed in the maize cell to produce the guide RNA, or it may be RNA molecule(s), the guide RNA itself, which is introduced into the maize cell.

The present invention further provides a method of producing a maize plant, plant part, or progeny thereof comprising a DNA of interest, such as a transgene, integrated into the genomic nuclease cleavage site in the maize genome, comprising regenerating a maize plant from the maize cell produced by the method described herein. Accordingly, the present invention provides a maize plant, plant part, or progeny thereof comprising the transgene integrated into the genomic nuclease cleavage site in the maize genome, produced by the method of this invention.

The present invention also provides a maize recombinant polynucleotide, wherein the recombinant polynucleotide comprises a nucleic acid sequence of at least 50 nucleotides, at least 60, 70, 80, 90, 100, 150, 200, 250, 300, 250, 400, 450, 500, 600, 700, 800, 900, 1000, 1500, 2000, 2500, 3000, 3500, 4000, 4500, 5000, 7500, 10000, 15,000 or at least 20,000 nucleotides, and has at least 70%, at least 75%, at least 80%, at least 85%, at least 90%, at least 93%, at least 95%, at least 96%, at least 97%, at least 98%, at least 99%, or 100% identity to at least 50 contiguous nucleotides, 60, 70, 80, 90, 100, 150, 200, 250, 300, 250, 400, 450, 500, 600, 700, 800, 900, 1000, 1500, 2000, 2500, 2750, 2900, or at least 3000 contiguous nucleotides of SEQ ID NO: 1-71 or a complement thereof, and wherein the recombinant polynucleotide further comprises a DNA of interest, wherein the DNA of interest is inserted into the nucleic acid sequence to produce said recombinant polynucleotide.

In some embodiments, the recombinant polynucleotide comprises a DNA of interest which is a transgene. In some embodiments, the DNA of interest comprises at least one gene of interest. In some embodiments, the DNA of interest comprises at least one expression cassette. In some embodiments, the DNA of interest comprises two or more expression cassettes. In some embodiments, the DNA of interest does not encode a polypeptide. In some embodiments, the DNA of interest comprises regulatory sequences.

The present invention also provides a maize plant, plant part, or plant cell comprising the recombinant polynucleotide described above.

BRIEF DESCRIPTION OF THE SEQUENCES IN THE SEQUENCE LISTING

The nucleic acid sequences listed in the accompanying sequence listing are shown using standard letter abbreviations for nucleotide bases, as defined in 37 C.F.R. § 1.822. The nucleic acid and amino acid sequences listed define molecules (i.e., polynucleotides and polypeptides, respectively) having the nucleotide and amino acid monomers arranged in the manner described. The nucleic acid and amino acid sequences listed also each define a genus of polynucleotides or polypeptides that comprise the nucleotide and amino acid monomers arranged in the manner described.

Only one strand of each nucleic acid sequence is shown, but the complementary strand is understood as included by any reference to the displayed strand. As the complement and reverse complement of a primary nucleic acid sequence are necessarily disclosed by the primary sequence, the complementary sequence and reverse complementary sequence reference to the nucleic acid sequence, unless it is explicitly stated to be otherwise (or it is clear to be otherwise from the context in which the sequence appears). Furthermore, as it is understood in the art that the nucleotide sequence of an RNA strand is determined by the sequence of the DNA from which it was transcribed (but for the substitution of uracil (U) nucleobases for thymine (T)), an RNA sequence is included by any reference to the DNA sequence encoding it. In the accompanying sequence listing:

SEQ ID NOs: 1 to 61 are nucleotide sequences of identified safe harbor sites, ideal for targeted integration, within the genome of the maize elite inbred line AX5707.

SEQ ID NOs: 62 to 71 are nucleotide sequences of identified safe harbor sites, ideal for targeted integration, within the genome of the maize variety B73.

SEQ ID NOs: 72 to 81 are nucleotide sequences of target maize genomic loci for targeted insertion of a DNA of interest using the CRISPR-Cas9 system SEQ ID NOs: 82 to 91 are nucleotide sequences of maize genomic fragments from the elite inbred line AX5707 which can be used as homologous arms for recombination into a safe harbor site.

SEQ ID NOs: 92 to 105 are primers useful to the invention.

DETAILED DESCRIPTION OF THE INVENTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

As used in the description of the embodiments of the invention and the appended claims, the singular forms “a,” “an,” and “the” are intended to include the plural forms as well, unless the context clearly indicates otherwise.

As used herein, “and/or” refers to and encompasses any and all possible combinations of one or more of the associated listed items.

The term “about,” as used herein when referring to a measurable value such as an amount of a compound, dose, time, temperature, and the like, is meant to encompass variations of 20%, 10%, 5%, 1%, 0.5%, or even 0.1% of the specified amount.

The terms “comprise,” “comprises” and/or “comprising,” when used in this specification, specify the presence of stated features, integers, steps, operations, elements, and/or components, but do not preclude the presence or addition of one or more other features, integers, steps, operations, elements, components, and/or groups thereof.

As used herein, the transitional phrase “consisting essentially of” means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

The following definitions and methods are provided to better define the present invention and to guide those of ordinary skill in the art in the practice of the present invention. Unless otherwise noted, terms used herein are to be understood according to conventional usage by those of ordinary skill in the relevant art. Definitions of common terms in molecular biology may also be found in Rieger et al., *Glossary of Genetics: Classical and Molecular,* 5th edition, Springer-Verlag: New York, 1994.

The terms "nucleotide sequence" "nucleic acid," "nucleic acid sequence," "nucleic acid molecule," "oligonucleotide" and "polynucleotide" are used interchangeably herein to refer to a heteropolymer of nucleotides and encompass both RNA and DNA, including cDNA, genomic DNA, mRNA, synthetic (e.g., chemically synthesized) DNA or RNA and chimeras of RNA and DNA. The term nucleic acid molecule refers to a chain of nucleotides without regard to length of the chain. The nucleotides contain a sugar, phosphate and a base which is either a purine or pyrimidine. A nucleic acid molecule can be double-stranded or single-stranded. Where single-stranded, the nucleic acid molecule can be a sense strand or an antisense strand. A nucleic acid molecule can be synthesized using oligonucleotide analogs or derivatives (e.g., inosine or phosphorothioate nucleotides). Such oligonucleotides can be used, for example, to prepare nucleic acid molecules that have altered base-pairing abilities or increased resistance to nucleases. Nucleic acid sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. A "genome" is the entire body of genetic material contained in each cell of an organism. Unless otherwise indicated, a particular nucleic acid sequence of this invention also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid molecule is used interchangeably with gene, cDNA, and mRNA encoded by a gene.

The term "derived from" in the context of a molecule refers to a molecule isolated or made using a parent molecule or information from that parent molecule. For example, a Cas9 single mutant nickase and a Cas9 double mutant null-nuclease are derived from a wild-type Cas9 protein.

A "coding sequence" is a nucleic acid sequence that is transcribed into RNA such as mRNA, rRNA, tRNA, snRNA, sense RNA or antisense RNA. In some embodiments, the RNA is then translated in an organism to produce a protein.

By the term "express" or "expression" of a polynucleotide coding sequence, it is meant that the sequence is transcribed, and optionally translated.

"Expression cassette" as used herein means a nucleic acid molecule capable of directing expression of a particular nucleotide sequence in an appropriate host cell, comprising a promoter operably linked to the nucleotide sequence of interest, typically a coding region, which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions). In some embodiments, a gene refers to only the coding region. A gene may be "isolated" by which is meant a nucleic acid molecule that is substantially or essentially free from components normally found in association with the nucleic acid molecule in its natural state. Such components include other cellular material, culture medium from recombinant production, and/or various chemicals used in chemically synthesizing the nucleic acid molecule.

The term "native gene" refers to a gene as found in nature. The term "chimeric gene" refers to any gene that contains 1) DNA sequences, including regulatory and coding sequences that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Promoter" refers to a nucleotide sequence, usually upstream (5') to its coding sequence, which controls the expression of the coding sequence by providing the recognition for RNA polymerase and other factors required for proper transcription. "Promoter regulatory sequences" consist of proximal and more distal upstream elements. Promoter regulatory sequences influence the transcription, RNA processing or stability, or translation of the associated coding sequence. Regulatory sequences include enhancers, promoters, untranslated leader sequences, introns, and polyadenylation signal sequences. They include natural and synthetic sequences as well as sequences that may be a combination of synthetic and natural sequences. An "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. The meaning of the term "promoter" includes "promoter regulatory sequences."

"Intron" refers to an intervening section of DNA which occurs almost exclusively within a eukaryotic gene, but which is not translated to amino acid sequences in the gene product. The introns are removed from the pre-mature mRNA through a process called splicing, which leaves the exons untouched, to form an mRNA. For purposes of the present invention, the definition of the term "intron" includes modifications to the nucleotide sequence of an intron derived from a target gene, provided the modified intron does not significantly reduce the activity of its associated 5' regulatory sequence.

"Exon" refers to a section of DNA which carries the coding sequence for a protein or part of it. Exons are separated by intervening, non-coding sequences (introns). For purposes of the present invention, the definition of the term "exon" includes modifications to the nucleotide sequence of an exon derived from a target gene, provided the modified exon does not significantly reduce the activity of its associated 5' regulatory sequence.

A "transgene" refers to a nucleic acid molecule that has been introduced into the genome by transformation and is stably maintained. A transgene may comprise at least one expression cassette, typically comprises at least two expression cassettes, and may comprise ten or more expression cassettes. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but one that is introduced into the organism by gene transfer.

As used herein the term transgenic "event" refers to a recombinant plant produced by transformation and regeneration of a single plant cell with heterologous DNA, for example, an expression cassette that includes one or more genes of interest (e.g., transgenes). The term "event" refers to the original transformant and/or progeny of the transformant that include the heterologous DNA. The term "event" also refers to progeny produced by a sexual outcross between the transformant and another line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. For example, "event MIR604," "MIR604" or "MIR604 event" as used herein, means the original MIR604 transformant and/or progeny of the MIR604 transformant (U.S. Pat. Nos. 7,361,813, 7,897,748, 8,354,519, and 8,884,102, incorporated by references herein).

As used herein, "heterologous" refers to a nucleic acid molecule or nucleotide sequence not naturally associated with a host cell into which it is introduced, that either originates from another species or is from the same species or organism but is modified from either its original form or the form primarily expressed in the cell, including non-naturally occurring multiple copies of a naturally occurring nucleic acid sequence. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g., present in a different copy number, and/or under the control of different regulatory sequences than that found in the native state of the nucleic acid molecule. A nucleic acid sequence can also be heterologous to other nucleic acid sequences with which it may be associated, for example in a nucleic acid construct, such as e.g., an expression vector. As one nonlimiting example, a promoter may be present in a nucleic acid construct in combination with one or more regulatory element and/or coding sequences that do not naturally occur in association with that particular promoter, i.e., they are heterologous to the promoter.

An "isolated" nucleic acid molecule or nucleotide sequence or an "isolated" polypeptide is a nucleic acid molecule, nucleotide sequence or polypeptide that, by the hand of man, exists apart from its native environment and/or has a function that is different, modified, modulated and/or altered as compared to its function in its native environment and is therefore not a product of nature. An isolated nucleic acid molecule or isolated polypeptide may exist in a purified form or may exist in a non-native environment such as, for example, a recombinant host cell. Thus, for example, with respect to polynucleotides, the term isolated means that it is separated from the chromosome and/or cell in which it naturally occurs. A polynucleotide is also isolated if it is separated from the chromosome and/or cell in which it naturally occurs and is then inserted into a genetic context, a chromosome, a chromosome location, and/or a cell in which it does not naturally occur. The recombinant nucleic acid sequence molecules and nucleotide sequences of the invention can be considered to be "isolated" as defined above.

Thus, an "isolated nucleic acid molecule" or "isolated nucleotide sequence" is a nucleic acid molecule or nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid sequence that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid sequence that is part of a hybrid nucleic acid molecule encoding an additional polypeptide or peptide sequence. An "isolated nucleic acid molecule" or "isolated nucleotide sequence" can also include a nucleotide sequence derived from and inserted into the same natural, original cell type, but which is present in a non-natural state, e.g., present in a different copy number, and/or under the control of different regulatory sequences than that found in the native state of the nucleic acid molecule.

The term "isolated" can further refer to a nucleic acid molecule, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not necessarily mean that the preparation is technically pure (homogeneous), but it is sufficiently pure to provide the polypeptide or nucleic acid in a form in which it can be used for the intended purpose.

In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

"Wild-type" nucleotide sequence or amino acid sequence refers to a naturally occurring ("native") or endogenous nucleotide sequence or amino acid sequence. Thus, for example, a "wild-type mRNA" is an mRNA that is naturally occurring in or endogenous to the organism.

As used herein, the phrases "operably linked," "operatively linked," "operatively associated" or "in operative association" and the like, mean that elements of a nucleic acid construct such as an expression cassette or nucleic acid molecule are configured so as to perform their usual function. Thus, regulatory or control sequences (e.g., promoters) operatively associated with a nucleotide sequence are capable of effecting expression of the nucleotide sequence. For example, a promoter is operably linked with a coding sequence or functional RNA when it is capable of affecting the expression of that coding sequence or functional RNA (i.e., the coding sequence or functional RNA is under the transcriptional control of the promoter). Coding sequences in sense or antisense orientation can be operably-linked to regulatory sequences. The control sequences need not be contiguous with the nucleotide sequence of interest, as long as they function to direct the expression thereof. Thus, for example, intervening untranslated, yet transcribed, sequences can be present between a promoter and a coding sequence, and the promoter sequence can still be considered "operably linked" to the coding sequence.

"Primers" as used herein are isolated nucleic acids that are annealed to a complementary target DNA strand by nucleic acid hybridization to form a hybrid between the primer and the target DNA strand, then extended along the target DNA strand by a polymerase, such as DNA polymerase. Primer pairs or sets can be used for amplification of a nucleic acid molecule, for example, by the polymerase chain reaction (PCR) or other nucleic-acid amplification methods.

A "probe" is an isolated nucleic acid molecule that is complementary to a portion of a target nucleic acid molecule and is typically used to detect and/or quantify the target nucleic acid molecule. Thus, in some embodiments, a probe can be an isolated nucleic acid molecule to which is attached a detectable moiety or reporter molecule, such as a radioactive isotope, ligand, chemiluminescent agent, fluorescence agent or enzyme. Probes according to the present invention can include not only deoxyribonucleic or ribonucleic acids but also polyamides and other probe materials that bind specifically to a target nucleic acid sequence and can be used to detect the presence of and/or quantify the amount of, that target nucleic acid sequence.

A TaqMan probe is designed such that it anneals within a DNA region amplified by a specific set of primers. As the Taq polymerase extends the primer and synthesizes the nascent strand from a single-strand template from 3' to 5' of the complementary strand, the 5' to 3' exonuclease of the polymerase extends the nascent strand through the probe and consequently degrades the probe that has annealed to the template. Degradation of the probe releases the fluorophore from it and breaks the close proximity to the quencher, thus relieving the quenching effect and allowing fluorescence of the fluorophore. Hence, fluorescence detected in the quantitative PCR thermal cycler is directly proportional to the fluorophore released and the amount of DNA template present in the PCR.

Primers and probes are generally between 5 and 100 nucleotides or more in length. In some embodiments, primers and probes can be at least 20 nucleotides or more in length, or at least 25 nucleotides or more, or at least 30 nucleotides or more in length. Such primers and probes hybridize specifically to a target sequence under optimum hybridization conditions as are known in the art. Primers and probes according to the present invention may have complete sequence complementarity with the target sequence, although probes differing from the target sequence and which retain the ability to hybridize to target sequences may be designed by conventional methods according to the invention.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

The polymerase chain reaction (PCR) is a technique for "amplifying" a particular piece of DNA. In order to perform PCR, at least a portion of the nucleotide sequence of the DNA molecule to be replicated must be known. In general, primers or short oligonucleotides are used that are complementary (e.g., substantially complementary or fully complementary) to the nucleotide sequence at the 3' end of each strand of the DNA to be amplified (known sequence). The DNA sample is heated to separate its strands and is mixed with the primers. The primers hybridize to their complementary sequences in the DNA sample. Synthesis begins (5' to 3' direction) using the original DNA strand as the template. The reaction mixture must contain all four deoxynucleotide triphosphates (dATP, dCTP, dGTP, dTTP) and a DNA polymerase. Polymerization continues until each newly-synthesized strand has proceeded far enough to contain the sequence recognized by the other primer. Once this occurs, two DNA molecules are created that are identical to the original molecule. These two molecules are heated to separate their strands and the process is repeated. Each cycle doubles the number of DNA molecules. Using automated equipment, each cycle of replication can be completed in less than 5 minutes. After 30 cycles, what began as a single molecule of DNA has been amplified into more than a billion copies ($2^{30}=1.02\times10^9$).

The oligonucleotides of an oligonucleotide primer pair are complementary to DNA sequences located on opposite DNA strands and flanking the region to be amplified. The annealed primers hybridize to the newly synthesized DNA strands. The first amplification cycle will result in two new DNA strands whose 5' end is fixed by the position of the oligonucleotide primer but whose 3' end is variable ('ragged' 3' ends). The two new strands can serve in turn as templates for synthesis of complementary strands of the desired length (the 5' ends are defined by the primer and the 3' ends are fixed because synthesis cannot proceed past the terminus of the opposing primer). After a few cycles, the desired fixed length product begins to predominate.

"Detection kit" as used herein refers to a kit used to detect target DNA from the events of interest in a sample comprising nucleic acid probes and primers of the present invention, which will be processed specifically under optimum conditions to a target DNA sequence, and other materials necessary to enable nucleic acid hybridization and/or amplification methods.

As used herein, the terms "transformed" and "transgenic" refer to any plant, plant cell, callus, plant tissue, or plant part that contains all or part of at least one recombinant (e.g., heterologous) polynucleotide. In some embodiments, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

The term "plant part," as used herein, includes but is not limited to embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell of the present invention can be in the form of an isolated single cell or can be a cultured cell or can be a part of a higher-organized unit such as, for example, a plant tissue or a plant organ.

The term "transformation" as used herein refers to the transfer of a nucleic acid molecule into the genome of a host cell, resulting in genetically stable inheritance. In some embodiments, the introduction into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of nucleic acid into the plant, plant part and/or cell thereof, or any combination thereof.

Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in Methods in *Plant Molecular Biology and Biotechnology,* Glick, B. R. and Thompson, J. E., Eds. (CRC Press, Inc., Boca Raton, 1993), pages 67-88) and Rakowoczy-Trojanowska (*Cell Mol Biol Lett* 7:849-858 (2002)).

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. 1993, Plant Cell 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hofgen and Willmitzer 1988, *Nucleic Acids Res* 16:9877).

Transformation of a plant by recombinant *Agrobacterium* usually involves co-cultivation of the *Agrobacterium* with explants from the plant and follows methods well known in the art. Transformed tissue is typically regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacteria or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

The term "introducing" or "introduce" in the context of a plant cell, plant and/or plant part means contacting a nucleic acid molecule with the plant, plant part, and/or plant cell in such a manner that the nucleic acid molecule gains access to the interior of the plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol. Thus, the term "transformation" as used herein refers to the introduction of a heterologous nucleic acid into a cell. Transformation of a cell may be stable or transient. Thus, a transgenic plant cell, plant and/or plant part of the invention can be stably transformed or transiently transformed.

As used herein, "stably introducing," "stably introduced," "stable transformation" or "stably transformed" in the context of a polynucleotide introduced into a cell, means that the introduced polynucleotide is stably integrated into the genome of the cell, and thus the cell is stably transformed with the polynucleotide. As such, the integrated polynucleotide is capable of being inherited by the progeny thereof, more particularly, by the progeny of multiple successive generations. "Genome" as used herein includes the nuclear and/or plastid genome, and therefore includes integration of a polynucleotide into, for example, the chloroplast genome. Stable transformation as used herein can also refer to a polynucleotide that is maintained extrachromasomally, for example, as a minichromosome.

Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

"Primary transformant" and "T0 generation" refer to transgenic plants that are of the same genetic generation as the tissue that was initially transformed (i.e., not having gone through meiosis and fertilization since transformation). "Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

The "transformation and regeneration process" refers to the process of stably introducing a transgene into a plant cell and regenerating a plant from the transgenic plant cell. As used herein, transformation and regeneration includes the selection process, whereby a transgene comprises a selectable marker and the transformed cell has incorporated and expressed the transgene, such that the transformed cell will survive and developmentally flourish in the presence of the selection agent. "Regeneration" refers to growing a whole plant from a plant cell, a group of plant cells, or a plant piece such as from a protoplast, callus, or tissue part. Regeneration methods from a transformed plant cell, for example a transformed maize cell, are well-known in the art.

"Transient transformation" in the context of a polynucleotide means that a polynucleotide is introduced into the cell and does not integrate into the genome of the cell.

Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism (e.g., a plant). Stable transformation of a cell can be detected by, for example, a Northern blot hybridization assay of RNA of the cell with nucleic acid sequences which specifically hybridize with a nucleotide sequence of a nucleic acid molecule introduced into a plant or other organism. Stable transformation of a cell can also be detected by, e.g., a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods. Transformation can also be detected by direct sequencing and/or hybridization protocols well known in the art.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," in the context of two nucleic acid molecules, nucleotide sequences or protein sequences, refers to two or more sequences or subsequences that have at least about 70%, least about 75%, at least about 80%, least about 85%, at least about 90%, at least about 95%, at least about 96%, at least about 97%, at least about 98%, or at least about 99% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 50 residues to about 150 residues in length. Thus, in some embodiments of this invention, the substantial identity exists over a region of the sequences that is at least about 50, about 60, about 70, about 80, about 90, about 100, about 110, about 120, about 130, about 140, about 150, or more residues in length. In some particular embodiments, the sequences are substantially identical over at least about 150 residues. In a further embodiment, the sequences are substantially identical over the entire length of the coding regions. Furthermore, in representative embodiments, substantially identical nucleotide or protein sequences perform substantially the same function (e.g., conferring increased resistance to a nematode plant parasite, reducing the growth of a nematode plant parasite, reducing cyst development).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially identical when the two sequences hybridize to each other under stringent conditions. In some representative embodiments, two nucleotide sequences considered to be substantially identical hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the present invention. In one embodiment, a reference nucleotide sequence hybridizes to the "test" nucleotide sequence in 7% sodium dodecyl sulfate (SDS), 0.5 M $NaPO_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M $NaPO_4$, 1 mM EDTA at 50° C. with washing in 1×SSC, 0.1% SDS at 50° C. or in 7% sodium dodecyl sulfate (SDS), 0.5 M $NaPO_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M $NaPO_4$, 1 mM EDTA at 50° C. with washing in 0.1×SSC, 0.1% SDS at 50° C., or in 7% sodium dodecyl sulfate (SDS), 0.5 M $NaPO_4$, 1 mM EDTA at 50° C. with washing in 0.1×SSC, 0.1% SDS at 65° C.

In the current state of the art, introducing a DNA of interest into a maize cell is typically done using *Agrobacterium*-mediated transformation or biolistic bombardment. These methods rely on the random insertion of the DNA of interest, such as a transgene, into the maize genome. The expression of foreign genes in plants can be influenced by their chromosomal position, for example due to chromatin structure and/or the proximity of transcriptional regulation elements close to the integration site (See for example, Weising et al., 1988, "Foreign Genes in Plants," Ann. Rev. Genet. 22:421-477). A high-quality transgenic event is preferred to not be in a promoter or gene region of the genome. A high-quality transgenic event also must not have negative effects on the agronomic performance of the transgenic plant. Additionally, a high-quality transgenic event is the result of a single, intact, transgene insertion, with little or no transgene rearrangement, and without contamination by extraneous heterologous DNA, such as DNA from the backbone of a vector used during the transformation process. A high-quality transgenic event also is preferred to lack introduced ORFs, which potentially may be expressed in the transgenic plant.

It is common to produce hundreds of different events and screen those events for a single event that has desired molecular qualities and transgene expression levels and patterns for commercial purposes. The identified event which satisfies all criteria required for a high-quality event which may be used for commercial purposes is considered an elite event. The elite event is characterized by its exact genomic location, as it is that location which is responsible for the molecular qualities, transgene expression levels, and agronomic performance of the event. The effort required to identify an elite event is on the scale of a large research program. Therefore, there is a desire in the art for novel, more efficient methods of introducing a DNA of interest into a maize cell to produce a high-quality transgenic event.

The recent development of methods and compositions which make targeted genomic insertion relatively less labor intensive provide a critical piece for the technical solution for improved methods of insertion of heterologous nucleic acids into a genome of interest. The present invention includes ideal genomic locations, or loci, for methods for targeted genomic insertion. Successful targeted insertion into any one of these genomic loci can produce a high-quality transgenic event.

Ideal target sites for genomic modifications, in particular for targeted insertion of a DNA of interest into a maize genome, must satisfy a number of criteria. These desirable genomic target sites may also be referred to as "ideal genomic loci", "target genomic loci", "safe harbor sites", or "safe harbors", and refer to regions of contiguous nucleic acids in the genome that are the selected or preferred site for insertion of a nucleotide sequence of interest (for example, a donor sequence) into the genome. Based on the current knowledge of plant genome organization, gene structure and expression, DNA recombination, genome engineering and GM product regulatory requirements, the following artificially defined criteria were used to identify ideal genomic loci that are suitable for targeted integration and stable expression: (1) regions that contain mostly unique sequences and may be suitable for targeted integration mediated by homologous recombination; (2) regions that are not part of a known functional gene, including those encoding for miRNAs; ideally, these regions should be at least 2 Kb upstream of any known open reading frame or 1 Kb downstream from the 3'-untranslated region (3'-UTR) of a gene, so that integration of a DNA of interest may not interrupt endogenous gene sequences or affect function of neighboring endogenous genes; (3) regions that are not close to heterochromatic regions with highly repetitive sequences such as pericentromeric regions that may result in unstable expression of transgenes or potential silencing of inserted transgenes; (4) regions that do not contain known cis-acting elements such as enhancers or repressors so that transgene expression pattern and level is not altered unexpectedly when inserted; (5) regions that have empirical data showing good transgene expression, if possible. An example of a target maize genomic locus may comprise a nucleic acid sequence of at least 10 nucleotides, at least 20, 25, 30, 40, 50, 60, 70, 75, 80, 90, 100, 150, 200, 250, 300, 250, 400, 450, 500, 600, 700, 800, 900, 1000, 1500, 2000, 2500, 3000, 3500, 4000, 4500, or at least 5000 nucleotides, and have at least 70%, at least 75%, at least 80%, at least 85%, at least 90%, at least 93%, at least 95%, at least 96%, at least 97%, at least 98%, at least 99%, or 100% identity to at least 10 nucleotides, at least 20, 25, 30, 40, 50, 60, 70, 75, 80, 90, 100, 150, 200, 250, 300, 250, 400, 450, 500, 600, 700, 800, 900, 1000, 1500, 2000, 2500, 2750, 2900, or at least 3000 nucleotides of any one of SEQ ID NO: 1-71 or a complement thereof.

Targeting insertion of a DNA of interest into safe harbors identified by this criteria is likely to result in a transgenic plant which has minimal issues regarding stable expression levels. Targeting the DNA of interest to a safe harbor also eliminates significant screening required to identify events produced by random genomic insertion which satisfy the "safe harbor" criteria. Additionally, the identification of safe harbor sites which are highly conserved in more than one maize variety indicates that the safe harbor in one maize variety is likely to be a safe harbor in a different maize variety. This is important for introgression of the DNA of interest into multiple varieties for commercial agricultural use.

As used herein a "DNA of interest", "nucleic acid of interest", or "nucleotide sequence of interest", is defined as a nucleic acid/DNA sequence that has been selected for site directed, targeted insertion into the maize genome. A nucleic acid of interest can be of any length, for example between 2 and 50,000 nucleotides in length (or any integer value there between or there above), preferably between about 1,000 and 5,000 nucleotides in length (or any integer value there between). A DNA of interest may comprise one or more gene expression cassettes that further comprise actively transcribed and/or translated gene sequences. Conversely, the DNA of interest may comprise a polynucleotide sequence which does not comprise a functional gene expression cassette or an entire gene (e.g., may simply comprise regulatory sequences such as a promoter), or may not contain any identifiable gene expression elements or any actively transcribed gene sequence. The DNA of interest may optionally contain an analytical domain, such as a domain that may contain specifically designed restriction enzyme sites, zinc finger binding sites, engineered landing pads, or engineered transgene integration platforms. Upon insertion of the nucleic acid of interest into the maize genome, the inserted sequences may be referred to, for example, as the "inserted DNA of interest". Further, the nucleic acid of interest can be DNA or RNA, can be linear or circular, and can be single-stranded or double-stranded. It can be delivered to the cell as naked nucleic acid, as a complex with one or more delivery agents (e.g., liposomes, poloxamers, T-strand encapsulated with proteins, a Feldan Shuttle (U.S. Patent Publication No. 20160298078, herein incorporated by reference) etc.,) or contained in a bacterial or viral delivery vehicle, such as, for example, *Agrobacterium tumefaciens* or an adenovirus.

A DNA of interest may further comprise a "gene of interest". "Gene of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

A "donor", "donor molecule", or "donor sequence" as used herein comprises a DNA of interest. The donor molecule may further comprise homologous arms or other nucleic acid sequences useful for recombination of the nucleic acid of interest into the target site of the host genome. The donor sequence may comprise one or more transgenes, expression cassettes, or other nucleotide sequences of interest. A donor molecule may be single stranded, partially double-stranded, or double-stranded. The donor molecule may be a natural or a modified polynucleotide, a RNA-DNA chimera, or a DNA fragment, either single- or at least partially double-stranded, or a fully double-stranded DNA molecule, or a PGR amplified ssDNA or at least partially dsDNA fragment. In some embodiments, the donor DNA molecule is part of a circularized DNA molecule. A fully double-stranded donor DNA is advantageous since it might provide an increased stability, since dsDNA fragments are generally more resistant than ssDNA to nuclease degradation. In some embodiments, the donor polynucleotide molecule can comprise at least about 100, 150, 200, 250, 300, 250, 400, 450, 500, 600, 700, 800, 900, 1000, 1500, 2000, 2500, 3000, 3500, 4000, 4500, 5000, 7500, 10000, 15,000 or at least about 20,000 nucleotides, including any value within this range not explicitly recited herein. In some embodiments, the donor DNA molecule comprises a heterologous nucleic acid sequence. In some embodiments, the donor DNA molecule comprises at least one expression cassette. In some embodiments, the donor DNA molecule may comprise a transgene. In some embodiments, the donor DNA molecule comprises an allelic modification of a gene which is native to the target genome. The allelic modification may comprise at least one nucleotide insertion, at least one nucleotide deletion, and/or at least one nucleotide substitution. In some embodiments, the allelic modification may comprise an INDEL. In some embodiments, the donor DNA molecule comprises at least 50 nucleotides, at least 60, 70, 80, 90, 100, 150, 200, 250, 300, 250, 400, 450, 500, 600, 700, 800, 900, 1000, 1500, 2000, 2500, 3000, 3500, 4000, 4500, 5000, 7500, 10000, 15,000 or at least 20,000 nucleotides, which have at least 70%, at least 75%, at least 80%, at least 85%, at least 90%, at least 93%, at least 95%, at least 96%, at least 97%, at least 98%, at least 99%, or 100% identity to at least 50 contiguous nucleotides, 60, 70, 80, 90, 100, 150, 200, 250, 300, 250, 400, 450, 500, 600, 700, 800, 900, 1000, 1500, 2000, 2500, 2750, 2900, or at least 3000 contiguous nucleotides of SEQ ID NO: 1-71 or a complement thereof, and wherein the donor molecule further comprises a DNA of interest. In some embodiments, the donor DNA molecule comprises at least 100 contiguous nucleotides at least 90% identical to a genomic nucleic acid sequence, and optionally may further comprise a heterologous nucleic acid sequence such as a transgene.

A "homologous" nucleic acid sequence is a nucleic acid sequence naturally associated with a host cell into which it is introduced. A homologous nucleic acid sequence can also be a nucleic acid sequence that is naturally associated with other nucleic acid sequences that may be present, e.g., in a nucleic acid construct. As one nonlimiting example, a promoter may be present in a nucleic acid construct in combination with one or more regulatory elements and/or coding sequences that naturally occur in association with that particular promoter, i.e., they are homologous to the promoter.

In some instances "homologous" may be used to refer to the relationship of a first gene to a second gene by descent from a common ancestral DNA sequence. In such instances, the term "homolog" indicates a relationship between genes separated by the event of speciation (or an "ortholog") or to the relationship between genes separated by the event of genetic duplication (or a "paralog"). In other instances "homologous" may be used to refer to the level of sequence identity between one or more polynucleotide sequences, in such instances the one or more polynucleotide sequences do not necessarily descend from a common ancestral DNA sequence. Those with skill in the art are aware of the interchangeably of the term "homologous" and appreciate the proper application of the term.

Targeted genomic insertion methods of the invention require a site-directed nuclease and a nucleic acid molecule comprising the DNA of insertion as well as at least one homologous arm which is important for homologous recombination of the nucleic acid molecule into the target genomic locus. The target genomic locus comprises a nuclease cleavage site, which may be a targeted site for a site-directed nuclease.

A "nuclease cleavage site" or "genomic nuclease cleavage site" is a region of nucleotides that comprise a nuclease cleavage sequence that is recognized by a specific nuclease, which acts to cleave the nucleotide sequence of the DNA of the genomic nuclease cleavage site in one or both strands. Such cleavage by the nuclease enzyme initiates DNA repair mechanisms within the cell, which establishes an environment for homologous recombination to occur. In the methods herein wherein a first nucleic acid molecule comprises, for example, at least about 100 contiguous nucleotides having, for example, at least 90% identity with a target site in the genome of the cell, the first nucleic acid molecule may be integrated into the genome of the cell via homologous recombination, thereby integrating the one or more DNAs of interest into the genome of the cell.

The term "cleavage" or "cleaving" refers to breaking of the covalent phosphodiester linkage in the ribosylphosphodiester backbone of a polynucleotide. The terms "cleavage" or "cleaving" encompass both single-stranded breaks and double-stranded breaks. Double-stranded cleavage can occur as a result of two distinct single-stranded cleavage events. Cleavage can result in the production of either blunt ends or staggered ends.

The nuclease of the methods of the invention may be engineered to target the nucleic acid sequence of the genomic nuclease cleavage site. In some embodiments, the genomic nuclease cleavage site may be unique to the maize genome. In other embodiments, the genomic nuclease cleavage site may occur infrequently in the maize genome. "Infrequently" may be less than 500 occurrences, less than 400, 300, 200, 100, 90, 80, 70, 60, 50, 40, 30, 20, 10, 5, or less than 3 occurrences in the maize genome.

In some embodiments, the nuclease in the methods of the invention may be a site specific nuclease, such a meganuclease, a zinc finger nuclease, a TALEN, or a CRISPR-associated nuclease. In some embodiments, the meganuclease is a homing endonuclease, for example I-SceI or I-CreI. In some embodiments, the CRISPR-associated nuclease is a Cas9, Cpf1, or dCas9 ("dead" Cas9) or dCpf1 ("dead" Cpf1). For the "dead" CRISPR-associated nuclease, the nuclease activity of the RNA binding protein is inactivated.

In some embodiments, the site specific nuclease is a TALEN or a zinc finger nuclease. In some embodiments, the TALEN or zinc finger nuclease may be chimeric. The TALEN and/or zinc finger nuclease may bind to the maize genomic target site and cleave the maize genomic target site, where upon the DNA of interest integrates within or proximal to the maize genomic target site. In an embodiment, integration of the DNA of interest occurs within the maize genomic target site may result in rearrangements. In some embodiments, the rearrangements may comprise deletions, insertions, inversions, and repeats. In one embodiment, integration of the DNA of interest may occur proximal to the maize genomic target site. According to an aspect of the embodiment, the integration site of the DNA of interest is proximal to the target maize genomic locu, and may integrate within 1.5 Kb, 1.25 Kb, 1.0 Kb, 0.75 Kb, 0.5 Kb, 0.25 Kb, 0.15 Kb, 0.10 Kb, 50 bp, 25 bp, 10 bp, or within 5 bp to the maize genomic target site. Insertion within a genomic region proximal to the maize genomic target site is known in the art, see for example for zinc finger nucleases US Patent Pub No. 2010/0257 638 A1 (herein incorporated by reference in its entirety). As used herein, the terms "adjacent" or "adjacent to" with regard to one or more nucleotide sequences of this invention means immediately next to (e.g., with no intervening sequence) or separated by from about 1 base to about 1,000 bases (e.g., 1, 2, 3, 4, 5, 6, 7, 8, 9, 10, 15, 20, 30, 40, 50, 100, 200, 500, or 1,000 bases), including any values included within this range but not explicitly recited herein.

Zinc finger, meganuclease, and TALE DNA binding domains can be "engineered" to bind to a predetermined nucleotide sequence, for example via engineering (altering one or more amino acids) of the recognition helix region of a naturally occurring zinc finger. Similarly, TALENs and meganucleases can be "engineered" to bind to a predetermined nucleotide sequence, for example by engineering of the amino acids involved in DNA binding (for example, the repeat variable diresidue or RVD region in a TALEN). Therefore, engineered DNA binding proteins (zinc fingers, meganucleases, or TALENs) are proteins that are non-naturally occurring.

Non-limiting examples of methods for engineering DNA-binding proteins are design and selection. A designed DNA binding protein is a protein not occurring in nature whose design/composition results primarily from rational criteria. Rational criteria for design include application of substitution rules and computerized algorithms for processing information. Such rational criteria can be applied for the design of zinc fingers, TALENs, meganucleases, or CRISPR-associated nucleases. See, for example, U.S. Pat. Nos. 6,140,081, 6,453,242, 6,534,261; see also WO 98/53058; WO98/53059; WO 98/53060; WO 02/016536 and WO03/016496 and U.S. Publication Nos. 20110301073, 20110239315 and 20119145940. A "selected" zinc finger protein, CR1SPR-associated nuclease, meganuclease, or TALEN is a protein not found in nature whose production results primarily from an empirical process such as phage display, interaction trap or hybrid selection. See e.g., WO 96/06166; WO 98/53057;

WO 98/54311; WO00/27878; WO 01/60970 WO 01/88197 and WO 02/099084 and U.S. Publication Nos. 20110301073, 20110239315 and 20119145940.

In some embodiments, the DNA-binding domain is an engineered domain from a TAL effector derived from the plant pathogen *Xanthomonas* (see, Miller et al. (2011) Nature Biotechnology 29(2):143-8; Boch et al, (2009) Science 29 Oct. 2009 (10.1 126/science.117881) and Moscou and Bogdanove, (2009) Science 29 Oct. 2009 (10.1126/science.1178817; and U.S. Patent Publication Nos. 20110239315, 20110145940 and 20110301073).

In some embodiments, the DNA-binding domain may be associated with a cleavage (nuclease) domain. For example, homing endonucleases may be modified in their DNA-binding specificity while retaining nuclease function. In addition, zinc finger proteins may also be fused to a cleavage domain to form a zinc finger nuclease. The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) Nucleic Acids Res. 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). Non limiting examples of homing endonucleases and meganucleases include I-SceI, I-Ceul, PI-Pspl, PI-See, I-SceIV, I-Csml, I-PanI, I-SceII, I-PpoI, I-SceIII, I-CreI-TevI, I-TevII and I-TevIII. See also U.S. Pat. Nos. 5,420,032; 6,833,252; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263: 163-180; Argast et al. (1998) J. Mol. Biol. 280:345-353 and the New England Biolabs catalogue. One or more of these enzymes (or functional fragments thereof) can be used as a source of cleavage domains and cleavage half-domains.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites proximal to the recognition site and have separable binding and cleavage domains. For example, the Type IIS enzyme FokI catalyzes double stranded cleavage of DNA at 9 nucleotides from its recognition site on one strand and 13 nucleotides from its recognition site on the other. See, for example, U.S. Pat. Nos. 5,356,802, 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins may comprise the cleavage domain (or cleavage half domain) from at least one Type IIS restriction enzyme and one or more zinc finger binding domains, which may or may not be engineered. An exemplary Type IIS restriction enzyme, whose cleavage domain is separable from the binding domain, is FokI. This particular enzyme is active as a dimer (Bitinaite et al. (1998) Proc. Natl. Acad. Sci. USA 95: 10,570-10,575). Accordingly, for the purposes of the present disclosure, the portion of the FokI enzyme used in the disclosed fusion proteins is considered a cleavage half-domain. A cleavage domain or cleavage half-domain can be any portion of a protein that retains cleavage activity, or that retains the ability to multimerize (e.g., dimerize) to form a functional cleavage domain. Exemplary Type IIS restriction enzymes are described in International Publication WO 2007 1014275, incorporated by reference herein in its entirety. To enhance cleavage specificity, cleavage domains may also be modified. Non-limiting examples of modified cleavage half-domains are described in detail in WO 2007/014275, incorporated by reference in its entirety herein. In certain embodiments, the cleavage domain comprises an engineered cleavage half-domain (also referred to as dimerization domain mutants) that minimize or prevent homodimerization. Such embodiments are known to those of skill the art and described for example in U.S. Patent Publication Nos. 20050064474; 20060188987; 20070305346 and 20080131962, the disclosures of all of which are incorporated by reference in their entireties herein Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

The term "CRISPR-associated protein", "Cas protein", "CRIPSR-associated nuclease" or "Cas nuclease" refers to a wild type Cas protein, a fragment thereof, or a mutant or variant thereof. The term "Cas mutant" or "Cas variant" refers to a protein or polypeptide derivative of a wild type Cas protein, e.g., a protein having one or more point mutations, insertions, deletions, truncations, a fusion protein, or a combination thereof. In certain embodiments, the Cas mutant or Cas variant substantially retains the nuclease activity of the Cas protein, such as a Cas9 variant described herein which is operably linked to a nuclear localization signal (NLS) derived from a plant. In certain embodiments, the Cas nuclease is mutated such that one or both nuclease domains are inactive, such as, for example, a catalytically dead Cas9 referred to as dCas9, which is still able to target to a specific genomic location but has no endonuclease activity (Qi et al., 2013, Cell, 152: 1173-1183, hereby incorporated within). In some embodiments, the Cas nuclease is mutated so that it lacks some or all of the nuclease activity of its wild-type counterpart. The Cas protein may be Cas9, Cpf1 (Zetsche et al., 2015, Cell, 163: 759-771, hereby incorporated within) or another CRISPR-associated nuclease.

As used herein, the term "guide RNA" or "gRNA" generally refers to an RNA molecule (or a group of RNA molecules collectively) that can bind to a Cas protein and aid in targeting the Cas protein to a specific location within a target polynucleotide (e.g., a DNA). A guide RNA can comprise a crRNA segment and/or a tracrRNA. The present invention further provides a guide RNA of the invention comprising a tracrRNA, wherein the tracrRNA comprises a nucleic acid sequence that is capable of binding to protein. A guide RNA of the invention also encompasses an engineered chimeric single guide RNA (sgRNA), where the crRNA segment and the tracrRNA segment are located in the same RNA molecule. A "guide RNA" also encompasses, collectively, a group of two ("dual guide RNA") or more RNA molecules, where the crRNA segment and the tracrRNA segment are located in separate RNA molecules. As used herein, the term "crRNA" or "crRNA segment" refers to an RNA molecule or portion thereof that includes a polynucleotide targeting guide sequence, a stem sequence, and, optionally, a 5'-overhang sequence. As used herein, the term "tracrRNA" or "tracrRNA segment" refers to an RNA molecule or portion thereof that includes a protein-binding segment (e.g., the protein-binding segment is capable of interacting with a CRISPR-associated protein, such as a Cas9). The present invention further provides an engineered guide RNA comprising a chimeric crRNA segment comprising a guide RNA sequence capable of hybridizing to a genomic target sequence, a CRISPR repeat sequence and a bait RNA segment capable of hybridizing to a donor DNA molecule. In some embodiments, the guide RNA, either as a sgRNA or as two or more RNA molecules, does not contain a tracrRNA, as it is known in the art that some CRISPR-associated nucleases, such as Cpf1, do not require a tracrRNA for its RNA-mediated endonuclease activity (Qi et al., 2013).

The present invention also provides methods which include a nucleic acid molecule comprising a nucleic acid sequence encoding a guide RNA of the invention. The nucleic acid molecule may be a DNA or an RNA molecule. In some embodiments, the nucleic acid molecule is circularized. In other embodiments, the nucleic acid molecule is linear. In some embodiments, the nucleic acid molecule is single stranded, partially double-stranded, or double-stranded. In some embodiments, the nucleic acid molecule is complexed with at least one polypeptide. In some embodiments, the polypeptide is a carrier protein for mediating delivery of, for example, the guide RNA, a nuclease, and optionally a donor molecule. In some embodiments, the polypeptide is a Feldan Shuttle (U.S. Patent Publication No. 20160298078, herein incorporated by reference). The nucleic acid molecule may comprise an expression cassette capable of driving the expression of the guide RNA. The nucleic acid molecule may further comprise additional expression cassettes, capable of expressing, for example, a nuclease such as a CRISPR-associated nuclease.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the nucleotide sequence that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide. For HR-directed integration, the donor molecule contains at least 1, typically at least 2 regions of homology to the genome ("homology arms") of least 50-100 base pairs in length. See, e.g., U.S. Pat. No. 9,045,763. In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break for HR mediated integration or having no homology to the nucleotide sequence in the region of the break for NHEJ mediated integration, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another. In any of the methods described herein, additional zinc-finger proteins, meganucleases, CR1SPR-associated nucleases, or TALENs can be used for additional double-stranded cleavage of additional target sites within the cell.

Accordingly, the present invention provides a maize recombinant polynucleotide, wherein the recombinant polynucleotide comprises a nucleic acid sequence of at least 50 nucleotides, at least 60, 70, 80, 90, 100, 150, 200, 250, 300, 250, 400, 450, 500, 600, 700, 800, 900, 1000, 1500, 2000, 2500, 3000, 3500, 4000, 4500, 5000, 7500, 10000, 15,000 or at least 20,000 nucleotides, and has at least 70%, at least 75%, at least 80%, at least 85%, at least 90%, at least 93%, at least 95%, at least 96%, at least 97%, at least 98%, at least 99%, or 100% identity to at least 50 contiguous nucleotides, 60, 70, 80, 90, 100, 150, 200, 250, 300, 250, 400, 450, 500, 600, 700, 800, 900, 1000, 1500, 2000, 2500, 2750, 2900, or at least 3000 contiguous nucleotides of SEQ ID NO: 1-71 or a complement thereof, and wherein the recombinant polynucleotide further comprises a DNA of interest, wherein the DNA of interest is inserted into the nucleic acid sequence to produce said recombinant polynucleotide.

In further embodiments, the recombinant polynucleotide comprises a DNA of interest inserted proximal to a nuclease cleavage site within the recombinant polynucleotide.

In some embodiments, the recombinant polynucleotide comprises a DNA of interest which is a transgene. In some embodiments, the DNA of interest comprises at least one gene of interest. In some embodiments, the DNA of interest comprises at least one expression cassette. In some embodiments, the DNA of interest comprises two or more expression cassettes. In some embodiments, the DNA of interest does not encode a polypeptide. In some embodiments, the DNA of interest comprises regulatory sequences.

In some embodiments, the recombinant polynucleotide comprises a nucleic acid sequence of at least 50 nucleotides, at least 60, 70, 80, 90, 100, 150, 200, 250, 300, 250, 400, 450, 500, 600, 700, 800, 900, 1000, 1500, 2000, 2500, 3000, 3500, 4000, 4500, 5000, 7500, 10000, 15,000 or at least 20,000 nucleotides, and has at least 70%, at least 75%, at least 80%, at least 85%, at least 90%, at least 93%, at least 95%, at least 96%, at least 97%, at least 98%, at least 99%, or 100% identity to at least 50 contiguous nucleotides, at least 60, 70, 80, 90, 100, 150, 200, 250, 300, 250, 400, 450, 500, 600, 700, 800, 900, 1000, 1500, 2000, 2500, 2750, 2900, or at least 3000 contiguous nucleotides of SEQ ID NO: 1, 8, 9, 13, 21, 22, 23, 31, 37, 39, 40, 44, 46, 55, 56, 57, 62-71, or a complement thereof.

The present invention also provides a maize plant, plant part, or plant cell comprising the recombinant polynucleotide described above.

In another embodiment, the present invention provides a method of integrating a DNA of interest into a target maize genomic locus in a maize genome, wherein the target maize genomic locus comprises a nucleic acid sequence of at least 50, at least 60, at least 70, at least 80, at least 90, at least 100, at least 110, at least 120, at least 130, at least 140, at least 150, 200, 250, 300, 250, 400, 450, 500, 600, 700, 800, 900, 1000, 1500, 2000, 2500, 2750, 2900, or at least 3000 contiguous nucleotides having at least 70%, at least 75%, at least 80%, at least 85%, at least 90%, at least 93%, at least 95%, at least 96%, at least 97%, at least 98%, at least 99%, or 100% identity to at least 50 contiguous nucleotides, at least 60, at least 70, at least 80, at least 90, at least 100, at least 110, at least 120, at least 130, at least 140, at least 150, 200, 250, 300, 250, 400, 450, 500, 600, 700, 800, 900, 1000, 1500, 2000, 2500, 2750, 2900, or at least 3000 contiguous nucleotides of SEQ ID NO: 1 through SEQ ID NO: 71, or a complement thereof, comprising introducing into a maize cell: (a) a first nucleic acid molecule comprising at least 50, at least 60, at least 70, at least 80, at least 90, at least 100, at least 110, at least 120, at least 130, at least 140, or at least 150 contiguous nucleotides, wherein said contiguous nucleotides have at least 70%, at least 75%, at least 80%, at least 85%, at least 90%, at least 93%, at least 95%, at least 96%, at least 97%, at least 98%, at least 99%, or 100% identity to at least a 50, at least 60, at least 70, at least 80, at least 90, at least 100, at least 110, at least 120, at least 130, at least 140, or at least a 150 contiguous nucleotides of SEQ ID NO: 1 through SEQ ID NO: 71, or a complement thereof, and further comprising a DNA of interest; and (b) a second nucleic acid molecule comprising a nucleotide sequence encoding a nuclease for site-directed cleavage at a genomic nuclease cleavage site of, adjacent to, or proximal to the genomic nucleotide sequence of SEQ ID NO: 1 through SEQ ID NO: 71, or a complement thereof, that corresponds to the contiguous nucleotides of (a), under conditions wherein expression of the second nucleic acid molecule can occur to produce the nuclease and the nuclease can cleave the nucleotide sequence at the genomic nuclease cleavage site, whereby the DNA of interest is integrated at the genomic nuclease target cleavage site in the maize genome.

In some embodiments of the above method, the first nucleic acid molecule can comprise at least about 100, 150, 200, 250, 300, 250, 400, 450, 500, 600, 700, 800, 900, 1000, 1500, 2000, 2500, 3000, 3500, 4000, 4500, 5000, 7500, 10000, 15,000 or 20,000 nucleotides, including any value within this range not explicitly recited herein.

In some embodiments, the first nucleic acid molecule and the second nucleic acid molecule can be introduced into the maize cell by biolistic nucleic acid delivery, via an *Agrobacterium*, by co-transformation, and/or with a T-DNA vector in any combination and/or order.

In some embodiments, the first nucleic acid molecule and the second nucleic acid molecule can be present on a single nucleic acid construct and in some embodiments, the first nucleic acid molecule and the second nucleic acid molecule can be present on separate nucleic acid constructs.

In some embodiments, the first nucleic acid molecule and/or the second nucleic acid molecule can be transiently expressed in the maize cell. In some embodiments, the first nucleic acid molecule and/or the second nucleic acid molecule can be stably integrated into the maize genome of the maize cell.

In some embodiments of the methods of the invention, the first nucleic acid molecule is a donor molecule. In some embodiments, the DNA of interest comprises at least one expression cassette. In some embodiments, the DNA of interest comprises a transgene.

In another embodiment, the present invention provides a method of making a maize plant cell comprising a DNA of interest, said method comprising: (a) selecting a target maize genomic locus, wherein the target maize genomic locus comprises a nucleic acid sequence of at least 10, 20, 25, 30, 40, 50, 60, 70, 75, 80, 90, 100, 150, 200, 250, 300, 250, 400, 450, 500, 600, 700, 800, 900, 1000, 1500, 2000, 2500, or at least 3,000 contiguous nucleotides, and has at least 70%, at least 75%, at least 80%, at least 85%, at least 90%, at least 93%, at least 95%, at least 96%, at least 97%, at least 98%, at least 99%, or 100% identity to at least 10, 20, 25, 30, 40, 50, 60, 70, 75, 80, 90, 100, 150, 200, 250, 300, 250, 400, 450, 500, 600, 700, 800, 900, 1000, 1500, 2000, 2500, or at least 3,000 contiguous nucleotides of SEQ ID NO: 1-71 or a complement thereof; (b) selecting a site specific nuclease that specifically binds to and cleaves a genomic nuclease cleavage site within said target maize genomic locus; (c) introducing said site specific nuclease and a DNA of interest into the maize plant cell; (d) allowing the DNA of interest to insert into the target maize genomic locus; and (e) selecting maize plant cells that comprise the DNA of interest inserted into the target maize genomic locus.

The site specific nuclease of the method described above may be introduced into the maize plant cell either as a polypeptide or as nucleic acid molecule, which is transcribed and/or translated in the plant cell to produce the site specific nuclease. The site specific nuclease may be transiently expressed in the plant cell. The site specific nuclease may not be expressed in the maize cell, and may only be present in the maize cell as an active nuclease. The site specific nuclease and the DNA of interest may be introduced into the cell simultaneously or not simultaneously.

In some embodiments of the methods of the invention, the genomic nuclease cleavage site is within a target maize genomic locus which comprises a nucleic acid sequence of at least 10, 20, 25, 30, 40, 50, 60, 70, 75, 80, 90, 100, 150, 200, 250, 300, 250, 400, 450, 500, 600, 700, 800, 900, 1000, 1500, 2000, 2500, or at least 3,000 contiguous nucleotides, and has at least 70%, at least 75%, at least 80%, at least 85%, at least 90%, at least 93%, at least 95%, at least 96%, at least 97%, at least 98%, at least 99%, or 100% identity to at least 10, 20, 25, 30, 40, 50, 60, 70, 75, 80, 90, 100, 150, 200, 250, 300, 250, 400, 450, 500, 600, 700, 800, 900, 1000, 1500, 2000, 2500, or at least 3,000 contiguous nucleotides of SEQ ID NO: 1, 8, 9, 13, 21, 22, 23, 31, 37, 39, 40, 44, 46, 55, 56, 57, 62-71, or the complement thereof.

In some embodiments of the methods of the invention, the DNA of interest is inserted into the target maize genomic locus via homologous recombination. In other embodiments, the DNA of interest inserted into the target maize genomic locus via non-homologous end-joining. In some embodiments, the DNA of interest and/or the target maize genomic locus are modified during insertion of said DNA of interest into said target maize genomic locus.

In some embodiments of the methods of the invention, two or more DNAs of interest are inserted into two or more target maize genomic loci by any one of the methods described herein.

In some embodiments of the methods of the invention, the DNA of interest comprises at least one expression cassette. In some embodiments, the DNA of interest comprises a transgene. In some embodiments of the methods of the invention, the DNA of interest does not encode for a polypeptide. In some embodiments of the methods of the invention, the DNA of interest encodes for regulatory sequences.

In some embodiments of the methods of the invention, the site specific nuclease is a CRISPR-associated nuclease, a zinc finger nuclease, a TALEN, or a meganuclease, singly or in combination.

In some embodiments of the methods of the invention, the maize plant cell comprising the target maize genomic locus is transgenic, such that it contains a heterologous sequence in its genome prior to the practice of the method.

In some embodiments of the methods of the invention, the site specific nuclease is a CRISPR-associated nuclease, such as Cas9, and the method includes an additional nucleic acid molecule encoding a guide RNA, which is also introduced into the maize cell. The additional nucleic acid molecule may be a DNA molecule that can be expressed in the maize cell to produce the guide RNA, or it may be an RNA molecule, the guide RNA molecule itself, which is introduced into the maize cell.

In some embodiments, methods of integrating a DNA of interest into a target maize genomic locus comprise a nucleic acid molecule which is a donor molecule. The donor molecule may be a donor vector. The donor molecule may be part of the CRISPR-Cas nuclease system. The nucleic acid sequence of the donor molecule may comprise a DNA of interest and also one or more regions that share homology with the targeted genomic locus. Generally, the homologous region(s) of the donor molecule will have at least 50% sequence identity to a genomic sequence with which recombination is desired. In certain embodiments, the homologous region(s) of the nucleic acid of interest shares at least 70%, at least 75%, at least 80%, at least 85%, at least 90%, at least 95%, at least 96%, at least 97%, at least 98%, at least 99%, or 100% sequence identity with sequences located in the targeted genomic locus. However, any value between 1% and 100% sequence identity can be present, depending upon the length of the nucleic acid of interest. A DNA of interest can contain several, discontinuous regions of sequence sharing relatively high sequence identity to cellular chromatin. For example, for targeted insertion of sequences not normally present in a targeted genomic locus, the unique sequences which comprise the DNA of interest can be present in a donor nucleic acid molecule and flanked by regions of sequences that share a relatively high sequence identity to a sequence present in the targeted genomic locus.

In some embodiments, a donor nucleic acid molecule, which comprises a DNA of interest, is introduced into a host cell for targeted insertion into a safe harbor site in the genome, wherein the donor molecule also comprises homologous flanking sequences on one or both ends of the nucleic acid of interest. In such an embodiment, the homologous flanking sequences contain sufficient levels of sequence identity to a maize genomic sequence to support homologous recombination between it and the genomic sequence to which it bears homology. Approximately 25, 50, 100, 200, 500, 750, 1000, 1500, or 2000 nucleotides, with sequence identity of at least 70%, at least 75%, at least 80%, at least 85%, at least 90%, at least 95%, at least 96%, at least 97%, at least 98%, at least 99%, or 100%, between a donor and a genomic sequence will support homologous recombination there between.

In other embodiments of targeted recombination and/or replacement and/or alteration of genomic sequence at the safe harbor, the genomic sequence is altered by homologous recombination with the donor molecule. Such homologous recombination is stimulated by the presence of a double-stranded break in cellular chromatin, if sequences homologous to the region of the break are present. Double-strand breaks in cellular chromatin can also stimulate cellular mechanisms of non-homologous end-joining. In any of the methods described herein, the donor molecule can contain sequences that are homologous, but not identical, to genomic sequences in the safe harbor, thereby stimulating homologous recombination to insert a non-identical sequence in the safe harbor. Thus, in certain embodiments, portions of the donor molecule that are homologous to sequences in the safe harbor exhibit at least 70%, at least 75%, at least 80%, at least 85%, at least 90%, at least 95%, at least 96%, at least 97%, at least 98%, at least 99%, or 100% sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the safe harbor, such that new sequences are introduced into the safe harbor. In these instances, the non-homologous sequence is generally flanked by sequences of 50 to 2,000 base pairs (or any integral value there between) or any number of base pairs greater than 2,000, that are homologous or identical to sequences in the region of interest. In other embodiments, the donor sequence is non-homologous to the region of interest, and is inserted into the genome for example by non-homologous end-joining. In some embodiments, the sequence of the genomic safe harbor site and/or of the nucleic acid sequence of interest is altered by either the homologous recombination or the non-homologous end-joining. Such alterations may be, for example, the insertion and/or deletion of nucleic acids.

The donor molecule comprising the DNA of interest may be a linear or a circularized molecule. In some embodiments, the donor molecule is circularized and is preferably linearized in vivo by a nuclease, for example one or more of the same or different nucleases that are used to introduce the double-stranded break in the genomic safe harbor site. Synchronized cleavage of the chromosome and the donor molecule in the cell may limit donor DNA degradation (as compared to linearization of the donor molecule prior to introduction into the cell). The nuclease target sites used for linearization of the donor preferably do not disrupt the transgene(s) sequence(s). The transgene may be integrated into the genome in the direction expected by simple ligation of the nuclease overhangs (designated "forward" or "AB" orientation) or in the alternate direction (designated "reverse" or "BA" orientation). In certain embodiments, the transgene is integrated following accurate ligation of the donor and chromosome overhangs. In other embodiments, integration of the transgene in either the BA or AB orientation results in insertion and/or deletion of several nucleotides.

In some embodiments of the methods of the invention, the DNA of interest is integrated into the targeted genomic site of the host cell. In the case of multicellular species, such as maize, transgenic cells may be regenerated into maize callus, a maize plant part, or a maize plant. In some embodiments, the transgenic cell may be cultured to produce a transgenic plant, for example, comprising one or more DNA sequences of interest at one or more safe harbor sites in the genome of the transgenic plant.

The present invention further provides a method of producing a maize plant, plant part, or progeny thereof comprising a DNA of interest, such as a transgene, integrated into the genomic nuclease cleavage site in the maize genome, comprising regenerating a maize plant from the maize cell produced by the method described herein.

Accordingly, the present invention provides a maize plant, plant part, or progeny thereof comprising the transgene integrated into the genomic nuclease cleavage site in the maize genome, produced by the method of this invention.

In some embodiments of the methods described above, the mutation comprises at least one nucleotide substitution, the deletion of at least one nucleotide, or a combination of substitution, deletion, and/or insertion, such as for example an INDEL.

In some embodiments of the methods described above, the nuclease for site-directed cleavage is a non-engineered nuclease. In some embodiments, the nuclease is an engineered nuclease with programmable cleavage target specificity. In some embodiments, the nuclease is a Cas9.

The present invention additionally provides a method of producing a plant, plant part, or progeny thereof comprising a transgene introduced at a nuclease cleavage site in a genome of a plant cell and lacking integration of a heterologous nucleotide sequence encoding a nuclease for site-directed cleavage of a nucleotide sequence at the nuclease cleavage site in the genome of the plant cell, comprising: a) introducing into the plant cell a nucleic acid molecule comprising a heterologous nucleotide sequence encoding a nuclease for site-directed cleavage of the nucleotide sequence at the nuclease cleavage site in the genome of the plant cell under conditions wherein expression of the nucleic acid molecule occurs transiently to produce the nuclease and the nuclease can cleave the nucleotide sequence at the nuclease cleavage site in the genome of the plant cell, thereby introducing a mutation at the nuclease cleavage site in the genome of the plant cell without integration of the heterologous nucleotide sequence encoding the nuclease into the genome of the plant cell; and b) regenerating a plant, plant part, or progeny thereof from the plant cell of (a). The nuclease cleavage site described above is located within a target genomic locus, which comprises a nucleic acid sequence of at least 10, 20, 25, 30, 40, 50, 60, 70, 75, 80, 90, 100, 150, 200, 250, 300, 250, 400, 450, 500, 600, 700, 800, 900, 1000, 1500, 2000, 2500, or at least 3,000 contiguous nucleotides, and has at least 70%, at least 75%, at least 80%, at least 85%, at least 90%, at least 93%, at least 95%, at least 96%, at least 97%, at least 98%, at least 99%, or 100% identity to at least 10, 20, 25, 30, 40, 50, 60, 70, 75, 80, 90, 100, 150, 200, 250, 300, 250, 400, 450, 500, 600, 700, 800, 900, 1000, 1500, 2000, 2500, or at least 3,000 contiguous nucleotides of SEQ ID NO: 1-71 or a complement thereof. In another embodiment, the present invention provides for the plant cell produced by the method described above. In a further embodiment, the present invention provides for a plant or plant part regenerated or derived from the plant cell produced by the method described above.

In some embodiments of the method described above, the transgene may comprise at least one, at least two, at least three, at least four, at least five, at least six, at least seven, at least eight, at least nine, at least ten, or ten or more expression cassettes.

In some embodiments of the methods described above, a second nucleic acid molecule comprising a DNA of interest is also introduced into the plant cell. In some embodiments of the methods described above, the first nucleic acid molecule and the second nucleic acid molecule are introduced at the same time, for example by co-transformation, biolistic nucleic acid delivery, or *Agrobacterium*-mediated transformation. In some embodiments, the first nucleic acid molecule and the second nucleic acid molecule are separate molecules. In some embodiments, a single nucleic acid molecule or construct comprises the first nucleic acid molecule and the second nucleic acid molecule described above.

In some embodiments of the methods described above, the nuclease for site-directed cleavage is a non-engineered nuclease. In some embodiments, the nuclease is an engineered nuclease with programmable cleavage target specificity. In some embodiments, the nuclease is a meganuclease, a TALEN, a zinc finger nuclease, or a CRISPR-associated nuclease, such as Cas9.

The present invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the present invention.

Examples

Example 1: Identification of Candidate Safe Harbor Sites in the Maize Genome Syngenta elite inbred maize line AX5707 was sequenced and assembled using methods known in the art. The assembled reference genome was annotated using the computer software program MAKER (Cantarel et al. 2008, MAKER: An easy-to-use annotation pipeline designed for emerging model organism genomes. *Genuine Research.* 18(1):188-196. doi:10.1101/gr.6743907), AX5707 mRNA-SEQ data, and information on plant proteins publicly available from Genbank. Sequences intervals which met certain criteria were selected as potential safe harbors for targeted insertion of a DNA of interest. These criteria including: 1) they do not encode genes including predicted gene models, co-localize with mapped RNA-SEQ data or protein coding sequences; 2) they do not encode smRNAs; 3) they are not repeated in the reference genome; 4) they are ≥1,500 bps; 5) they are ≥2,000 bps away from the nearest identified features such as gene models. 61 sequence intervals were identified. (Table 1). The genomic start and stop positions are as identified on the AX5707 reference genome, referred to as MAIZE_JHAX_REG_5. These candidate safe harbor sites were identified as ideal locations in the maize genome for targeted insertion, and may also be referred to as target maize genomic loci for targeted insertion of a DNA of interest.

TABLE 1

Candidate safe harbor sequence intervals in the AX5707 genome

| Chromosome No. | Genome start position | Genome end position | Length (bp) | SEQ. ID. NO: |
|---|---|---|---|---|
| Chr_1 | 6,051,580 | 6,053,351 | 1,772 | 1 |
| Chr_1 | 9,302,205 | 9,300,245 | 1,961 | 2 |
| Chr_1 | 49,377,512 | 49,375,750 | 1,763 | 3 |
| Chr_1 | 230,909,826 | 230,911,851 | 2,026 | 4 |
| Chr_1 | 233,264,403 | 233,267,221 | 2,819 | 5 |
| Chr_1 | 240,799,470 | 240,801,585 | 2,116 | 6 |
| Chr_1 | 308,952,173 | 308,950,540 | 1,634 | 7 |
| Chr_1 | 325,437,387 | 325,434,968 | 2,420 | 8 |
| Chr_2 | 25,144,470 | 25,146,195 | 1,726 | 9 |
| Chr_2 | 75,055,711 | 75,053,789 | 1,923 | 10 |
| Chr_2 | 76,900,194 | 76,901,853 | 1,660 | 11 |
| Chr_3 | 12,722,668 | 12,724,219 | 1,552 | 12 |
| Chr_3 | 15,938,135 | 15,936,500 | 1,636 | 13 |
| Chr_3 | 58,267,137 | 58,265,554 | 1,584 | 14 |
| Chr_3 | 144,608,280 | 144,610,055 | 1,776 | 15 |

TABLE 1-continued

Candidate safe harbor sequence intervals in the AX5707 genome

| Chromosome No. | Genome start position | Genome end position | Length (bp) | SEQ. ID. NO: |
|---|---|---|---|---|
| Chr_3 | 168,663,077 | 168,661,053 | 2,025 | 16 |
| Chr_3 | 187,169,278 | 187,171,380 | 2,103 | 17 |
| Chr_3 | 192,200,564 | 192,199,030 | 1,535 | 18 |
| Chr_3 | 194,535,751 | 194,533,809 | 1,943 | 19 |
| Chr_3 | 199,586,759 | 199,588,327 | 1,569 | 20 |
| Chr_3 | 263,100,502 | 263,098,753 | 1,750 | 21 |
| Chr_4 | 11,109,020 | 11,107,079 | 1,942 | 22 |
| Chr_4 | 11,850,583 | 11,852,381 | 1,574 | 23 |
| Chr_4 | 28,740,222 | 28,741,822 | 1,601 | 24 |
| Chr_4 | 41,128,134 | 41,125,263 | 2,872 | 25 |
| Chr_4 | 122,196,154 | 122,198,795 | 2,642 | 26 |
| Chr_4 | 225,424,622 | 225,422,966 | 1,657 | 27 |
| Chr_4 | 241,199,476 | 241,201,387 | 1,912 | 28 |
| Chr_4 | 241,203,112 | 241,204,386 | 1,275 | 29 |
| Chr_4 | 260,439,892 | 260,441,993 | 2,102 | 30 |
| Chr_5 | 31,399,845 | 31,397,479 | 2,367 | 31 |
| Chr_5 | 52,271,003 | 52,269,062 | 1,942 | 32 |
| Chr_5 | 61,967,477 | 61,969,470 | 1,994 | 33 |
| Chr_5 | 106,828,555 | 106,826,658 | 1,898 | 34 |
| Chr_5 | 194,229,496 | 194,227,080 | 2,417 | 35 |
| Chr_5 | 227,918,248 | 227,916,660 | 1,589 | 36 |
| Chr_5 | 249,991,940 | 249,989,642 | 2,299 | 37 |
| Chr_5 | 254,507,410 | 254,510,012 | 2,603 | 38 |
| Chr_6 | 2,550,820 | 2,549,212 | 1,609 | 39 |
| Chr_6 | 5,357,797 | 5,356,004 | 1,794 | 40 |
| Chr_6 | 102,854,792 | 102,856,689 | 1,898 | 41 |
| Chr_6 | 125,539,340 | 125,536,747 | 2,594 | 42 |
| Chr_6 | 140,569,284 | 140,567,471 | 1,814 | 43 |
| Chr_6 | 172,684,264 | 172,686,334 | 2,071 | 44 |
| Chr_7 | 6,130,641 | 6,133,196 | 2,556 | 45 |
| Chr_7 | 22,848,628 | 22,850,204 | 1,577 | 46 |
| Chr_7 | 92,523,693 | 92,521,688 | 2,006 | 47 |
| Chr_7 | 123,048,334 | 123,046,540 | 1,795 | 48 |
| Chr_7 | 129,393,722 | 129,390,033 | 3,690 | 49 |
| Chr_7 | 143,964,001 | 143,965,742 | 1,742 | 50 |
| Chr_7 | 145,353,967 | 145,352,332 | 1,636 | 51 |
| Chr_7 | 154,264,096 | 154,267,032 | 2,937 | 52 |
| Chr_7 | 172,566,096 | 172,564,156 | 1,941 | 53 |
| Chr_7 | 179,903,048 | 179,901,489 | 1,560 | 54 |
| Chr_7 | 198,992,304 | 198,994,416 | 2,113 | 55 |
| Chr_8 | 30,777,043 | 30,778,622 | 1,580 | 56 |
| Chr_8 | 210,893,628 | 210,891,662 | 1,967 | 57 |
| Chr_9 | 90,581,099 | 90,582,704 | 1,606 | 58 |
| Chr_9 | 137,742,555 | 137,739,791 | 2,765 | 59 |
| Chr_10 | 18,312,696 | 18,314,420 | 1,725 | 60 |
| Chr_10 | 174,905,414 | 174,903,831 | 1,584 | 61 |

Example 2: Selection of Candidate Maize Genome Safe Harbor Sites for Targeted Insertion The above identified 61 AX5707 candidate safe harbor sequence intervals were blasted against the publicly available B73 genome (AGPv3/RefGen_v3; available at the maize genetics and genomics database website (Andorf et al., 2016. "MaizeGDB update: new tools, data and interface for the maize model organism database." Nucleic Acids Res, 44(d1): D1195-201). Only sequences shared between both B73 and AX5707 genomes with a minimum length of 1,500 bp were selected for further evaluation. Among them, only 1 or 2 of the best candidates from each chromosome were selected. As a result, 10 candidate safe harbor site sequences were selected for experimental validation of targeted insertion. Chromosome 9 and 10 did not have suitable sequence remaining as candidates. The potential safe harbors are described in Table 2. Table 2 indicates the genomic position of the safe harbor in both the AX5707 genome and the B73 genome. The B73 genomic locations are as found in the publicly available MAIZE_B73_REF_4 genome. These target maize genomic loci are particularly useful for targeted insertion of a DNA of interest, because each locus is present in the genome of more than one maize variety. Therefore, the target maize genomic locus is useful for targeted insertion of a DNA of interest into more than one variety of maize cell.

TABLE 2

Candidate safe harbor in AX5707 and B73 genomes

| Genome | Map | Safe harbor ID | Genome start position | Genome end position | Length (bp) | SEQ. ID. NO: |
|---|---|---|---|---|---|---|
| AX5707 | Chr_1 | SH_Chr1.1b | 325,437,387 | 325,434,968 | 2,420 | 8 |
| B73 | Chr_l | SH_Chrl.lb | 270,485,529 | 270,483,110 | 2,420 | 62 |
| AX5707 | Chr_2 | SH_Chr2.1t | 25,144,470 | 25,146,195 | 1,726 | 9 |
| B73 | Chr_2 | SH_Chr2.1t | 20,384,387 | 20,386,397 | 1715 | 63 |
| AX5707 | Chr_3 | SH_Chr3.1b | 263,100,502 | 263,098,753 | 1,750 | 21 |
| B73 | Chr_3 | SH_Chr3.1b | 218,255,241 | 218,253,476 | 1,766 | 64 |
| AX5707 | Chr_4 | SH_Chr4.1t | 11,850,583 | 11,852,381 | 1,574 | 23 |
| B73 | Chr_4 | SH_Chr4.1t | 11,050,139 | 11,051,738 | 1,600 | 65 |
| AX5707 | Chr_5 | SH_Chr5.1t | 31,399,845 | 31,397,479 | 2,367 | 31 |
| B73 | Chr_5 | SH_Chr5.1t | 26,056,598 | 26,054,232 | 2,367 | 66 |
| AX5707 | Chr_6 | SH_Chr6.1b | 172,684,264 | 172,686,334 | 2,071 | 44 |
| B73 | Chr_6 | SH_Chr6.1b | 152,128,279 | 152,130,349 | 2,071 | 67 |
| AX5707 | Chr_7 | SH_Chr7.1t | 22,848,628 | 22,850,204 | 1,577 | 46 |
| B73 | Chr_7 | SH_Chr7.1t | 20,083,153 | 20,084,729 | 1,577 | 68 |
| AX5707 | Chr_7 | SH_Chr7.2b | 198,992,304 | 198,994,416 | 2,113 | 55 |
| B73 | Chr_7 | SH_Chr7.2b | 172,546,393 | 172,548,490 | 2,098 | 69 |
| AX5707 | Chr_8 | SH_Chr8.1t | 30,777,043 | 30,778,622 | 1,580 | 56 |
| B73 | Chr_8 | SH_Chr8.1t | 25,491,600 | 25,493,179 | 1,580 | 70 |
| AX5707 | Chr_8 | SH_Chr8.2b | 210,893,628 | 210,891,662 | 1,967 | 57 |
| B73 | Chr_8 | SH_Chr8.2b | 178,200,769 | 178,198,798 | 1,972 | 71 |

Example 3: Construction of CRISPR-Cas9 Expression and Targeting Donor Vectors

The following example describes construction of vectors used for CRISPR-Cas mediated targeted insertion, using the CRISPR-associated site specific nuclease Cas9. It is well-known in the art that there are many different nuclease-mediated targeted insertion systems, including ZFNs, meganucleases, and TALENS. The examples disclosed here do not limit the invention to any particular system of targeted insertion.

To demonstrate that the selected candidate safe harbor sites can be used for targeted insertion, a 20-nucleotide target sequence, which is followed by a 5'-NGG PAM site, within each safe harbor site was chosen for designing a single guide RNA (sgRNA) to test Cas9-mediated cleavage and gene targeting (Table 3). Cas9 and sgRNA-mediated targeted insertion in maize cells have been previously described in the art (WO16106121, herein incorporated by reference). Similar Cas9 and sgRNA expression vector designs were used for testing candidate safe harbor sites here. Each Cas9-sgRNA expression vector (vector ID's shown in Table 3) comprises a coding sequence for a Cas9 nuclease, operably linked to a promoter at its 5' end and a terminator at its 3' end, and also comprises a coding sequence for a sgRNA comprising a target sequence which targets the Cas9 to a genomic nuclease cleavage site within the target maize genomic locus, also referred to as the safe harbor. The sgRNA is operably linked at its 5'end to a rice ubiquitin promoter and at its 3' end to a terminator. The sgRNA for each Cas9-sgRNA expression vector comprises a target sequence (SEQ ID NO: 72-81), as described in Table 3.

TABLE 3

Target sequences for CRISPR-Cas9 targeted insertion

| Safe harbor ID | Target sequence for Cas9-sgRNA vector design | Target sequence name | Target sequence SEQ. ID. NO. | Cas9-sgRNA vector ID | Cas9-sgRNA vector Alias |
|---|---|---|---|---|---|
| SHChr1.1b | 5'-AGCAC CGGTT GCTCG GACCG-3' | xZmSHChr1 | 72 | 23808 | SHChr1_Cas9 |
| SHChr2.1t | 5'-TACAG AAACG CGGAG AGACT-3' | xZmSHChr2 | 73 | 23811 | SHChr2_Cas9 |
| SHChr3.1b | 5'-TAACG AGCAG AGTAC ACACG-3' | xZmSHChr3 | 74 | 23812 | SHChr3_Cas9 |
| SHChr4.1t | 5'- TGAAA GCGAT GCGGT TTAGA-3' | xZmSHChr4 | 75 | 23813 | SHChr4_Cas9 |
| SHChr5.1t | 5'-TACAA TGTAC AGTCT AGCCA-3' | xZmSHChr5 | 76 | 23814 | SHChr5_Cas9 |
| SHChr6.1b | 5'-ACGAG ACCAT CCAAT GATCG-3' | xZmSHChr6 | 77 | 23815 | SHChr6_Cas9 |
| SHChr7.1t | 5'-TGGAG AGTAA TAGGA TGGCA-3' | xZmSHChr 7a | 78 | 23816 | SHChr7a_Cas9 |
| SHChr7.2b | 5'-TGAAA CCAAA CCAGC AGACG-3' | xZmSHChr 7b | 79 | 23817 | SHChr7b_Cas9 |
| SHChr8.1t | 5'-TAGGT TTGAC ATGTG CTAAG-3' | xZmSHChr1 | 80 | 23818 | SHChr8a_Cas9 |
| SHChr8.2b | 5'-CTTCG TAGAC ATATA GATGC-3' | xZmSHChr2 | 81 | 23819 | SHChr8b_Cas9 |

Donor vectors were also constructed to enable the targeted insertion of a DNA of interest at the target maize genomic locus to be mediated by homologous recombination. The donor vector may also be referred to as the donor molecule. A donor vector which contains at least one homologous "arm" flanking the 5' and/or the 3' end of the donor sequence can promote homologous recombination between the arm and the target genomic sequence, thereby leading to targeted insertion by homologous recombination. In these examples, the DNA of interest for each donor vector comprises the coding sequence for the selectable marker phosphomannose isomerase (PMI), which confers an ability to metabolize mannose (U.S. Pat. Nos. 5,767,378 and 5,994,629). The 5' end of the PMI coding sequence is operably linked to a rice actin promoter and the 3' end of the PMI coding sequence is operably linked to a terminator. Immediately 3' to the terminator is a homologous arm, comprising the sequence of SEQ ID NO: 82 to 91 for each corresponding safe harbor sequence, as described in Table 4. This homologous arm is sufficient to enable homologous recombination of the donor molecule into the target maize genomic locus at the cleaved genomic nuclease cleavage site. However, it will be appreciated by a person of skill in the art that the homologous arm can be of a different length, and/or that there can be an additional homologous arm adjacent to the DNA of interest at the 5' end. It will also be appreciated by a person of skill in the art that the presence of the homologous arm(s) enables homologous recombination, however the DNA of interest may still integrate into the genome within the target maize genomic locus by different means, such as non-homologous end joining. These described donor vectors enable CRISPR-Cas9 mediated insertion of the PMI expression cassette at a particular target maize genomic locus by homologous recombination.

As positive controls for targeted insertion, 3 vectors (23813, 23818 and 23819) were constructed for testing intermolecular recombination between donor vectors and the target maize genomic loci (referred to as "target site" in Table 4 below).

TABLE 4

Donor vectors for CRISPR-Cas9 targeted insertion

| Safe harbor ID | Cas9-sgRNA vector ID | Targeted insertion donor vector ID | Targeted insertion donor vector alias | Safe harbor sequence interval in the donor vector | Donor vector safe harbor sequence interval SEQ. ID. NO. |
|---|---|---|---|---|---|
| SHChr1.1b | 23808 | 23829 | SHChr1_donor_V2 | xJHAXSHChr1 | 82 |
| SHChr2.1t | 23811 | 23828 | SHChr2_donor_V2 | xJHAXSHChr2 | 83 |
| SHChr3.1b | 23812 | 23827 | SHChr3_donor_V2 | xJHAXSHChr3 | 84 |
| SHChr4.1t | 23813 | 23826 | SHChr4_donor_V2 | xJHAXSHChr4 | 85 |
| SHChr5.1t | 23814 | 23825 | SHChr5_donor_V2 | xJHAXSHChr5 | 86 |
| SHChr6.1b | 23815 | 23824 | SHChr6_donor_V2 | xJHAXSHChr6 | 87 |
| SHChr7.1t | 23816 | 23823 | SHChr7a_donor_V2 | xJHAXSHChr7a | 88 |
| SHChr7.2b | 23817 | 23822 | SHChr7b_donor_V2 | xJHAXSChr7b | 89 |
| SHChr8.1t | 23818 | 23821 | SHChr8a_donor_V2 | xJHAXSHChr8a | 90 |
| SHChr8.2b | 23819 | 23820 | SHChr8b_donor_V2 | xJHAXSHChr8b | 91 |
| Controls: Intermolecular recombination mediated CRISPIZ-Cas9 | | | | | |
| 23895, with SHChr4V2 target site | 23813 | 23826 | SHChr4_donor_V2 | xJHAXSHChr4 | 85 |
| 23890 with SHChr8aV 2 target site | 23818 | 23821 | SHChr8a_donor_V2 | xJHAXSHChr8a | 90 |
| 23894 with SHChr8bV 2_target site | 23819 | 23820 | SHChr8b_donor_V2 | xJHAXSHChr8bv2 | 91 |

Example 4: Targeted Insertion into Target Maize Genomic Loci in Transiently Transformed Cells Targeted insertion of the donor PMI expression cassette transgene sequence into different target maize genomic loci mediated by RNA-guided Cas9 cleavage was tested by co-delivering a Cas9-sgRNA expression vector along with the corresponding donor vector (Tables 3 and 4) using particle bombardment, following techniques described previously for targeted insertion into the MIR604 insertion site, which is known to be a good safe harbor site (WO16106121). Briefly, a DNA vector comprising a Cas9-sgRNA expression cassette and a donor vector were precipitated onto gold particles (0.6 μm in diameter; Bio-Rad). A total of $2\times10^{10}$ molecules of Cas9-sgRNA expression vector and donor vector at 1:1 ratio were added to a tube of 20 μl prepared gold-glycerol slurry (60 mg/ml) and mixed well by finger tapping. 100 μL of $CaCl_2$) (2.5 M), and 10 μL of spermidine (0.1 M) were successively added and mixed by vortexing at room temperature. The mixture was then incubated on ice for 30 minutes. The DNA-coated particles were pelleted by centrifuging at 13,000 rpm for 1 minute. After discarding the supernatant, the particles were washed with 200 μL of absolute ethanol by vortexing for 30 seconds, centrifuging for 1 minute, and removing the supernatant and re-suspended in 20 μL of absolute ethanol. For each bombardment, 6 μL of the particle suspension was pipetted onto the center of macrocarriers. Bombardments of 3-day-old pre-cultured immature embryos in osmoticum medium were carried out using a Biolistic particle acceleration device (PDS 1000/He, Bio-Rad) under a chamber pressure of 27.5 mm of Hg at distances of 8, 10, and 65 mm from the rupture disc to the macrocarriers to the stopping screen to the target, respectively, with 1100 psi helium pressures and 3 shots per plates. The combination of Cas9-sgRNA vector, donor vector and numbers of target explants are listed in Table 5. Three days after bombardment, 25 bombarded embryos from each plate were removed for DNA extraction and PCR analysis to determine if targeted insertion of the DNA of interest (PMI expression cassette) into the safe harbor loci in the transformed cells was successful. Two samples were collected for each plate. Positive control experiments with sequences of targeted maize genomic loci cloned into vectors and co-delivered with their respective donors and Cas9-sgRNA expression vectors into maize cells were also performed to assay extra-chromosomal intermolecular recombination.

TABLE 5

Targeted insertion of target genomic loci by CRISPR-Cas9

| Safe harbor ID | Cas9 vector | Donor vector | Total # of embryos | # of embryos for 1$^{st}$ PCR | Explants to mannose selection | # of mannose resistant callus |
|---|---|---|---|---|---|---|
| SHChr1.lb | 23808 | 23829 | 153 | 25 X 2 | 103 | 18 |
| SHChr2.1t | 23811 | 23828 | 134 | 25 X 2 | 84 | 10 |
| SHChr3.1b | 23812 | 23827 | 155 | 25 X 2 | 105 | 35 |
| SHChr4.1t | 23813 | 23826 | 140 | 25 X 2 | 90 | 21 |
| SHChr5.1t | 23814 | 23825 | 121 | 25 X 2 | 71 | 21 |
| SHChr6.1b | 23815 | 23824 | 153 | 25 X 2 | 103 | 27 |
| SHChr7.1t | 23816 | 23823 | 161 | 25 X 2 | 111 | 16 |
| SHChr7.2b | 23817 | 23822 | 150 | 25 X 2 | 100 | 32 |
| SHChr8.1t | 23818 | 23821 | 158 | 25 X 2 | 108 | 13 |
| SHChr8.2b | 23819 | 23820 | 132 | 25 X 2 | 82 | 31 |
| Positive control 1: 23895, with SHChr4V2 target site | 23813 | 23895 | 135 | 25 X 2 | N.A. | N.A. |
| Positive control 2: 23890 with SHChr8aV2 target site | 23818 | 23890 | 132 | 25 X 2 | N.A. | N.A. |
| Positive control 3: 23894 with SHChr8bV2 target site | 23819 | 23894 | 121 | 25 X2 | N.A. | N.A. |

Example 5: Molecular Demonstration of Targeted Insertion into Selected Safe Harbor Loci in Transiently Transformed Cells Genomic DNA was extracted from bombed maize embryo samples using Promega's Magnesil paramagnetic particles (www.promega.com). PCR primers were designed across the expected 5' and 3' homologous recombination junctions for detecting the targeted insertions (Table 6). For each of the expected recombination site, one primer was designed against a genomic sequence of the safe harbor interval, outside the targeted insertion site. The second primer (SEQ ID NO: 105) was designed against a sequence of the donor PMI expression cassette (Table 6). Table 6 also indicates the expected PCR product if targeted insertion was successful. Primers were also designed for the positive controls to assay intermolecular recombination.

TABLE 6

PCR primers for targeted insertion assay

| Safe harbor ID | SEQ ID NO. of genomic primer | Cas9-sgRNA vector ID | Donor vector ID | Expected PCR product (bp) |
|---|---|---|---|---|
| SHChr1.1b | 92 | 23808 | 23829 | 1603 |
| SHChr2.1t | 93 | 23811 | 23828 | 1603 |
| SHChr3.1t | 94 | 23812 | 23827 | 1746 |
| SHChr4.1t | 95 | 23813 | 23826 | 1545 |
| SHChr5.1t | 96 | 23814 | 23825 | 1532 |
| SHChr6.1b | 97 | 23815 | 23824 | 1563 |
| SHChr7.1t | 98 | 23816 | 23823 | 1490 |
| SHChr7.2b | 99 | 23817 | 23822 | 1633 |
| SHChr8.1t | 100 | 23818 | 23821 | 1454 |
| SHChr8.2b | 101 | 23819 | 23820 | 1497 |
| 23895, with SHChr4V2 target site | 102 | 23813 | 23826 | 1559 |
| 23890 with SHChr8aV2 target site | 103 | 23818 | 23821 | 1598 |
| 23894 with SHChr8bV2_ target site | 104 | 23819 | 23820 | 1513 |

To detect targeted insertions in the transiently transformed embryos, two sequential PCR reactions were carried out on each sample to detect potential recombination products using PCR primers designed to amplify across the expected 5' and 3' homologous recombination junctions for detecting the targeted insertions (Table 6). The first PCR reaction was setup with 12.5 ul of Sigma JumpStart™ REDTaq ReadyMix™ Reaction Mix, 1 μl of each primers, 4 μl of gDNA and 6.5 μl of H2O. The second PCR reaction was setup with 12.5 μl of Sigma JumpStart™ REDTaq ReadyMix™ Reaction Mix, 1 μl of each primers, 2 μl of the first PCR product as template and 8.5 μl of H2O. PCR was performed on Applied Biosystems Veriti 96 Well Thermal Cycler with following amplification parameters: 95° C. for 5 minutes, 35 cycles of (95° C. 30 seconds, 55° C., 57° C. or 60° C. for 30 seconds as needed and 72° C. for 2 minutes), followed by 7 minutes at 72° C. and then hold at 4° C. until gel electrophoresis. After PCR, 10 μl of PCR product was run on a 1% agarose gel containing SyBR Safe DNA Gel Stain for visualization. PCR products of expected sizes were observed clearly in targeting experiments of 5 safe harbor sites, such that a call could be made regarding the successful targeted integration (Table 7). PCR products were cleaned up with EXO-SAP treatment before sending to Sanger sequence and subjected to Sanger sequencing. Sequencing analysis was carried out using SEQUENCHER™ software, and the sequence data was compared to the reference sequence. These results confirmed successful targeted insertion of the PMI expression cassette into the target genomic loci (SHChr5.1t and SHChr7.1t).

TABLE 7

Analysis of transiently transformed maize embryos for targeted insertion

| Safe harbor ID | # of bombed embryos | PCR results | Sequence results confirming targeted insertion? |
|---|---|---|---|
| SHChr1.1b | 50 | − | No data |
| SHChr2.1t | 50 | + | No |
| SHChr3.1t | 50 | − | No data |
| SHChr4.1t | 50 | − | No data |
| SHChr5.1t | 50 | + | Yes, confirmed the linkage of PMI to region flanking xJHAXSHChr5 |
| SHChr6.1b | 50 | +/−? | No |
| SHChr7.1t | 50 | + | Yes, confirmed the linkage of PMI to region flanking xJHAXSHChr7a |
| SHChr7.2b | 50 | + | No |
| SHChr8.1t | 50 | − | No data |
| SHChr8.2b | 50 | − | No data |

Example 6: Targeted Insertion into Selected Safe Harbor Sites in Stably Transformed Cells The remaining explants from each plate after sampling at 3 days post-bombardment were transferred onto callus induction media for 10 days. Induced calli were then transferred onto mannose selection media. After 4 weeks of culturing in mannose-contained medium the PMI resistant calli were individually sampled, subjected to DNA extraction and PCR analysis. The numbers of mannose resistant callus were list in Table 8. Genomic DNA was extracted separately from maize embryo and callus tissue. Two sequential PCR reactions were carried out on each sample to detect potential recombination products as described above for transient targeting assays (Table 6 and Table 7). The results of PCR and Sanger sequence analysis are summarized in Table 8. Positive PCR products of expected sizes were found in 6 of 10 tested safe harbor loci. Sanger sequence analysis further confirmed targeted insertion in 3 (SHChr4.1t, SHChr5.1t and SHChr6.1b) out of the 10 target maize genomic loci tested in stably transformed callus tissues. It should be noted that negative PCR or sequencing results do not mean that these safe harbor loci are not amenable to targeted insertion; only very limited experiments were done with each safe harbor locus.

TABLE 8

Analysis of stably transformed tissue for targeted insertion

| Safe harbor ID | # of calli sampled | PCR results | Sequence results confirming targeted insertion? |
|---|---|---|---|
| SHChr1.1b | 18 | no positive | No data |
| SHChr2.1t | 10 | 6 positive | No |

TABLE 8-continued

Analysis of stably transformed tissue for targeted insertion

| Safe harbor ID | # of calli sampled | PCR results | Sequence results confirming targeted insertion? |
|---|---|---|---|
| SHChr3.1t | 35 | 1 positive | No |
| SHChr4.1t | 21 | 1 positive | Yes, confirmed the linkage of PMI to region flanking xJHAXSHChr4 |
| SHChr5.1t | 21 | 1 positive | Yes, confirmed the linkage of PMI to region flanking xJHAXSHChr5 |
| SHChr6.1b | 27 | 1 positive | Yes, confirmed the linkage of PMI to region flanking xJHAXSHChr6 |
| SHChr7.1t | 16 | 12 positive | No |
| SHChr7.2b | 32 | No positive | No data |
| SHChr8.1t | 14 | No positive | No data |
| SHChr8.2b | 31 | No positive | No data |

What is claimed is:

1. A method of integrating a DNA of interest into a target maize genomic locus in a maize genome, wherein the target maize genomic locus comprises a nucleic acid sequence having at least 100 contiguous nucleotides of SEQ ID NO: 65 or the complement thereof, comprising introducing into a maize cell:

a) a first nucleic acid molecule comprising at least 100 contiguous nucleotides with at least 100 contiguous nucleotides of SEQ ID NO: 65 or the complement thereof, and further comprising the DNA of interest; and b) a second nucleic acid molecule comprising a nucleotide sequence encoding a nuclease for site-directed cleavage at a genomic nuclease cleavage site within the target maize genomic locus, under conditions wherein expression of the second nucleic acid molecule can occur to produce the nuclease and the nuclease can cleave the nucleotide sequence at the genomic nuclease cleavage site, whereby the DNA of interest is integrated into the target maize genomic locus in the maize genome.

2. The method of claim 1, wherein two or more DNA of interest are inserted into two or more targeted maize genomic loci.

3. The method of claim 1, wherein the DNA of interest inserted into the target maize genomic locus via homologous recombination.

4. The method of claim 1, wherein the DNA of interest inserted into the target maize genomic locus via non-homologous end-joining.

5. The method of claim 1, wherein the DNA of interest and/or the target maize genomic locus are modified during insertion of said DNA of interest into said target maize genomic locus.

6. A method of producing a maize plant, plant part, or progeny thereof comprising a DNA of interest, comprising regenerating a maize plant from the maize cell produced by the method of claim 1.

7. A maize plant, plant part, or progeny thereof comprising a DNA of interest, produced by the method of claim 6.

8. A method of making a maize plant cell comprising a DNA of interest, said method comprising:

a. selecting a target maize genomic locus, wherein the target maize genomic locus comprises a nucleic acid sequence having a sequence selected from the group consisting of SEQ ID NO: 65, and the complement thereof;
b. selecting a site specific nuclease that specifically binds to and cleaves a genomic nuclease cleavage site within said target maize genomic locus;
c. introducing said site specific nuclease and a DNA of interest into the maize plant cell;
d. allowing the DNA of interest to insert into the target maize genomic locus; and
e. selecting maize plant cells that comprise the DNA of interest inserted into the target maize genomic locus.

9. The method of claim 8, wherein two or more DNAs of interest are inserted into two or more targeted maize genomic loci.

10. The method of claim 8, wherein the DNA of interest is inserted into the target maize genomic locus via homologous recombination.

11. The method of claim 8, wherein the DNA of interest is inserted into the target genomic locus via non-homologous end-joining.

12. The method of claim 8, wherein the DNA of interest and/or the target maize genomic locus are modified during insertion of said DNA of interest into said target maize genomic locus.

13. The method of claim 8, wherein the site specific nuclease is a Cas-associated nuclease and wherein a third nucleic acid molecule encoding a guide RNA is introduced into the maize cell.

14. The method of claim 8, wherein the site specific nuclease is a Cas-associated nuclease and wherein a third nucleic acid molecule encoding a guide RNA is introduced into the maize cell.

15. A method of producing a maize plant or plant part, or progeny thereof, comprising a transgene integrated into a genomic nuclease cleavage site in the maize genome, comprising regenerating a maize plant from the maize cell produced by the method of claim 8.

16. A maize plant or plant part, or progeny thereof, comprising a transgene integrated into a genomic nuclease cleavage site in the maize genome, produced by the method of claim 15.

* * * * *